(12) United States Patent
Zhang et al.

(10) Patent No.: US 10,016,532 B2
(45) Date of Patent: Jul. 10, 2018

(54) NON-FOULING, ANTI-MICROBIAL, ANTI-THROMBOGENIC GRAFT COMPOSITIONS

(71) Applicant: ARROW INTERNATIONAL, INC., Wayne, PA (US)

(72) Inventors: Zheng Zhang, Cambridge, MA (US); Jun Li, Brookline, MA (US); Chad C. Huval, Somerville, MA (US); Michael A. Bouchard, Wyomissing, PA (US); Arthur J. Coury, Boston, MA (US); Christopher R. Loose, Cambridge, MA (US)

(73) Assignee: ARROW INTERNATIONAL, INC., Wayne, PA (US)

( * ) Notice: Subject to any disclaimer, the term of this patent is extended or adjusted under 35 U.S.C. 154(b) by 90 days.

(21) Appl. No.: 14/533,908

(22) Filed: Nov. 5, 2014

(65) Prior Publication Data
US 2015/0056411 A1 Feb. 26, 2015

Related U.S. Application Data

(63) Continuation of application No. 13/156,708, filed on Jun. 9, 2011.
(Continued)

(51) Int. Cl.
A61L 31/10 (2006.01)
A61L 27/34 (2006.01)
A61L 27/54 (2006.01)
A61L 33/00 (2006.01)
B32B 9/04 (2006.01)
B32B 15/04 (2006.01)
B32B 27/40 (2006.01)
A61L 31/16 (2006.01)
B32B 5/02 (2006.01)
B32B 5/16 (2006.01)
B32B 5/26 (2006.01)
B32B 5/30 (2006.01)
B32B 9/00 (2006.01)
B32B 15/08 (2006.01)
B32B 15/14 (2006.01)
B32B 15/16 (2006.01)
B32B 27/08 (2006.01)
(Continued)

(52) U.S. Cl.
CPC ............ A61L 31/10 (2013.01); A61L 27/34 (2013.01); A61L 27/54 (2013.01); A61L 31/16 (2013.01); A61L 33/0029 (2013.01); B32B 5/022 (2013.01); B32B 5/024 (2013.01); B32B 5/16 (2013.01); B32B 5/26 (2013.01); B32B 5/30 (2013.01); B32B 9/00 (2013.01); B32B 9/005 (2013.01); B32B 9/04 (2013.01); B32B 9/041 (2013.01); B32B 9/043 (2013.01); B32B 9/047 (2013.01); B32B 9/048 (2013.01); B32B 15/04 (2013.01); B32B 15/043 (2013.01); B32B 15/08 (2013.01); B32B 15/14 (2013.01); B32B 15/16 (2013.01); B32B 27/08 (2013.01); B32B 27/12 (2013.01); B32B 27/14 (2013.01); B32B 27/28 (2013.01); B32B 27/281 (2013.01); B32B 27/283 (2013.01); B32B 27/285 (2013.01); B32B 27/286 (2013.01); B32B 27/288 (2013.01); B32B 27/34 (2013.01); B32B 27/36 (2013.01); B32B 27/365 (2013.01); B32B 27/38 (2013.01); B32B 27/40 (2013.01); A61L 2300/252 (2013.01); A61L 2300/404 (2013.01); A61L 2300/42 (2013.01); A61L 2300/606 (2013.01); A61L 2420/02 (2013.01); B32B 2255/10 (2013.01); B32B 2255/26 (2013.01); B32B 2307/538 (2013.01); B32B 2307/7145 (2013.01); B32B 2307/732 (2013.01); B32B 2535/00 (2013.01); Y10T 428/24364 (2015.01); Y10T 428/26 (2015.01); Y10T 428/265 (2015.01); Y10T 428/2962 (2015.01); Y10T 428/31504 (2015.04); Y10T 428/31551 (2015.04); Y10T 428/31598 (2015.04); Y10T 428/31612 (2015.04); Y10T 428/31663 (2015.04); Y10T 428/31678 (2015.04); Y10T 428/31855 (2015.04); Y10T 442/30 (2015.04); Y10T 442/60 (2015.04)

(58) Field of Classification Search
CPC ..... A61L 2300/404; A61L 27/54; A61L 31/10
USPC ....... 427/2.1, 2.24, 2.28, 2.3, 299, 301, 333, 427/402
See application file for complete search history.

(56) References Cited

U.S. PATENT DOCUMENTS 4,098,728 A 7/1978 Rosenblatt
4,211,227 A 7/1980 Anderson et al.
(Continued)

FOREIGN PATENT DOCUMENTS

EP 0479245 A2 4/1992
JP H08-131536 A 5/1996
(Continued)

OTHER PUBLICATIONS

Vermette, P. et al., Tissue Engineering Intelligence Unit 6, Biomedical Applications of Polyurethanes, Chapter 7, 2001, 175-211.
Feng et al., Atom-Transfer Radical Grafting Polymerization of 2-Methacryloyloxyethyl Phosphorycholine from Silicon Wafer Surfaces. Journal of Polymer Science Part A: Polymer Chemistry 2004, 42, 2931-2942.
(Continued)

Primary Examiner — Cachet I Sellman
(74) Attorney, Agent, or Firm — Baker Hostetler LLP

(57) ABSTRACT

The present invention generally relates to articles of manufacture, such as medical devices, having a non-fouling surface comprising a grafted polymer material. The surface resists the adhesion of biological material.

24 Claims, No Drawings

Related U.S. Application Data

(60) Provisional application No. 61/353,208, filed on Jun. 9, 2010.

(51) Int. Cl.
*B32B 27/12* (2006.01)
*B32B 27/14* (2006.01)
*B32B 27/28* (2006.01)
*B32B 27/34* (2006.01)
*B32B 27/36* (2006.01)
*B32B 27/38* (2006.01)

(56) References Cited

U.S. PATENT DOCUMENTS

| | | | |
|---|---|---|---|
| 4,480,011 A | 10/1984 | Durand et al. | |
| 4,636,208 A | 1/1987 | Rath | |
| 4,877,864 A | 10/1989 | Wang et al. | |
| 5,002,794 A | 3/1991 | Ratner et al. | |
| 5,013,649 A | 5/1991 | Wang et al. | |
| 5,180,375 A | 1/1993 | Feibus | |
| 5,453,467 A | 9/1995 | Bamford et al. | |
| 5,536,248 A | 7/1996 | Weaver et al. | |
| 5,661,007 A | 8/1997 | Wozney et al. | |
| 5,688,678 A | 11/1997 | Hewick et al. | |
| 5,739,236 A | 4/1998 | Bowers et al. | |
| 5,844,016 A | 12/1998 | Sawhney et al. | |
| 5,866,113 A | 2/1999 | Hendriks et al. | |
| 5,997,895 A | 12/1999 | Narotam et al. | |
| 6,054,504 A | 4/2000 | Dalla Riva Toma | |
| 6,120,536 A | 9/2000 | Ding | |
| 6,150,459 A | 11/2000 | Mayes et al. | |
| 6,177,406 B1 | 1/2001 | Wang et al. | |
| 6,200,338 B1 | 3/2001 | Solomon et al. | |
| 6,251,964 B1 | 6/2001 | Porssa et al. | |
| 6,284,854 B1 | 9/2001 | Bowers et al. | |
| 6,358,557 B1 | 3/2002 | Wang et al. | |
| 6,361,768 B1 | 3/2002 | Galleguillos et al. | |
| 6,387,977 B1 | 5/2002 | Sawhney et al. | |
| 6,395,800 B1 | 5/2002 | Jones et al. | |
| 6,432,919 B1 | 8/2002 | Wang et al. | |
| 6,489,382 B1 | 12/2002 | Giesecke et al. | |
| 6,534,268 B1 | 3/2003 | Kawai et al. | |
| 6,558,734 B2 | 5/2003 | Koulik et al. | |
| 6,559,242 B1 | 5/2003 | Ball et al. | |
| 6,589,665 B2 | 7/2003 | Chabrecek et al. | |
| 6,711,879 B2 | 3/2004 | Korteweg et al. | |
| 6,844,028 B2 | 1/2005 | Mao et al. | |
| 7,087,658 B2 | 8/2006 | Swan et al. | |
| 7,220,491 B2 | 5/2007 | Rouns et al. | |
| 7,238,364 B2 | 7/2007 | Sawhney et al. | |
| 7,238,426 B2 | 7/2007 | Jiang et al. | |
| 7,276,286 B2 | 10/2007 | Chapman et al. | |
| 7,300,990 B2 | 11/2007 | Lewis et al. | |
| 7,306,625 B1 | 12/2007 | Stratford et al. | |
| 7,431,888 B2 | 10/2008 | Frechet et al. | |
| 7,629,029 B2 | 12/2009 | Mao et al. | |
| 7,879,444 B2 | 2/2011 | Jiang et al. | |
| 9,096,703 B2 | 8/2015 | Li et al. | |
| 2001/0050749 A1 | 12/2001 | Watanabe | |
| 2003/0021823 A1 | 1/2003 | Landers et al. | |
| 2003/0143335 A1 | 7/2003 | Qiu et al. | |
| 2003/0216804 A1 | 11/2003 | DeBeer et al. | |
| 2004/0148003 A1 | 7/2004 | Udipi et al. | |
| 2004/0253383 A1 | 12/2004 | Belik et al. | |
| 2004/0256232 A1 | 12/2004 | Jiang et al. | |
| 2005/0131522 A1 | 6/2005 | Stinson et al. | |
| 2006/0057180 A1* | 3/2006 | Chilkoti | A61L 27/34 424/422 |
| 2006/0217285 A1 | 9/2006 | Destarac | |
| 2007/0048249 A1 | 3/2007 | Youngblood et al. | |
| 2007/0104891 A1* | 5/2007 | Fournand | C09D 5/1662 427/561 |
| 2007/0254006 A1 | 11/2007 | Loose et al. | |
| 2008/0181861 A1* | 7/2008 | Jiang | B82Y 30/00 424/78.09 |
| 2008/0207581 A1 | 8/2008 | Whiteford et al. | |
| 2008/0234792 A1 | 9/2008 | Reddy et al. | |
| 2008/0255305 A1 | 10/2008 | Brook et al. | |
| 2008/0286332 A1 | 11/2008 | Pacetti | |
| 2009/0155335 A1* | 6/2009 | O'Shaughnessey | A61L 15/46 424/423 |
| 2009/0162662 A1 | 6/2009 | Chang et al. | |
| 2009/0197791 A1 | 8/2009 | Balastre et al. | |
| 2009/0259015 A1 | 10/2009 | Jiang et al. | |
| 2009/0311301 A1 | 12/2009 | Kleiner et al. | |
| 2010/0035074 A1 | 2/2010 | Cohen et al. | |
| 2010/0072642 A1 | 3/2010 | Broad et al. | |
| 2010/0099160 A1 | 4/2010 | Jiang et al. | |

FOREIGN PATENT DOCUMENTS

| | | |
|---|---|---|
| JP | H11-47263 A | 2/1999 |
| JP | 2001-337298 A | 12/2001 |
| JP | 2004-121618 A | 4/2004 |
| JP | 2007-130194 | 5/2007 |
| JP | 2007-152097 A | 6/2007 |
| WO | 9505408 | 2/1995 |
| WO | 03000433 | 1/2003 |
| WO | 2007002493 | 1/2007 |
| WO | 2007/024393 A2 | 3/2007 |
| WO | 2007024393 | 3/2007 |
| WO | 2007095393 | 8/2007 |
| WO | 2008006911 | 1/2008 |
| WO | 2008019381 | 2/2008 |
| WO | 2008083390 | 7/2008 |
| WO | 2009079664 | 6/2009 |
| WO | 2009085096 | 7/2009 |
| WO | 2010065960 | 6/2010 |

OTHER PUBLICATIONS

Goda et al., Biomimetic phosphoryl choline polymer grafting from polydimethylsiloxane surface using photo-induced polymerization. Biomaterials 2006, 27 (30), 5151-60.

Ishihara, et al. Photoinduced graft polymerization of 2-nriethacryloyloxyethyl phosphorylcholine on polyethylene membrane surface for obtaining blood cell adhesion resistance. Colloids Surf B Biointerfaces 2000,18 (3-4), 325-335.

Yuan et al., Improvement of blood compatibility on cellulose membrane surface by grafting betaines. Colloids and Surfaces B: Biointerfaces 30.

Jiang et al., Blood compatibility of polyurethane surface grafted copolymerization with sulfobetaine monomer. Colloids Surf B Biointerfaces 2004, 36 (1),27-33.

Jin et al., Protein-resistant polyurethane prepared by surface-initiated atom transfer radical graft polymerization (ATRgP) of water-soluble polymers: effects of main chain and side chain lengths of grafts. Colloids Surf B Biointerfaces 2009, 70 (1),53-9.

Jin et al., Protein-resistant polyurethane via surface-initiated atom transfer radical polymerization of oligo(ethylene glycol) methacrylate. J Biomed Mater Res A 2009, 91(4), 1189-201.

Zhang et al., Chemical modification of cellulose membranes with sulfo ammonium zwitlerionic vinyl monomer to improve hemocompatibility. Colloids and Surfaces B: Biointerfaces 30.

Kang et al., Surface modification and functionalization of electroactive polymer films via grafting of polyelectrolyte, polyampholyte and polymeric acids. Journal to Materials Science 1996, 31, 1295-1301.

Fujimoto et al., Ozone-induced graft polymerization onto polymer surface. J Polym Sci A Polym Chem 1993, 31, 1035-1043.

Liu et al., Grafting of Zwitterion from Cellulose Membranes via ATRP for Improving Blood Compatibility. Biomacromolecules 2009,10 (10), 2809-2816.

Villa-Diaz et al., Synthetic polymer coatings for long-term growth of human embryonic stem cells. Nat Biotechnol 2010, 28(6),581-3.

Yuan et al., Polyurethane vascular catheter surface grafted with zwitlerionic sulfobetaine monomer activated by ozone. Colloids and Surfaces B: Biointerfaces 35.

(56) References Cited

OTHER PUBLICATIONS

Yuan et al., Chemical graft polymerization of sulfobetaine monomer on polyurethane surface for reduction in platelet adhesion. Colloids Surf B Biointerfaces 2004,39 (1-2), 87-94.
Yuan et al., Platelet adhesion onto segmented polyurethane surfaces modified by carboxybetaine. J Biomater Sci Polym Ed 2003,14 (12), 1339-49.
Yuan et al., Grafting Sulfobetaine monomer onto the segmented poly(ether-urethane) surface to improve hemocompatibility. J Biomaterial Sci Polym Ed 2002, 13, 1081-92.
Yuan et al., Surface modification of SPEC films by ozone induced graft copolymerization to improve hemocompatibility. Colloids and Surfaces B: Biointerfaces 2003, 29, 247-256.
Zhang et al., Nonfouling Behavior of Polycarboxybetaine-Grafted Surfaces: Structural and Environmental Effects—Biomacromolecules (ACS Publications). Biomacromolecules (Web): Sep. 12, 2008, 10, 2686-92.
Cheng et al., Thickness-Dependent Properties of Polyzwitterionic Brushes, Macromolecules, 2008, 41, 6317-6321.
Odian, G., Polymerization Mechanism, Types of Polymers and Polymerizations, p. 6-7.
Salim et al., Studies of electroosmotic flow and the effects of protein adsorptiion in plasma-polymerized microchannel surfaces, Electrophoresis 2009, 30, 1877-1887.
Patent Cooperation Treaty, International Search Report for PCT/US2011/039790, mailed Mar. 12, 2012, 4 pages.
Patent Cooperation Treaty, International Search Report for PCT/US2011/039792, mailed Mar. 12, 2012, 6 pages.
Bell et al., Biomedical membranes from hydrogels and interpolymer complexes. Biopolymers II, 1995,122, 125—175.
Chapman et al., Polymeric Thin Films That Resist the Adsorption of Proteins and the Adhesion of Bacteria. Langmuir 2001, 17 (4), 1225-1233.
Kildal et al., Peroxide-initiated granfling of acrylaminde on to polyethylene surfaces, Journal of Applied Polymer Science, 1992, 44, 1893-1898.
Patent Cooperation Treaty, International Search Report for PCT/US2009/067007, mailed May 7, 2010, 3 pages.
Cheng et al., Zwitterionic carboxybetaine polymer surfaces and their resistance to long-term biofilm formation. Biomaterials 2009, 30 (28), 5234-40.
Cheng et al., Inhibition of bacterial adhesion and biofilm formation on zwitterionic surfaces. Biomaterials 2007, 28 (29), 4192-9.
Du et al., Grafted poly-(ethylene glycol) on lipid surfaces inhibits protein adsorption and cell adhesion. Biochimica et Biophysica Acta (BBA)—Biomembranes 1997, 1326 (2), 236-248.
Harder et al., Molecular Conformation in Oligo(ethylene glycol)-Terminated Self-Assembled Monolayers on Gold and Silver Surfaces Determines Their Ability To Resist Protein Adsorption. The Journal of Physical Chemistry B 1998, 102 (2), 426-436.
Haynie et al., Antimicrobial activities of amphiphilic peptides covalently bonded to a water-insoluble resin. Antimicrobial Agents and Chemotherapy 1995, 39 (2), 301-307.
Ignatova et al., Combination of electrografting and atom-transfer radical polymerization for making the stainless steel surface antibacterial and protein antiadhesive, Langmuir, 2005, 22(1), 255-262.
Lowe et al., Well-defined sulfobetaine-based statistical copolymers as potential antibioadherent coatings. J Biomed Mater Res 2000, 52, 88-94.
Massia et al., Immobilized RGD peptides on surface-grafted dextran promote biospecific cell attachment. J Biomed Mater Res 2001, 56 (3), 390-399.
Michel et al., Influence of PEG Architecture on Protein Adsorption and Conformation. Langmuir 2005, 21 (26), 12327-12332.
Sakharov et al., Catalytic oxidative deformylation of polyethylene glycols with the participation of molecular oxygen. Kinet Catal 2001, 42, 662-668.
Tada et al., Anti-biofouling properties of polymers with a carboxybetaine moiety. Macromol Biosci 2009, 9 (1), 63-70.
Wang et al., Antifouling ultrafiltration membrane composed of polyethersulfone and sulfobetaine copolymer. Journal of Membrane Science 2006, 280, 343-350.
West et al., The biocompatibility of crosslinkable copolymer coatings containing sulfobetaines and phosphobetaines. Biomaterials 2004, 25 (7-8), 1195-204.
Wozney et al., Novel regulators of bone formation: molecular clones and activities. Science 1988, 242 (4885), 1528-1534.
Zhang et al., Surface grafted sulfobetaine polymers via atom transfer radical polymerization as superlow fouling coatings. J Phys Chem B 2006, 110 (22), 10799-804.
Zhang et al., Blood compatibility of surfaces with superlow protein adsorption. Biomaterials 2008, 29 (32), 4285-91.
Zhang et al., Superlow Fouling Sulfobetaine and Carboxybetaine Polymers on Glass Slides. Langmuir 2006, 22 (24), 10072-10077.
Jiang, Zwitterionic Separation Materials for Liquid Chromatography and Capillary Electrophoresis Synthesis, Characterization and Application for Inorganic Ion and Biomolecule Separations, PhD Dissertation, Umea University, Umea, Sweden, 63 pages.
Jun et al., Surface modification of segmented poly(ether urethane) by grafting sulfo ammonium zwitterionic monomer to improve hemocompatibilities, Colloids and Surfaces B: Biointerfaces, 2003, 28(1), 1-9.
European Patent Office, Extended European Search Report for EP 11793155.0 publication EP 2579904, dated Oct. 29, 2015, 6 pages.
Bamford et al., "Studies in Polymer Surface Functionalization and Grafting for Biomedical and Other Applications", Polymer, 1994, vol. 35, No. 13, pp. 2844-2852.

\* cited by examiner

NON-FOULING, ANTI-MICROBIAL, ANTI-THROMBOGENIC GRAFT COMPOSITIONS

CROSS-REFERENCE TO RELATED APPLICATIONS

This application is a Continuation application of U.S. application Ser. No. 13/156,708 filed Jun. 9, 2011, which claims the benefit of priority to U.S. Patent Application Ser. No. 61/353,208, filed Jun. 9, 2010, the contents of which are incorporated herein by reference in their entirety.

FIELD OF THE INVENTION

The present invention generally relates to articles of manufacture, such as medical devices, having a non-fouling surface comprising a grafted polymer material. The surface resists the adhesion of biological material.

BACKGROUND OF THE INVENTION

Many different materials have been investigated to resist non-specific protein adsorption. Chemistries utilized for this purpose include, but are not limited to: polyethers (e.g., polyethylene glycol), polysaccharides such as dextran, hydrophilic polymers such as polyvinylpyrrolidone or hydroxyethyl-methacrylate, heparin, intramolecular zwitterions or mixed charge materials, and hydrogen bond accepting groups such as those described in U.S. Pat. No. 7,276,286. The ability of these materials in preventing protein adsorption varies greatly between the chemistries. Of these materials, only a few resist fouling to the degree required for short-term in vivo application. However, the few materials appropriate for short-term application, when used for longer periods of time in complex media or in vivo, exhibit significant fouling or other degradation, making them unsuitable for long-term applications. Furthermore, surfaces coated with materials that resist in vivo degradation are often susceptible to a noticeable decrease in fouling resistance over time.

Biocompatible coatings, especially those applied to medical device substrates, have been applied by dip coating the substrate in a single polymer solution. For hydrophilic polymers applied to hydrophobic substrates, this approach presents many challenges as it can be difficult to form stable coatings. In an attempt to improve stability, hydrophilic materials have been cross-linked or copolymerized with hydrophobic groups. However, such approaches can have significant negative effects on the overall coating performance, especially when resistance to protein adsorption is desired.

Conventional fouling resistant or non-fouling materials and surface coatings are susceptible to fouling over prolonged exposure to complex media or in vivo environments. The materials used for many non-fouling and fouling resistant coatings, or the tethers used to immobilize the coatings on a substrate, have not, to date, possessed the stability required to coat the substrate for extended periods of time, for example, at least 7, 14, 30, 60, 90, 120, 365, or 1000 days.

SUMMARY OF THE INVENTION

Among the various aspects of the present invention is the provision of medical devices and other articles of manufacture having a grafted non-fouling polymeric material with sufficient stability to protect the substrate for extended periods of time, for example, at least 7, 14, 30, 60, 90, 120, 365, or 1000 days. The non-fouling polymeric material is grafted to or from a polymeric primer which, in turn, coats at least a portion of the medical device or other article of interest.

Advantageously, the non-fouling polymeric material may be used to modify the surface of a range of substrates, including such diverse materials as metals, metal oxides, polymers, tissues, and fibers. Further, the non-fouling polymeric material may possess a range of polymeric backbones and substituents while providing the articles with a highly efficient, biocompatible, and non-fouling modified surface. Additionally, the non-fouling polymeric material retains its activity in the presence of blood proteins and/or in vivo due to improved molecular structures. In another embodiment, bioactive compositions are attached to the modified surface.

Briefly, therefore, the present invention is directed to an article of manufacture comprising a polymer layer, a substrate, and a polymeric primer between the polymer layer and the substrate. The polymeric primer has upper and lower surfaces, the lower surface covering at least a portion of the substrate, and the upper surface being bound to the polymer layer. The polymeric primer upper surface and the polymer layer, in combination, constitute a modified surface for the article, the modified surface having a fibrinogen adsorption of less than about 125 ng/cm$^2$ in a fibrinogen binding assay in which the modified surface is incubated for 60 minutes at 37° C. in a solution containing 70 µg/ml fibrinogen derived from human plasma and 1.4 µg/ml I-125 radiolabeled fibrinogen. In one embodiment, the polymeric primer upper surface and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another embodiment, the polymeric primer upper surface and the polymer layer in combination, constitute a modified surface having a fibrinogen adsorption of less than about 75 ng/cm$^2$ in a fibrinogen binding assay in which the modified surface is incubated for 60 minutes at 37° C. in 70 µg/mL fibrinogen derived from human plasma containing 1.4 µg/mL I-125 radiolabeled fibrinogen. In another embodiment, the polymeric primer upper surface and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

The present invention is further directed to a process for the preparation of an article of manufacture. The process comprises coating at least a portion of a substrate with a polymer primer to form a polymeric primer on the substrate. The process further comprises forming a bonded polymer layer on the polymeric primer, the polymeric primer being between the polymer layer and the substrate. The polymeric primer has upper and lower surfaces, the lower surface covering at least a portion of the substrate, and the upper surface being covalently bound to the polymer layer. The polymeric primer and the polymer layer, in combination, constitute a modified surface having a fibrinogen adsorption of less than about 125 ng/cm$^2$ in a fibrinogen binding assay in which the modified surface is incubated for 60 minutes at 37° C. in 70 µg/ml fibrinogen derived from human plasma containing 1.4 µg/ml I-125 radiolabeled fibrinogen. In one embodiment, the polymeric primer and the polymer layer, in combination, constitute a modified surface having a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another embodiment, the polymeric primer and the polymer layer in combination, constitute a modified surface having a fibrinogen adsorption of less than about 75 ng/cm$^2$ in a fibrinogen binding assay in which the modified surface is incubated for 60 minutes at 37° C. in 70 µg/mL fibrinogen derived from human plasma containing 1.4 µg/mL I-125 radiolabeled fibrinogen. In another embodiment, the polymeric primer and the polymer layer, in combination, constitute a modified surface having a fibrinogen adsorption of less than about 50 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen.

Other objects and features will be in part apparent and in part pointed out hereinafter.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

When introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

Aliphatic: unless otherwise indicated, "aliphatic" or "aliphatic group" means an optionally substituted, non-aromatic hydrocarbon moiety. The moiety may be, for example, linear, branched, or cyclic (e.g., mono or polycyclic such as fused, bridging, or spiro-fused polycyclic), or a combination thereof. Unless otherwise specified, aliphatic groups contain 1-20 carbon atoms.

Alkyl: unless otherwise indicated, the alkyl groups described herein are preferably lower alkyl containing from one to eight carbon atoms in the principal chain and up to 20 carbon atoms. They may be linear, branched or cyclic and include methyl, ethyl, propyl, butyl, hexyl and the like.

Amino: unless otherwise indicated, the term "amino" as used herein alone or as part of another group denotes the moiety —NR$^1$R$^2$ wherein R$^1$, and R$^2$ are independently hydrogen, hydrocarbyl, substituted hydrocarbyl or heterocyclo.

Ammonium: unless otherwise indicated, the term "ammonium" as used herein alone or as part of another group denotes the moiety —N$^+$R$^1$R$^2$R$^3$ wherein R$^1$, R$^2$ and R$^3$ are independently hydrogen, hydrocarbyl, substituted hydrocarbyl or heterocyclo.

Amide or Amido: unless otherwise indicated, the "amide" or "amido" moieties represent a group of the formula —CONR$^1$R$^2$ wherein R$^1$ and R$^2$ are as defined in connection with the term "amino." "Substituted amide," for example, refers to a group of the formula —CONR$^1$R$^2$ wherein at least one of R$^1$ and R$^2$ are other than hydrogen. "Unsubstituted amido," for example, refers to a group of the formula —CONR$^1$R$^2$, wherein R$^1$ and R$^2$ are each hydrogen.

Anionic Monomer, Anionic Monomeric Unit or Anionic Repeat Unit: unless otherwise indicated, an "anionic monomer," "anionic monomeric unit" or "anionic repeat unit" is a monomer or monomeric unit bearing an anion or other anionic species, e.g., a group that is present in a negatively charged state or in a non-charged state, but in the non-charged state is capable of becoming negatively charged, e.g., upon removal of an electrophile (e.g., a proton (H+), for example in a pH dependent manner) or a protecting group (e.g., a carboxylic acid ester), or the addition of a nucleophile. In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, sulfonic acids, phosphates, and sulfonamides.

Anionic species or Anionic moiety: unless otherwise indicated, an "Anionic species" or an "Anionic moiety" is a group, residue or molecule that is present in a negatively charged or non-charged state, but in the non-charged state is capable of becoming negatively charged, e.g., upon removal of an electrophile (e.g., a proton (H+), for example in a pH dependent manner) or other protecting group (e.g., a carboxylic acid ester), or the addition of a nucleophile. In certain instances, the group, residue or molecule is substantially negatively charged at an approximately physiological pH but undergoes protonation and becomes substantially neutral at a weakly acidic pH.

Antibiofilm activity: unless otherwise indicated, "antibiofilm activity" may be quantified, for example, using a standard continuous flow assay. In one such assay, samples may be pre-incubated with 50% fetal bovine serum for 18-20 hours at 120 RPM at 37° C. Following preincubation, samples are then exposed to a subculture of bacteria via a modified CDC (mCDC) to make a bacterial suspension of 10$^6$ Cfu/mL in 1×PBS. The reactor is run in batch mode for 2 hours at 37° C. with agitation. Thereafter, the samples are transferred to a fresh reactor a suitable growth media for where flow of the sterile media (8 mL/min) runs 20-23 hours with agitation. In one preferred embodiment, the bacterial strain is *Staphylococcus epidermidis* (*S. epidermidis*, ATCC 35984), and the growth media used is 1:10 Tryptic soy broth (TSB)+0.25 wt % glucose. In an alternate preferred embodiment, the bacterial strain is *Escherichia coli* (*E. coli*, ATCC 25922) and the growth media is M63 media supplemented with 1 mM MgSO$_4$, 0.2% glucose, and 0.5% casamino acids. After incubation, the samples are rinsed five times in 100 mL of 1×PBS to remove bacteria not tightly attached. Then, accumulated bacteria on materials are macroscopically rated for biofilm surface coverage and are removed by sonication in a new solution of PBS and the total number of bacterial cells quantified through dilution plating. Preferably at least a 1, 2, 3 or 4 log reduction in bacterial count is found on the article with the non-fouling polymer layer relative to a reference substrate, that is, the same or an otherwise functionally equivalent substrate lacking the non-fouling polymer layer. An article that has a 1 log reduction in adhered bacteria relative to a reference substrate is said to have antibiofilm activity of 1 log. An article that has a 2 log reduction in adhered bacteria relative to a reference substrate is said to have antibiofilm activity of 2 log, and so forth.

Antimicrobial: unless otherwise indicated, "antimicrobial" refers to molecules and/or compositions that kill (i.e., microbicidal), inhibit the growth of (i.e., microbistatic), and/or prevent fouling by, microorganisms including bacteria, yeast, fungi, mycoplasma, viruses or virus infected cells, and/or protozoa. Antimicrobial activity with respect to bacteria may be quantified, for example, using a standard assay. In one such assay, samples may be pre-incubated with 50% fetal bovine serum for 18-20 hours at 120 RPM at 37° C. Following preincubation, samples are placed in *Staphylococcus aureus* (*S. aureus*, ATCC 25923) which has been diluted from an overnight culture to a planktonic concentration of $1-3\times10^5$ CFU/mL in 1% tryptone soy broth (TSB) diluted in 1× PBS or other suitable media. Samples are incubated with bacteria for 24-26 hrs with agitation (120 rpm) at 37° C. The concentration of TSB or other media can vary with the organism being used. After incubation, the samples are placed in 3 mL PBS for 5 min at 240 RPM at 37° C. to remove bacteria not tightly attached to the material. Then, accumulated bacteria on materials are removed by sonication in a new solution of PBS and the total number of bacterial cells are quantified through dilution plating. Preferably at least a 1, 2, 3 or 4 log reduction in bacterial count occurs relative to colonization on a reference substrate, that is, the same or an otherwise functionally equivalent substrate lacking the non-fouling polymer layer. A surface that has a lower bacterial count on it than the reference substrate may be said to reduce microbial colonization.

Antimicrobial peptide (AmP): unless otherwise indicated, "antimicrobial peptide" (or "AmP") refers to oligopeptides, polypeptides, or peptidomimetics that kill (La, are microbicidal) or inhibit the growth of (i.e., are microbistatic) microorganisms including bacteria, yeast, fungi, mycoplasma, viruses or virus infected cells, and/or protozoa.

Anti-thrombogenic: unless otherwise indicated, "anti-thrombogenic" refers to the ability of a composition to resist thrombus formation. Anti-thrombogenic activity can be evaluated using an ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for an article containing a lumen by connecting the two ports of the article through a 2nd peristaltic pump. The size of tubing into which the article is placed and speed of the blood flow may be adjusted based on the size of the article being tested.

Aryl: unless otherwise indicated, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

Attached: unless otherwise indicated, two moieties or compounds are "attached" if they are held together by any interaction including, by way of example, one or more covalent bonds, one or more non-covalent interactions (e.g., hydrogen bonds, ionic bonds, static forces, van der Waals interactions, combinations thereof, or the like), or a combination thereof.

Bioactive Agent/Active Agent/Biomolecule: unless otherwise indicated, "bioactive agent" or "active agent" or "biomolecule," used herein synonymously, refers to any organic or inorganic therapeutic, prophylactic or diagnostic agent that actively or passively influences a biological system. For example, a bioactive agent can be an amino acid, antimicrobial peptide, immunoglobulin, an activating, signaling or signal amplifying molecule, including, but not limited to, a protein kinase, a cytokine, a chemokine, an interferon, tumor necrosis factor, growth factor, growth factor inhibitor, hormone, enzyme, receptor-targeting ligand, gene silencing agent, ambisense, antisense, an RNA, a living cell, cohesin, laminin, fibronectin, fibrinogen, osteocalcin, osteopontin, or osteoprotegerin. Bioactive agents can be aptamers, proteins, glycoproteins, peptides, oligliopeptides, polypeptides, polymers, inorganic compounds, organometallic compounds, organic compounds or any synthetic or natural, chemical or biological compound.

Biocompatibility: unless otherwise indicated, "biocompatibility" is the ability of a material to perform with an appropriate host response in a specific situation. This can be evaluated using International Standard ISO 10993. Biocompatible compositions described herein are preferably substantially non-toxic.

Biological fluids: unless otherwise indicated, "biological fluids" are fluids produced by organisms containing proteins and/or cells, as well as fluids and excretions from microbes. This includes, but is not limited to, blood, saliva, urine, cerebrospinal fluid, tears, semen, lymph, ascites, sputum, bone marrow, synovial fluid, aqueous humor, cerumen, broncheoalveolar lavage fluid, prostatic fluid, cowper's fluid or pre-ejaculatory fluid, sweat, fecal matter, cyst fluid, pleural and peritoneal fluid, chyme, chyle, bile, intestinal fluid, pus, sebum, vomit, mucosal secretion, stool water, pancreatic juice, lavage fluids from sinus cavities, bronchopulmonary aspirates, or any derivative thereof (e.g., serum, plasma).

Block Copolymer: unless otherwise indicated, a "block copolymer" comprises two or more homopolymer or copolymer subunits linked by covalent bonds. Block copolymers with two or three distinct blocks are called diblock copolymers and triblock copolymers, respectively. A schematic generalization of a diblock copolymer is represented by the formula $[A_aB_bC_c \ldots ]_m\text{-}[X_xY_yZ_z \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: X-X-Y-Z-X-Y-Y-Z-Y-Z-Z-Z .... A non-limiting, exemplary alternating random configuration may have the non-limiting form: X-Y-X-Z-Y-X-Y-Z-Y-X-Z . . . , and an exemplary regular alternating configuration may have the non-limiting form: X-Y-Z-X-Y-Z-X-Y-Z . . . . An exemplary regular block configuration may have the following non-limiting configuration: . . . X-X-X-Y-Y-Y-Z-Z-Z-X-X-X . . . , while an exemplary random block configuration may have the non-limiting configuration: . . . X-X-X-Z-Z-X-X-Y-Y-Y-Y-Z-Z-Z-X-X-Z-Z-Z- . . . . In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming a micelle described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

Branched: unless otherwise indicated, "branched" refers to a polymer structure in which a polymer chain divides into two or more polymer chains.

Brushes/Polymer Brushes: unless otherwise indicated, "brushes" or "polymer brushes" are used herein synonymously and refer to polymer chains that are bound to a surface generally through a single point of attachment using graft-from techniques. The polymers can be end-grafted (attached via a terminal group) or attached via a side chain or a position in the polymer chain other than a terminal position. The polymers can be linear or branched. For example, the polymer chains described herein can contain a plurality of side chains that contain zwitterionic groups. The side chains can consist of a single non-fouling moiety or monomer and/or a non-fouling oligomer (e.g., 2-10 monomeric residues) or polymer (e.g., >10 monomeric residues).

Carboxyammonium: unless otherwise indicated, a "carboxyammonium" moiety is a zwitterionic moiety comprising carboxylate and ammonium functionality and includes, for example, carboxyammonium monomers, carboxyammonium oligomers, carboxyammonium polymers, carboxyammonium repeat units, and other carboxyammonium-containing materials. Carboxybetaine monomers, oligomers, polymers, repeat units and other carboxybetaine materials are exemplary carboxyammonium moieties.

Cationic Monomer, Cationic Monomeric Unit or Cationic Repeat Unit: unless otherwise indicated, a "cationic monomer," "cationic monomeric unit" or "cationic repeat unit" is a monomer or a monomeric or repeat unit (the terms "monomeric unit" and "repeat unit" being used interchangeably) bearing a cation or other cationic species, e.g., a moiety capable of having a positive charge upon addition of an electrophile (e.g., a proton (H+) or an alkyl cation, for example in a pH dependent manner) or removal of a protecting group or a nucleophile).

Cationic species or Cationic Moiety: unless otherwise indicated, a "Cationic species" or a "Cationic Moiety" is a group, residue or molecule that is present in a positively charged or non-charged state, but in the non charged state is capable of becoming positively charged, e.g., upon addition of an electrophile (e.g., a proton (H+), for example in a pH dependent manner) or removal of a protecting group or a nucleophile. In certain instances, the group, residue or molecule is permanently charged, e.g., comprises a quaternary nitrogen atom.

Coating: unless otherwise indicated, "coating" refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate.

Complex Media: unless otherwise indicated, "complex media" refers to biological fluids or solutions containing proteins or digests of biological materials. Examples include, but are not limited to, cation-adjusted Mueller Hinton broth, tryptic soy broth, brain heart infusion, or any number of complex media, as well as any biological fluid.

Copolymer: unless otherwise indicated, "copolymer" refers to a polymer derived from two, three or more monomeric species and includes alternating copolymers, periodic copolymers, random copolymers, statistical copolymers and block copolymers.

Cysteine: unless otherwise indicated, "cysteine" refers to the amino acid cysteine or a synthetic analogue thereof, wherein the analogue contains a free sulfhydryl group.

Degradation Products: unless otherwise indicated, "degradation products" are atoms, radicals, cations, anions, or molecules other than water formed as the result of hydrolytic, oxidative, enzymatic, or other chemical processes.

Dry Thickness: unless otherwise indicated, "Dry Thickness," as used herein in connection with a polymer layer, shall mean the thickness of the polymer layer using a scanning electron microscope (SEM). To measure dry thickness, the sample is freeze fractured for imaging by being submerged in liquid nitrogen then cracked with an ultra microtome blade. For metal substrates, they may be scored with a notch before a primer or the non-fouling polymer is applied to make freeze fracturing easier. The freeze fracturing should break the article at a plane approximately orthogonal to the polymer modified surface in order to measure the thickness of the polymer layer normal to the substrate. The samples are sputter coated in gold for 90 seconds using a sputter coater and then imaged under high vacuum at 5 kV using an SE2 detector under a Field Emission Scanning Electron Microscope (SEM). Exemplary microtome blades include the Leica Ultracut UCT Ultramicrotome, exemplary sputter coaters include the Cressington 208HR, exemplary SEMs include the Supra55VP FESEM, Zeiss. Dry thickness may be approximated by analyzing intensity of chemical signals in the grafted polymer, for instance, through the use of ATR-FTIR.

Fibrinogen Adsorption Assay: unless otherwise indicated, a "Fibrinogen Adsorption Assay" is an assay used to assess the capacity of a surface for fibrinogen. In the assay, test samples are placed in a suitable sized container, which may be a 96-well manifold, microcentrifuge tube, or other container. The volumes in the following are appropriate for a deep 96-well plate, but may be scaled to properly cover a device being tested. The samples are sterilized with 70% ethanol solution for thirty minutes and the test groups run with an n per run of 3-4. The sample container is blocked with 20 mg/mL Bovine Serum Albumin (BSA) in 1×PBS for 1 hour at 4° C., followed by three rinses with 1×PBS before samples are added. The sample is exposed to a solution containing 70 µg/mL unlabeled human fibrinogen, 1.4 µg/mL I-125 radiolabeled human fibrinogen, 35-55 µg/mL BSA in water, optionally tri-sodium citrate, and optionally sodium chloride. The BSA is a common agent co-lyophilized with the radiolabeled fibrinogen. Optionally, the BSA and radiolabeled fibrinogen may have been dissolved from a lyophilized form that contains tri-sodium citrate and sodium chloride. The samples are incubated for one hour at 37° C. on an orbital shaker at 150 RPM. The test solution is then removed and four 1-minute rinses with a 10 mM NaI and one 1-minute rinse with 1×PBS is performed. The samples are loaded into a gamma counter. The counter measures the radioactivity in I-125 counts per minute for each sample and this data is used to calculate the absolute fibrinogen adsorption or a percent reduction of the non-fouling polymer layer samples versus a reference substrate, that is, the same or an otherwise functionally equivalent substrate lacking the non-fouling polymer layer. The percent reduction is equal to: (1−non-fouling sample CPM/Average CPM of the reference substrate)*100%.

Global Average Dry Thickness: unless otherwise indicated, "Global Average Dry Thickness," as used herein in connection with a polymer layer, shall mean the mean calculated by averaging the Local Average Dry Thickness of at least 3, and preferably at least 5, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average Dry Thickness is found by calculating the standard deviation of the Local Average Dry Thickness across at least 5, and preferably at least 10, representative locations spaced approximately evenly across the portion of the article carrying the polymer layer.

Global Average Humidified Thickness: unless otherwise indicated, "Global Average Humidified Thickness," as used herein in connection with a polymer layer, shall mean the mean calculated by averaging the Local Average Humidified Thickness of at least 3, and preferably at least 5, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average Humidified Thickness is found by calculating the standard deviation of the Local Average Humidified Thickness across at least 5, and preferably at least 10, representative locations spaced approximately evenly across the portion of the article carrying the polymer layer.

Global Average $R_{rms}$ Surface Roughness: unless otherwise indicated, "Global Average $R_{rms}$ Surface Roughness," as used herein in connection with a polymer layer, shall mean the mean calculated by averaging the $R_{rms}$ surface roughness of at least 5, and preferably at least 10, representative locations spaced approximately evenly across the portion of the article carrying the polymer layer. For example, if a polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The standard deviation of the Global Average $R_{rms}$ Surface Rroughness is found by calculating the standard deviation of the Local Average $R_{rms}$ Surface Roughness across at least 5, and preferably at least 10, representative locations spaced approximately evenly across the portion of the article carrying the polymer layer.

Graft: unless otherwise indicated, the term "graft," as used herein in connection with a polymer, means the modification of the surface of a material with a polymer by a "graft-from", "graft-through", or a "graft-to" approach, or a combination thereof to form a grafted polymer.

Graft-from method: unless otherwise indicated, the term "graft-from," as used herein in connection with a method for the modification of a material with a polymer, shall mean the in situ polymerization and growth of a polymer at the surface of, or within a material.

Graft-from polymer: unless otherwise indicated, the term "graft-from polymer," as used herein, shall mean a polymer formed by a graft-from method.

Graft-through method: unless otherwise indicated, the term "graft-through," as used herein in connection with a method for the modification of a material with a polymer, shall mean the in situ polymerization of monomers in the neighborhood of the material that may polymerize through functional groups presented from the material surface. For example, the material may have vinyl groups presented from the surface through which polymerization occurs.

Graft-through polymer: unless otherwise indicated, the term "graft-through polymer," as used herein, shall mean a polymer formed by a graft-through method.

Graft-to method: unless otherwise indicated, the term "graft-to," as used herein in connection with a method for the modification of a material with a polymer shall mean the modification of the surface of a material with a presynthesized polymer Graft-to polymer: unless otherwise indicated, the term "graft-to polymer," as used herein, shall mean a grafted polymer formed by a graft-to method.

Heteroalkyl: unless otherwise indicated, the term "heteroalkyl" means an alkyl group wherein at least one of the backbone carbon atoms is replaced with a heteroatom.

Heteroaryl: unless otherwise indicated, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heteroatom: unless otherwise indicated, the term "heteroatom" means an atom other than hydrogen or carbon, such as a chlorine, iodine, bromine, oxygen, sulfur, nitrogen, phosphorus, boron, arsenic, selenium or silicon atom.

Heterocyclo: unless otherwise indicated, the terms "heterocyclo" and "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heterohydrocarbyl: unless otherwise indicated, the term "heterohydrocarbyl" means a hydrocarbyl group wherein at least one of the chain carbon atoms is replaced with a heteroatom.

Humidified Thickness: unless otherwise indicated, "humidified thickness," as used herein in connection with a polymer layer, shall mean the thickness of the polymer layer using an environmental scanning electron microscope (ESEM and approximately 26% relative humidity). To measure humidified thickness, the sample is freeze fractured for imaging by being submerged in liquid nitrogen then cracked with an ultra microtome blade. The freeze fracturing should break the article at a plane orthogonal to the polymer modified surface in order to measure the thickness of the polymer layer normal to the substrate. After fracturing, the samples are soaked in water for at least one hour and then submerged in liquid nitrogen and fixed to a cold stage at $-8°$ C. to $-12°$ C. The samples are then imaged using a VPSE detector at the highest resolvable humidity (approximately 26% or 81 Pa) under a Scanning Electron Microscope (SEM) with an Environmental Scanning Electron Microscope (ESEM). Exemplary microtome blades include the Leica Ultracut UCT Ultramicrotome, exemplary SEMs include the Supra55VP FESEM, Zeiss, and exemplary E-SEMs include the Zeiss EVO 55.

Hydrocarbon or Hydrocarbyl: unless otherwise indicated, the terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms Hydrophilic: unless otherwise indicated, "hydrophilic" refers to solvents, molecules, compounds, polymers, mixtures, materials, or functional groups which have an affinity for water. Such materials typically include one or more hydrophilic functional groups, such as hydroxyl, zwitterionic, carboxy, amino, amide, phosphate, sulfonyl, hydrogen bond forming, and/or ether groups.

Hydrophobic: unless otherwise indicated, "hydrophobic" refers to solvents, molecules, compounds, polymers, mixtures, materials, or functional groups that are repelled by water. Such materials typically contain non-polar functional groups.

Immobilization/Immobilized: unless otherwise indicated, "immobilization" or "immobilized" refers to a material or bioactive agent that is covalently or non-covalently attached directly or indirectly to a substrate. "Co-immobilization" refers to immobilization of two or more agents.

Initiator: unless otherwise indicated, "initiator" refers to a substance or a combination of substances that can produce a radical or other species under relatively mild conditions and promote polymerization reactions. For example, redox pairs as described elsewhere herein may be an initiator.

Local Average Dry Thickness: unless otherwise indicated, "Local Average Dry Thickness" is the mean Dry Thickness calculated by averaging Dry Thickness measurements of at least 3, and preferably at least 5, representative locations spaced approximately evenly across a cross section of the article that spans approximately 10-40 micrometers. The standard deviation of the Local Average Dry Thickness is determined by calculating the standard deviation of the Dry Thickness across at least 5, and more preferably at least 10, representative locations spaced approximately evenly across a cross section of article that spans approximately 10-40 micrometers.

Local Average Humidified Thickness: unless otherwise indicated, "Local Average Humidified Thickness" is the mean Humidified Thickness calculated by averaging Humidified Thickness measurements of at least 3, and preferably at least 5, representative locations spaced approximately evenly across a cross section of the article that spans approximately 10-40 micrometers. The standard deviation of the Local Average Humidified Thickness may be determined by calculating the standard deviation of the Humidified Thickness across of at least 5, and preferably at least 10, representative locations spaced approximately evenly across a cross section of article that spans approximately 10-40 micrometers.

Membrane-Targeting Antimicrobial Agent: unless otherwise indicated, "membrane-targeting antimicrobial agent" refers to any antimicrobial agent that retains its bactericidal or bacteriostatic activity when immobilized on a substrate and can therefore be used to create an immobilized antimicrobial surface. In one embodiment, the membrane-targeting antimicrobial agent is an antimicrobial peptide, and in another embodiment it is a quaternary ammonium compound or polymer.

Non-Degradable: unless otherwise indicated, "non-degradable" refers to material compositions that do not react significantly within a biological environment either hydrolytically, reductively, enzymatically or oxidatively to cleave into smaller or simpler components.

Non-Fouling Composition/Non-Fouling Material/Non-Fouling Polymer/Non-Fouling Polymer Layer: unless otherwise indicated, a "non-fouling composition" or "non-fouling material" or "non-fouling polymer" or "Non-fouling polymer layer" as used interchangeably herein, is a composition that provides or increases the protein resistance of a surface of an article to which the composition is attached. For example, when attached to a substrate such a composition may resist the adhesion of proteins, including blood proteins, plasma, cells, tissue and/or microbes to the substrate relative to the amount of adhesion to a reference substrate, that is, the same or an otherwise functionally equivalent substrate lacking the composition. Preferably, a substrate surface will be substantially non-fouling in the presence of human blood. Preferably the amount of adhesion will be decreased 20%, 30%, 40%, 50%, 60%, 70%, 80%, or more, for example, 85%, 90%, 95%, 99%, 99.5%, 99.9%, or more, relative to the reference substrate. One particularly preferred measure of the non-fouling character or protein resistance of a surface is the amount of fibrinogen adsorbed in a Fibrinogen Adsorption Assay as described herein. Preferably, the amount of adsorbed fibrinogen using the Fibrinogen Adsorption Assay described herein is <125 $ng/cm^2$, <90 $ng/cm^2$, <70 $ng/cm^2$, <50 $ng/cm^2$, <30 $ng/cm^2$, <20 $ng/cm^2$, <15 $ng/cm^2$, <12 $ng/cm^2$, <10 $ng/cm^2$, <8 $ng/cm^2$, <6 $ng/cm^2$, <4 $ng/cm^2$, <2 $ng/cm^2$, <1 $ng/cm^2$, <0.5 $ng/cm^2$, or <0.25 $ng/cm^2$.

Non-Naturally Occurring Amino Acid: unless otherwise indicated, "non-naturally occurring amino acid" refers to any amino acid that is not found in nature. Non-natural amino acids include any D-amino acids, amino acids with side chains that are not found in nature, and peptidomimetics. Examples of peptidomimetics include, but are not limited to, b-peptides, g-peptides, and d-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination. All of the amino acids in the human body, except glycine, exist as the D and L forms. Nearly all of the amino acids occurring in nature are the L-forms. D-forms of the amino acids are not found in the proteins of higher organisms, but are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction. Non-naturally occurring amino acids also include residues, which have side chains that resist non-specific protein adsorption, which may be designed to enhance the presentation of the antimicrobial peptide in biological fluids, and/or polymerizable side chains, which enable the synthesis of polymer brushes using the non-natural amino acid residues within the peptides as monomeric units.

Polymer: unless otherwise indicated, "polymer" includes natural and synthetic, homopolymers and copolymers comprising multiple repeat units and, unless otherwise indicated, may be linear, branched, or dendritic. Examples of copolymers include, but are not limited to, random copolymers and block copolymers, smart polymers, temperature responsive (e.g., NIPAM), and pH responsive (e.g., pyridyl based) polymers.

Polypeptide/Peptide/Oligopeptide: unless otherwise indicated, "polypeptide," "peptide," and "oligopeptide" encompass organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e., production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

Quaternary Nitrogen: unless otherwise indicated, "quaternary nitrogen," as used herein, refers to a nitrogen atom that is a member of a quaternary ammonium cation.

$R_{rms}$ Surface Roughness: unless otherwise indicated, "$R_{rms}$ Surface Roughness" refers to root mean squared roughness of a surface, which measures the vertical deviations of a real surface from its ideal form. The roughness refers to surface micro-roughness which may be different than measurements of large scale surface variations. Preferably, this may be measured using atomic force microscopy (MFP-3D, Aslyum) across a field of approximately 1-30 μm by 1-30 μm, preferably 20 μm by 20 μm. The sample is washed with purified water to remove surface salts and then air dried. Standard silicon cantilever (Olympus AC160TS, spring constant 42 N/m) is employed for the measurement with an AC/Tapping mode. The $R_{rms}$ surface roughness is calculated by the software (IGOR Pro) attached with the AFM machine. Alternatively the roughness can be measured using a stylus profilometer. For example, the sample surface roughness can be measured by a Tencor P-16+ profilometer with a 60 degree, 2 μm diamond tip stylus. Preferably, an 800 μm scan length is chosen with 20 μm/second scan rate, 50 Hz scan frequency, and 2 μg loading force. At least three different sites are measured for the same sample, and the surface roughness is averaged from at least three samples. Alternatively, the $R_{rms}$ surface roughness can be measured preferably by non-contact methods, including using optical profilometers. For example, the sample surface roughness is measured by a optical profilometer (Zeta Z20 or Olympus Lext OLS4000). Preferably a 3-D image is taken by the optical profilometer under a 50× objective lens, and the sample's surface roughness is then measured along at least three different lines cross the image. At least three different spots are measured and the surface roughness is averaged from at least three samples. In a preferred example an Olympus LEXT OLS4000 3D Laser Measuring Microscope is employed for roughness measurements and 3D imaging. A LEXT microscope utilizes low wavelength optical technology with a 408 nm laser in combination with confocal scanning can be used for the measurement. Samples to be measured are mounted on a glass slide by double-sided tape. Digital 3-D images are taken with the Olympus LEXT OLS4000 laser confocal microscope ("LEXT") under an Olympus MPLAPON 50× objective lens. The digital images taken in this way have a 256×256 μm field area. The Z-direction repeatability for this LEXT machine has been certified by Olympus to be less than 0.012 μm. To measure the roughness, at least three images have been taken from each sample and the $R_{rms}$ roughness is calculated by using a 9 μm cut-off length.

Solvent Extractable Polymerization Initiator: unless otherwise indicated, "Solvent Extractable Polymerization Initiator" refers to any compound capable of starting radical polymerization that has been incorporated within the article, wherein either the initiator or its degradation products may be extracted from the article using a suitable solvent. In general, extractions can use nonpolar or polar solvents. For example, extraction solvents such as water, acetone or ethanol; and/or other extraction solvents in which the solubility of the initiator and/or its degradation products is at least 1 mg/L. The extraction should be carried out for a sufficient time such that the change in concentration of the extract is not increasing more than 5% per hour. Alternatively, extraction until the amount of extracted material in a subsequent extraction is less than 10% of that detected in the initial extraction, or until there is no analytically significant increase in the cumulative extracted material levels detected. Extraction conditions include: 37° C. for 72 h; 50° C. for 72 h; 70° C. for 24 h; 121° C. for 1 h. Extraction ratio includes 6 $cm^2$/mL surface area/volume and/or 0.2 g sample/mL. In some instances, complete dissolution of the substrate may be appropriate. Materials shall be cut into small pieces before extraction to enhance submersion in the extract media, for example, for polymeric substrates approximately 10 mm×50 mm or 5 mm×25 mm are appropriate. The instrumentation used includes high-performance liquid chromatography-photo-diode array detection-mass spectrometry (HPLC-PDA-MS) for organics analysis; gas chromatography-mass spectrometry (GC-MS) for organics analysis; inductively coupled plasma-optical emission spectroscopy or mass spectrometry (ICP-OES or ICP-MS) for metals analysis; and sometimes ion chromatography (IC) for inorganics and ion analysis. Sometimes more advanced MS detectors such as time-of-flight (TOF) are used to obtain accurate mass information. Hexane and alcohol extractions are analyzed by GC-MS. Water and alcohol extractions are analyzed by HPLC. The initiator or its degradation products may be quantified and/or detected in the substrate or grafted polymer by the previously described methods. These include FTIR-ATR, electron spectroscopy for chemical analysis (ESCA, also called X-ray photoelectron spectroscopy, XPS), Secondary Ion Mass Spectrometry (SIMS), and surface-enhanced Raman spectroscopy (SERS). For example, peroxide may be detected spectrophotometrically using any of the following three methods: the iodide method (oxidation of sodium iodide by peroxides in the presence of ferric chloride), the DPPH method (treatment with 1,1-diphenyl-2-picrylhydrazyl, a radical scavenger, to decompose the peroxides), or the peroxidase method (reduction with glutathione, catalyzed by glutathione peroxidase, followed by measuring the coupled oxidation of NADPH in the presence of glutathione reductase). See, for example, Fujimoto et al., Journal of Polymer Science Part A: Polymer Chemistry, Vol. 31, 1035-1043 (1993).

Stable: unless otherwise indicated, "stable," as used herein in reference to a material, means that the material retains functionality over extended periods of time. In one embodiment, the referenced material retains at least 90% of a referenced activity (or property) for at least 30 days at 37° C. in at least one of phosphate buffered saline containing protein, media, or serum, or in vivo. In one embodiment, the reference material retains at least 80% of a referenced activity (or property) for at least 90 days at 37° C. in at least one of phosphate buffered saline containing protein, media, or serum, or in vivo. In one embodiment, the referenced material retains at least 90% of the referenced activity (or property) for at least 30 days at 37° C. and at least 80% of the referenced activity (or property) for at least 90 days at 37° C. The referenced activity or property may include surface contact angle, non-fouling, anti-thrombogenic, and/or antimicrobial activity.

Static Contact Angle: unless otherwise indicated, "Static Contact Angle" is the angle at which a water/vapor interface meets a substrate surface at or near equilibrium conditions. The contact angle is measured by first soaking the samples with pure ethanol for 5 minutes and washing with PBS three times. The samples are then soaked within PBS (150 mM, pH 7.4) for 24 hours and washed three times with purified water. Then the samples are dried under a flow of air for 5 min before testing. A drop of purified water (e.g., 1 μL) is deposited on the test surface, the shape of the droplet is photographed by a microscope with a CCD camera using a video contact angle system (e.g., VCA 2000, AST Inc.), and the contact angle is then determined (using, for example, a VCA Optima XE). The size of the water droplet used to determine the contact angle may vary depending upon the substrate type and composition. For a 5 French device, for instance, an 0.1 μL drop of purified water may be used.

Substantially Hemocompatible: unless otherwise indicated, "substantially hemocompatible" means that the composition is substantially non-hemolytic, in addition to being non-thrombogenic and non-immunogenic, as tested by appropriately selected assays for thrombosis, coagulation, and complement activation as described in ISO 10993-4.

Substantially Non-Cytotoxic: unless otherwise indicated, "substantially non-cytotoxic" refers to a composition that does not substantially change the metabolism, proliferation, or viability of mammalian cells that contact the surface of the composition. These may be quantified by the International Standard ISO 10993-5 which defines three main tests to assess the cytotoxicity of materials including the extract test, the direct contact test and the indirect contact test.

Substantially Non-Hemolytic Surface: unless otherwise indicated, "substantially non-hemolytic surface" means that the composition does not lyse 50%, preferably 20%, more preferably 10%, even more preferably 5%, most preferably 1%, of human red blood cells when the following assay is applied: a stock of 10% washed pooled red blood cells (Rockland Immunochemicals Inc, Gilbertsville, Pa.) is diluted to 0.25% with a hemolysis buffer of 150 mM NaCl and 10 mM Tris at pH 7.0. A 0.5 cm$^2$ antimicrobial sample is incubated with 0.75 mL of 0.25% red blood cell suspension for 1 hour at 37° C. The solid sample is removed and cells are spun down at 6000 g, the supernatant is removed, and the OD414 measured on a spectrophotometer. Total hemolysis is defined by diluting 10% of washed pooled red blood cells to 0.25% in sterile deionized (DI) water and incubating for 1 hour at 37° C., and 0% hemolysis is defined using a suspension of 0.25% red blood cells in hemolysis buffer without a solid sample.

Substantially Non-Toxic: unless otherwise indicated, "substantially non-toxic" means a surface that is substantially hemocompatible and substantially non-cytotoxic.

Substituted/Optionally Substituted: unless otherwise indicated, the term "substituted" and "optionally substituted" means that the referenced group is or may be substituted with one or more additional suitable group(s), which may be individually and independently selected, for example, from acetals, acyl, acyloxy, alkenoxy, alkoxy, alkylthio, alkynoxy, amido, amino, aryl, aryloxy, arylthio, azido, carbonyl, carboxamido, carboxyl, cyano, esters, ethers, hydrocarbyl, substituted hydrocarbyl, heterohydrocarbyl, substituted heterohydroalkyl, cycloalkyl, halogen, heteroalicyclic, heteroaryl, hydroxy, isocyanato, isothiocyanato, ketals, keto, mercapto, nitro, perhaloalkyl, silyl, sulfamoyl, sulfate, sulfhydryl, sulfonamido, sulfonate, sulfonyl, sulfoxido, thiocarbonyl, thiocyanato, thiol, and/or the protected derivatives thereof. It will be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Substrate: unless otherwise indicated, "substrate" refers to the material from which a non-fouling polymer is grafted.

Sulfoammonium: unless otherwise indicated, a "sulfoammonium" moiety is a zwitterionic moiety comprising sulfate and ammonium functionality and includes, for example, sulfoammonium monomers, sulfoammonium oligomers, sulfoammonium polymers, sulfoammonium repeat units, and other sulfoammonium-containing materials. Sulfobetaine monomers, oligomers, polymers, repeat units, and other sulfobetaine materials are exemplary sulfoammonium moieties.

Tether/Tethering Agent/Linker: unless otherwise indicated, "tether" or "tethering agent" or "linker," as used herein synonymously, refers to any molecule, or set of molecules, or polymer used to covalently or non-covalently immobilize one or more non-fouling materials, one or more bioactive agents, or combinations thereof on a material where the molecule remains as part of the final chemical composition. The tether can be either linear or branched with one or more sites for immobilizing bioactive agents. The tether can be any length. However, in one embodiment, the tether is greater than 3 angstroms in length. The tether may be non-fouling, such as a monomer, oligomer, or polymer or a non-fouling non-zwitterionic material. The tether may be immobilized directly on the substrate or on a polymer, either of which may be non-fouling.

Undercoating Layer: unless otherwise indicated, "undercoating layer" refers to any coating, or combination of coatings, incorporated into a substrate from which a non-fouling polymer is grafted.

Zwitterion/Zwitterionic Material: unless otherwise indicated, "zwitterion" or "zwitterionic material" refers to a macromolecule, material, or moiety possessing both cationic and anionic groups. In most cases, these charged groups are balanced, resulting in a material with zero net charge.

Zwitterionic Polymers: unless otherwise indicated, "zwitterionic polymers" may be homopolymers or copolymers and include both polyampholytes (e.g., polymers with the charged groups on different monomer units) and polybetaine (polymers with the anionic and cationic groups on the same monomer unit). Exemplary zwitterionic polymers include alternating copolymers, statistical copolymers, random copolymers and block copolymers of two, three or more monomers.

DETAILED DESCRIPTION OF THE INVENTION

Among the various aspects of the present invention may be noted the provision of articles, such as medical devices, having a grafted polymer. In general, therefore, the article comprises a substrate, a polymeric primer on at least a portion of a substrate, and a polymeric material grafted to or from at least a portion of the polymeric primer. Advantageously, the polymeric primer contains functional groups to which a presynthesized polymer may be grafted, or from which a polymer may be grown, in situ. Because the polymer is grafted to or from the polymeric primer, the number of sites for grafting the polymeric material may be tuned by controlling the concentration of corresponding functional groups in the polymeric primer. Additionally, a high density of functional groups are present in the polymeric primer, not only at the surface, but throughout the primer. In one embodiment, the primer is a relative hydrophobic polymer, which may attach to the substrate through hydrophobic interactions. The grafted polymers is hydrophilic and difference between the static contact angle of the polymeric primer, prior to the attachment of the grafted polymer, and the modified surface is at least 5 degrees.

Medical devices and other articles comprise any of a wide range of materials. Certain of these materials, by virtue of their intrinsic characteristics, exhibit a greater resistance to protein adsorption and cell/microorganism adhesion; for example, hydrophilic materials tend to exhibit less protein adsorption than hydrophobic materials. In addition, methods of manufacture can greatly affect the surface characteristics of such materials; for example, manufacturing methods may affect the porosity of a material, its roughness (micro-roughness and macro-roughness), incorporation of foreign-body inclusions that project from the surface of the material, and similar surface characteristics. Each of these, and other factors, may increase the degree of fouling that occurs at the article surface, independent of any further surface modification. In addition to fouling caused by deposition of proteins, mineralization and attachment of mammalian cells, or bacteria, often occurs. In the clinical setting, deposition of biological materials leading to thrombosis and bacterial biofilm are particularly undesirable.

By coating such articles with a polymer primer and grafting a polymeric material, preferably a non-fouling polymer, to or from the polymeric primer, the articles may be provided with a surface modification which disfavors protein adsorption and/or cell/microorganism adhesion and which may, in addition, conceal or otherwise alter the sites in a substrate that favor the adhesion of cells, bacteria or other microorganisms. Thus, for example, and relative to the (unmodified) surface of the article, the polymeric primer and grafted polymer may cover, or even partially or completely fill, scratches, pinholes, voids or other defects in the surface of the article that could potentially otherwise serve as a site for a performance failure. By way of further example, grafted polymers and polymeric primers having a combined thickness that is at least as great as the surface roughness of the (unmodified) surface of the article, that are relatively uniform, that are sufficiently dense, and/or are significantly hydrophilic can significantly increase a material's resistance to protein adsorption and/or cell/microorganism adhesion.

In one aspect of the present invention, a non-fouling layer is applied onto only a portion or portions of a substrate or object, including in a 2 or 3-dimensional pattern or patterns at discrete locations on a substrate or object. In some embodiments the non-fouling layer is applied onto a substrate or object in such a way as to have discrete and/or blended geometrical features and/or designs at many scales ranging from nanometers to micrometers to millimeters. Preferred embodiments include controllably forming a discrete non-fouling feature(s) involves the selective masking or blocking of the desired portions of the substrate from imbibing and/or application of the initiator and/or from the graft polymerization. In one embodiment a portion of the substrate article is masked during initiator application. In one preferred embodiment a portion of the substrate article is masked during polymerization. The masking technique may be applied to any of the substrates described herein, including metals, ceramics, glasses, polymers, biological tissues, living or dead, woven and non-woven fibers, semi-metals such as silicon.

Among the various aspects of the present invention is controllably placing a non-fouling polymer at discrete locations on a substrate or object by several means. For locations, patterns, geometric features/designs greater than or equal to millimeter scale controllably placing a non-fouling polymer may be accomplished by physically masking areas where the non-fouling polymer will not form, for example, by using techniques such as applying tape, screens, resists, or other blocking materials that inhibit access of the polymerization solution to the substrate or object surface, therefore inhibiting polymer formation. For locations, patterns, geometric features/designs less than millimeter scale controllably placing a non-fouling polymer may be accomplished by physically masking areas where the non-fouling polymer will not form using techniques such as photolithographic procedures (such as stereolithography, laser-chemical three-dimensional writing, and modular assembly), microcontact printing, or microstamping of blocking materials that inhibit access of the polymerization solution to the substrate or object surface, therefore inhibiting polymer formation. In addition, masking materials can be applied at any scale by means of digital application methods such as spray jet, valve jet, and inkjet printing methods.

In some embodiments, masking during polymerization permits the ability to apply a mix of different polymers over different areas of a substrate or object. By means of selectively removing portions or types of masking materials or agents from discrete locations followed by subsequent polymerization steps with different monomers or monomer mixtures a non-fouling surface can be constructed consisting of any number of different polymers with similar or different non-fouling, dimensional, mechanical, physical, and/or chemical properties.

One embodiment includes techniques that remove primed portions and/or non-fouling polymer portions from the substrate or object in a controlled fashion and thus create locations, patterns, geometric features/designs of non-fouling polymer at any scale, including laser ablation, abrasive media stream/spray, or direct contact physical abrasion/scraping.

The presence or absence of a non-fouling polymer in a controlled design/pattern can be used to control and/or modulate the interaction, adsorption, deasorption, of proteins and other biomolecules as well as control and/or modulate, interaction, adsorption, deasorption, proliferation of cells (eukaryotes, prokaryotes). Structures which may influence these processes including creating columns perpendicular to the article surface, channels along the surface, or a number of other geometrical patterns. The feature size or space between features may be smaller, approximately the same size as, or larger than the protein or cell being influenced. Structures that reduce adsorption may be synergistic with non-fouling polymer surface modifications to enhance non-fouling ability.

Independent of any theory, articles of the present invention having a modified surface comprising a grafted polymer exhibit low fibrinogen adsorption in a fibrinogen adsorption assay. In general, the modified surface exhibits a fibrinogen adsorption of less than 125 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In one embodiment, the modified surface has a fibrinogen adsorption of less than about 90 ng/cm$^2$ in a fibrinogen binding assay in which the modified surface is incubated for 60 minutes at 37° C. in a solution containing 70 µg/mL fibrinogen derived from human plasma and 1.4 µg/mL I-125 radiolabeled fibrinogen. In another embodiment, the modified surface has a fibrinogen adsorption of less than 75 ng/cm$^2$ in a fibrinogen adsorption assay in which samples are incubated for 60 minutes at 37° C. in 70 µg/ml fibrinogen derived from human plasma, and the amount of adsorbed fibrinogen is determined using a standard protocol, preferably by using radiolabeled fibrinogen. Preferably, the modified surface exhibits a fibrinogen adsorption of less than 30 ng/cm$^2$ in such an assay. Preferably, in certain embodiments the modified surface exhibits a fibrinogen adsorption of less than 50 ng/cm$^2$ in such an assay. More preferably, in certain embodiments the modified surface exhibits a fibrinogen adsorption of less than 20 ng/cm$^2$ in such an assay. Still more preferably, in certain embodiments the modified surface exhibits a fibrinogen adsorption of less than 15 ng/cm$^2$ in such an assay. In some embodiments, the modified surface exhibits a fibrinogen adsorption of less than 12 ng/cm$^2$ in such an assay. In some embodiments, the modified surface exhibits a fibrinogen adsorption of less than 10 ng/cm$^2$ in such an assay. In some embodiments, the modified surface exhibits a fibrinogen adsorption of less than 8 ng/cm$^2$ in such an assay. In some embodiments, the modified surface exhibits a fibrinogen adsorption of less than 6 ng/cm$^2$ in such an assay. In some embodiments, the modified surface exhibits a fibrinogen adsorption of less than 4 ng/cm$^2$ in such an assay. In some embodiments, the modified surface exhibits a fibrinogen adsorption of less than 2 ng/cm$^2$ in such an assay. In some embodiments, the modified surface exhibits a fibrinogen adsorption of less than 1 ng/cm$^2$ in such an assay. In some embodiments, the modified surface exhibits a fibrinogen adsorption of less than 0.5 ng/cm$^2$ in such an assay. In some embodiments, the modified surface exhibits a fibrinogen adsorption of less than 0.25 ng/cm$^2$ in such an assay. In one embodiment, the grafted polymer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from or to a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from or to a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from or to a polyurethane polymer.

Preferred embodiments also show reduction in thrombus for substrates having a grafted polymer of the present invention. For example, thrombus reduction of modified substrates, i.e., substrates having a grafted polymer can be assessed relative to a reference substrate, i.e., the same or an otherwise functionally equivalent substrate lacking the grafted polymer, by exposing them to freshly harvested bovine blood, heparinized, with radiolabeled platelets, in a flow loop for 2 hours. As an assessment of anti-thrombogenic performance, samples are placed in an ex-vivo flow loop model of thrombosis. Anti-thrombogenic activity can be evaluated using ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for substrate containing a lumen by connecting the two ports of the substrate through a 2nd peristaltic pump. The size of tubing into which the article is placed and speed of the bloodflow may be adjusted based on the size of the article being tested. Preferably, when the articles are 14-15.5 French dialysis catheters, they are placed in a flow loop circuit with tubing diameter of approximately 12.5-25.4 mm inner diameter. Blood is pumped in the outer circuit at a rate of approximately 2.5 L/min, while blood in the inner circuit is pumped at a rate of approximately ~200-400 ml/min. When the articles are 10 French rods, they are placed in a flow loop circuit of approximately 6.4 mm inner diameter and blood flow rate is approximately 200 ml/min. After 60-120 minutes, the articles are removed, inspected visually for thrombus formation, and adhered platelets are quantified using a Gamma counter. For samples not containing a lumen, only an outer circuit may be used to measure thrombus on the outside of the device. In this assay, preferred embodiments show at least an 80% reduction relative to a reference substrate in adsorbed platelets and substantial visual reduction of thrombus. For example, in certain embodiments there is at least a 90% reduction in adsorbed platelets for modified substrates relative to reference substrates. Preferred embodiments show at least a 98% reduction in adsorbed platelets for modified substrates relative to reference substrates. Alternatively, in a preferred embodiment, the thrombogenecity of a modified substrate is reduced relative to the non-modified substrate, after exposure to a 47% (w/v) sodium citrate solution in DI water for greater than 3 days. Embodiments show a visual reduction of thrombus relative to for modified substrates relative to reference substrates. Preferred embodiments show at least an 80% reduction of a modified substrate relative to reference substrate in adsorbed platelets and substantial visual reduction of thrombus. Preferred embodiments show at least a 90% reduction in adsorbed platelets for modified substrates relative to reference substrates. Preferred embodiments show at least a 98% reduction in adsorbed platelets for modified substrates relative to reference substrates. Alternatively, the thrombogenecity of preferred embodiments are reduced relative to the non-modified substrate after exposure to animal serum and/or plasma. For example, the thrombogenecity of preferred embodiments are reduced after 55 day exposure to citrated human plasma at 37° C. for modified substrates relative to reference substrates. Embodiments show a visual reduction of thrombus for modified substrates relative to reference substrates. Preferred embodiments show at least an 80% reduction for modified substrates relative to reference substrates in adsorbed platelets and substantial visual reduction of thrombus. Preferred embodiments show at least a 90% reduction in adsorbed platelets for modified substrates relative to reference substrates. Preferred embodiments show at least a 98% reduction in adsorbed platelets for modified substrates relative to reference substrates.

Preferred embodiments show antibiofilm activity for modified substrates of at least 0.5 log, 1 log, 1.5 log, 2 log, 2.5 log, 3 log, or 4 log. More preferred embodiments have antibiofilm activity after extended exposures to PBS, serum, or plasma products. In one preferred embodiment, antibiofilm activity of 1 log is achieved after 30 days storage in PBS at 37° C. In a further preferred embodiment, antibiofilm activity of 1 log is achieved after 90 days storage in PBS at 37° C. In one preferred embodiment, antibiofilm activity of 2 log is achieved after 30 days storage in PBS at 37° C. In a further preferred embodiment, antibiofilm activity of 2 log is achieved after 90 days storage in PBS at 37° C. In one preferred embodiment, antibiofilm activity of 1 log is achieved after 30 days storage in citrated human plasma at 37° C. In a further preferred embodiment, antibiofilm activity of 1 log is achieved after 90 days storage in citrated human plasma at 37° C. In one preferred embodiment, antibiofilm activity of 2 log is achieved after 30 days storage in citrated human plasma at 37° C. In a further preferred embodiment, antibiofilm activity of 2 log is achieved after 90 days storage in citrated human plasma at 37° C.

Preferred embodiments show resistance to protein adsorption after extended exposure to PBS, which may indicate hydrolytic stability. In some embodiments, the modified surface exhibits a fibrinogen adsorption of less than 75 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 50 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 30 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 15 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 12 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 10 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 8 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 6 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 4 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 2 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 1 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 0.5 ng/cm$^2$ in a fibrinogen adsorption assay in which samples are incubated for 60 minutes at 37° C. in 70 µg/ml fibrinogen derived from human plasma after 30 days exposure to PBS at 37° C. In some embodiments, the modified surface exhibits a fibrinogen adsorption of less than 0.25 ng/cm$^2$ in a fibrinogen adsorption assay in which samples are incubated for 60 minutes at 37° C. in 70 µg/ml fibrinogen derived from human plasma after 30 days exposure to PBS at 37° C.

Preferred embodiments show resistance to protein adsorption after extended exposure to PBS, which may indicate hydrolytic stability. In some embodiments, the modified surface exhibits a fibrinogen adsorption of less than 75 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 50 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 30 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 15 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 12 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 10 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 8 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 6 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 4 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 2 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 1 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 0.5 ng/cm² in a fibrinogen adsorption assay in which samples are incubated for 60 minutes at 37° C. in 70 μg/ml fibrinogen derived from human plasma after 90 days exposure to PBS at 37° C. In some embodiments, the modified surface exhibits a fibrinogen adsorption of less than 0.25 ng/cm² in a fibrinogen adsorption assay in which samples are incubated for 60 minutes at 37° C. in 70 μg/ml fibrinogen derived from human plasma after 90 days exposure to PBS at 37° C.

In general, the polymeric primer and the grafted polymer (La, the polymer layer bound to the polymeric primer, sometimes also referred to herein as the non-fouling polymer layer) are independently any of a range of polymeric materials. For example, the polymeric primer and/or the grafted polymer may be a homopolymer or a copolymer. If a copolymer, the polymeric primer and/or the grafted polymer may be an alternating copolymer (e.g., [AB . . . ]$_n$, a periodic copolymer (e.g., [A$_n$B$_m$ . . . ] wherein n and m are different), a statistical copolymer (a copolymer in which monomers are arranged according to a known statistical rule), a random copolymer, or a block copolymer in which each of the blocks is independently a homopolymer or an alternating, periodic, statistical or random copolymer. Furthermore, when the polymeric primer and/or the grafted polymer is a copolymer it may be diblock, a triblock or other polyblock copolymer. For example, in one preferred embodiment, the grafted polymer comprises a homopolymer. In an alternative preferred embodiment, the grafted polymer comprises a random copolymer. In yet another embodiment, the grafted polymer comprises a block copolymer, e.g., a diblock or triblock copolymer.

In one embodiment the polymeric primer and the grafted polymer have a combined thickness which is at least equal to the surface roughness. For example, if the surface of a substrate has a global average $R_{rms}$ surface roughness of 100 nm, it is preferred in this embodiment that the polymeric primer and the grafted polymer have a combined global average dry thickness of at least 100 nm. In certain embodiments, it is preferred that the combined thickness of the polymeric primer and the grafted polymer exceed the global average $R_{rms}$ surface roughness. Thus, for example, in one embodiment the combined global average dry thickness of the polymeric primer and the grafted polymer is at least 110% of the global average $R_{rms}$ surface roughness. By way of further example, the combined global average dry thickness may be at least 200% of the global average $R_{rms}$ surface roughness of the substrate surface. By way of yet further example, the combined global average dry thickness may be at least 500% of the global average $R_{rms}$ surface roughness of the substrate surface. In a preferred embodiment, the global average dry thickness of the polymeric primer and the grafted polymer, in combination, is determined using a scanning electron microscope (SEM) under vacuum and global average $R_{rms}$ surface roughness is determined using an atomic force microscope. In one embodiment, the grafted polymer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from or to a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from or to a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from or to a polyurethane polymer.

In one embodiment, and particularly for articles having substrate surfaces with relatively large surface roughness values, the polymeric primer and the grafted polymer may reduce the surface roughness; stated differently, the modified surface, i.e., the surface of the article with the polymeric primer and the grafted polymer, has less surface roughness than the surface of the substrate. For example, in one such embodiment the global average $R_{rms}$ surface roughness of the modified surface is at least 50% less than the global average $R_{rms}$ surface roughness of the surface of the substrate. By way of further example, in one such embodiment the global average $R_{rms}$ surface roughness of the modified surface is at least 25% less than the global average $R_{rms}$ surface roughness of the surface of the substrate. By way of further example, in one such embodiment the global average $R_{rms}$ surface roughness of the modified surface is at least 10% less than the global average $R_{rms}$ surface roughness of the surface substrate. By way of further example, in one such embodiment global average $R_{rms}$ surface roughness of the modified surface is at least 5% less than the global average $R_{rms}$ surface roughness of the surface of the substrate. Independent of the relative surface roughness, the modified surface preferably has a relatively low surface roughness value. For example, the modified surface preferably has a global average $R_{rms}$ surface roughness of less than 25 nm. By way of further example, the modified surface may have a global average $R_{rms}$ surface roughness of less than 10 nm. By way of further example, the modified surface preferably has a global average $R_{rms}$ surface roughness of less than 5 nm. By way of further example, the modified surface preferably has a global average $R_{rms}$ surface roughness of less than 2 nm. By way of further example, the modified surface preferably has a global average $R_{rms}$ surface roughness of less than 1 nm. In one embodiment, the grafted polymer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from or to a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from or to a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from or to a polyurethane polymer.

In one embodiment, the grafted polymer may reduce the number of visual protrusions having a size greater than 0.1 micrometers relative to a reference substrate, that is, the same or an otherwise functionally equivalent substrate lacking the polymer primer and the grafted polymer. For example, the number of such visual protrusions may be reduced by at least 25%. By way of further example, the number of such visual protrusions may be reduced by at least 50%. By way of further example, the number of such visual protrusions may be reduced by at least 75%. By way of further example, the number of such visual protrusions may be reduced by at least 90%. In one embodiment, the grafted polymer may reduce the number of visual protrusions having a size greater than 0.5 micrometers relative to a reference substrate, that is, the same or an otherwise functionally equivalent substrate lacking the polymer primer and the grafted polymer. For example, the number of such protrusions may be reduced by at least 25%. By way of further example, the number of such visual protrusions may be reduced by at least 50%. By way of further example, the number of such visual protrusions may be reduced by at least 75%. By way of further example, the number of such visual protrusions may be reduced by at least 90.

Depending upon the article to which the surface modification is being applied and its working environment, the grafted polymer may have any of a wide range of thicknesses. For some applications, for example, the non-fouling grafted polymer will have a global average dry thickness of at least about 50 nm. For some applications, substantially thicker grafted polymers may be desirable. For example, the non-fouling grafted polymer may have a global average dry thickness of 50 micrometers. Typically, however, the non-fouling grafted polymer will have a global average dry thickness that is less. For example, in some embodiments the non-fouling grafted polymer will have a global average dry thickness of up to 10 micrometers. By way of further example, in some embodiments the non-fouling grafted polymer will have a global average dry thickness of up to 1 micrometer. By way of further example, in some embodiments the non-fouling grafted polymer will have a global average dry thickness of up to 500 nm. By way of further example, in some embodiments the non-fouling grafted polymer will have a global average dry thickness in the range of about 100 nm to about 1,000 nm. By way of further example, in some embodiments the non-fouling grafted polymer will have a global average dry thickness in the range of about 300 nm to about 600 nm. By way of further example, in some embodiments the non-fouling grafted polymer will have a global average dry thickness in the range of about 200 nm to about 400 nm. In a preferred embodiment, the global average dry thickness of the grafted polymer is determined using a scanning electron microscope (SEM) under vacuum. In one embodiment, the grafted polymer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from or to a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from or to a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from or to a polyurethane polymer In general, the grafted polymer preferably has a relatively uniform thickness. For example, in one embodiment it is generally preferred that the standard deviation of the global average dry thickness of the non-fouling grafted polymer not exceed 100% of the global average dry thickness of the non-fouling grafted polymer. By way of further example, in one embodiment the standard deviation of the global average dry thickness of the non-fouling grafted polymer will not exceed 50% of the global average dry thickness of the non-fouling grafted polymer By way of further example, in one embodiment the standard deviation of the global average dry thickness of the non-fouling grafted polymer will not exceed 20% of the global average dry thickness of the non-fouling grafted polymer. By way of further example, in one embodiment the standard deviation of the global average dry thickness of the non-fouling grafted polymer will not exceed 10% of the global average dry thickness of the non-fouling grafted polymer. The standard deviation of the thickness is preferably determined by taking at least 5, and more preferably at least 6-10, randomly spaced measurements of the grafted polymer thickness.

In one preferred embodiment, the polymeric primer is a copolymer grafted to the substrate, and the global average dry thickness of the polymeric primer is at least 50 nm as determined using a scanning electron microscope (SEM) under vacuum. In general, the surface modifications of the present invention are relatively hydrophilic. In general, the modified surface exhibits a static contact angle of less than 40 degrees. For example, modified surfaces of articles comprising non-fouling polymeric materials of the present invention grafted from a relatively hydrophobic polymer such as silicone, hydrocarbon rubbers, fluorosilicones, fluoropolymers and other polymers having a native contact angle of at least 90 degrees may exhibit a static contact angle of less than 40 degrees. By way of further example, modified surfaces of articles comprising non-fouling polymeric materials of the present invention grafted from a relatively hydrophobic substrate having a contact angle of at least 90 degrees may exhibit a static contact angle of less than 30 degrees. By way of further example, modified surfaces of articles comprising non-fouling polymeric materials of the present invention grafted from a relatively hydrophobic substrate having a contact angle of at least 90 degrees may exhibit a static contact angle of less than 25 degrees. By way of further example, modified surfaces of articles having non-fouling polymeric materials of the present invention grafted from a relatively hydrophobic substrate having a contact angle of at least 90 degrees may exhibit a static contact angle of less than 20 degrees. By way of further example, modified surfaces of articles having non-fouling polymeric materials of the present invention grafted from a relatively hydrophobic substrate having a contact angle of at least 90 degrees may exhibit a static contact angle of less than 15 degrees.

Articles having non-fouling polymeric materials of the present invention grafted from a less hydrophobic substrate such as polyurethane (including aliphatic polycarbonate-based polyurethanes) having a contact angle less than 90 degrees but greater than 25 degrees may exhibit a static contact angle of less than 25 degrees. For example, a modified surface, i.e., the surface of the article with the polymeric primer and the grafted polymer, having a contact angle of at least 25 degrees exhibits a static contact angle of less than 24 degrees. By way of further example, in one embodiment modified surfaces of articles having non-fouling polymeric materials of the present invention grafted from a substrate having a contact angle of at least 25 degrees exhibit a static contact angle of less than 23 degrees. By way of further example, in one embodiment modified surfaces of articles having non-fouling polymeric materials of the present invention grafted from a substrate having a contact angle of at least 25 degrees exhibit a static contact angle of less than 22 degrees. By way of further example, in one embodiment modified surfaces of articles having non-fouling polymeric materials of the present invention grafted from a substrate having a contact angle of at least 25 degrees exhibit a static contact angle of less than 21 degrees. By way of further example, in one embodiment modified surfaces of articles having non-fouling polymeric materials of the present invention grafted from a substrate having a contact angle of at least 25 degrees exhibit a static contact angle of less than 20 degrees. By way of further example, in one embodiment modified surfaces of articles having non-fouling polymeric materials of the present invention grafted from a substrate having a contact angle of at least 25 degrees exhibit a static contact angle of less than 19 degrees. By way of further example, in one embodiment modified surfaces of articles having non-fouling polymeric materials of the present invention grafted from a substrate having a contact angle of at least 25 degrees exhibit a static contact angle of less than 18 degrees. By way of further example, in one embodiment modified surfaces of articles having non-fouling polymeric materials of the present invention grafted from a substrate having a contact angle of at least 25 degrees exhibit a static contact angle of less than 17 degrees. By way of further example, in one embodiment modified surfaces of articles having non-fouling polymeric materials of the present invention grafted from a substrate having a contact angle of at least 25 degrees exhibit a static contact angle of less than 16 degrees. By way of further example, in one embodiment modified surfaces of articles having non-fouling polymeric materials of the present invention grafted from a substrate having a contact angle of at least 25 degrees exhibit a static contact angle of less than 15 degrees. By way of further example, in one embodiment modified surfaces of articles having non-fouling polymeric materials of the present invention grafted from a substrate having a contact angle of at least 25 degrees exhibit a static contact angle of about 5 to about 15 degrees. In one embodiment, the grafted polymer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from or to a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from or to a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from or to a polyurethane polymer.

In addition to being relatively hydrophilic, the grafted polymers of the present invention may also have a limited swelling capacity. For example, in one embodiment the difference between the dry thickness of the grafted polymer and the thickness of the grafted polymer under ambient conditions is not great. For example, the magnitude of the difference between the global average dry thickness of the grafted polymer as determined by standard scanning electron microscopy (SEM) to the global average humidified thickness of the grafted polymer as determined by environmental scanning electron microscopy (ESEM) is less than 200% of the global average dry thickness. For some applications, even less swelling capacity may be desirable. For example, the difference in thickness of the grafted polymer under such conditions may be less than 100% of the global average dry thickness. By way of further example, the difference in thickness of the grafted polymer as determined by SEM and ESEM under such conditions may be less than 50% of the global average dry thickness. By way of further example, the difference in thickness of the grafted polymer as determined by SEM and ESEM under such conditions may be less than 25% of the global average dry thickness. By way of further example, the difference in thickness of the grafted polymer as determined by SEM and ESEM under such conditions may be less than 10% of the global average dry thickness. By way of further example, the difference in thickness of the grafted polymer as determined by SEM and ESEM under such conditions may be less than 5% of the global average dry thickness. By way of further example, the difference in thickness of the grafted polymer as determined by SEM and ESEM under such conditions may be less than 1% of the global average dry thickness. By way of further example, no difference may be observable by such a comparison. In one embodiment, the grafted polymer in each of the foregoing embodiments and examples recited in this paragraph is a zwitterionic polymer. In one embodiment, the grafted polymer in each of the foregoing examples and embodiments recited in this paragraph is a polymer containing carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from or to a polyurethane polymer. In one embodiment, the grafted polymer in each of the foregoing examples and embodiments recited in this paragraph is a carboxyammonium or sulfoammonium polymer and the carboxyammonium or sulfoammonium polymer is grafted from or to a polyurethane polymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from or to a polyurethane polymer.

Advantageously, the process of the present invention may be tuned to provide independent control of the thickness, the thickness uniformity, and/or the swelling capacity of the grafted polymer, as well as the surface roughness and the degree of hydrophilicity (contact angle) of the article. Thus, for example, the process may be controlled to provide an article having a surface modification, i.e., the polymeric primer and grafted polymer, with a combined global average dry thickness that is at least 110% of the global average $R_{rms}$ surface roughness of the substrate, a standard deviation for the thickness of the non-fouling grafted polymer that does not exceed 100% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 200% of the global average dry thickness. By way of further example, the process may be controlled to provide an article having a surface modification, i.e., the polymeric primer and grafted polymer, with a combined global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 200% of the global average dry thickness. By way of further example, the process may be controlled to provide an article having a surface modification, i.e., the polymeric primer and grafted polymer, with a combined global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 100% of the global average dry thickness. By way of further example, the process may be controlled to provide a surface modification, i.e., a polymeric primer and grafted polymer with a combined global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 50% of the global average dry thickness. By way of further example, the process may be controlled to provide an article having a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 25% of the global average dry thickness. By way of further example, the process may be controlled to provide a surface modification, i.e., a polymeric primer and grafted polymer with a combined global average dry thickness that is at least 200% of the global average $R_{rms}$ surface roughness of the substrate, a standard deviation for the thickness of the non-fouling grafted polymer that does not exceed 20% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 25% of the global average dry thickness. By way of further example, the process may be controlled to provide a surface modification, i.e., a polymeric primer and grafted polymer with a combined global average dry thickness that is at least 200% of the global average $R_{rms}$ surface roughness of the substrate, a standard deviation for the thickness of the non-fouling grafted polymer that does not exceed 10% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 25% of the global average dry thickness. By way of further example, the process may be controlled to provide an article having a modified surface exhibiting a static contact angle of less than 25 degrees and a grafted polymer with a global average dry thickness that is at least 110% of the global average $R_{rms}$ surface roughness of the substrate, a standard deviation for the thickness of the non-fouling grafted polymer that does not exceed 100% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 200% of the global average dry thickness. By way of further example, the process may be controlled to provide an article having a modified surface exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 100% of the global average dry thickness. By way of further example, the process may be controlled to provide an article having a modified surface exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 50% of the global average dry thickness. By way of further example, the process may be controlled to provide an article exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 25% of the global average dry thickness. By way of further example, the process may be controlled to provide an article exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 10% of the global average dry thickness. By way of further example, the process may be controlled to provide an article exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 10% of the global average dry thickness. By way of further example, the process may be controlled to provide an article exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 5% of the global average dry thickness. By way of further example, the process may be controlled to provide an article exhibiting a static contact angle of less than 25 degrees and a grafted polymer with a global average dry thickness that is at least 200% of the global average $R_{rms}$ surface roughness of the substrate, a standard deviation for the thickness of the non-fouling grafted polymer that does not exceed 50% of the global average dry thickness of the non-fouling grafted polymer, and a magnitude of the difference between the global average dry thickness of the grafted polymer as determined by standard scanning electron microscopy (SEM) and the global average humidified thickness of the grafted polymer as determined by environmental scanning electron microscopy (ESEM) that is less than 5% of the global average dry thickness. By way of further example, in each of the foregoing examples, the grafted polymer may have a global average dry thickness in the range of 100 nm to 1,000 nm.

Substrates

In general, the substrate comprises any of a wide range of materials selected, for example, from one or more metals, ceramics, glasses, polymers, biological tissues, living or dead, woven and non-woven fibers, semi-metals such as silicon, and combinations thereof. In one embodiment, the substrate is a composite of two or more materials. For example, the substrate may comprise a polymeric coating, also sometimes referred to herein as an "undercoating," or a "precoating" over a metallic, ceramic, glass, polymeric, woven or non-woven fiber or semi-metal core. Alternatively, the substrate may comprise a polymeric material throughout, i.e., from its surface and into its bulk. By way of further example, the substrate may comprise a polymeric coating, overlying a metallic, ceramic, glass, polymeric, woven or non-woven fiber or semi-metal core inner layer which, in turn, overlies a metallic, ceramic, glass, polymeric, woven or non-woven fiber or semi-metal core.

Suitable metallic materials include, but are not limited to, metals and alloys based on titanium, such as unalloyed titanium (ASTM F67) and titanium alloys, such as ASTM F1108, Ti-6Al-4V ELI (ASTM F136), Nitinol (ASTM F2063), nickel titanium alloys, and thermo-memory alloy materials; stainless steel (ASTM F138 and F139), tantalum (ASTM F560), palladium, zirconium, niobium, molybdenum, nickel-chrome, or certain cobalt alloys including Stellite, cobalt-chromium (Vitallium, ASTM F75 and Wrought cobalt-chromium (ASTM F90)), and cobalt-chromium-nickel alloys such as ELGILOY®, PHYNOX® and HASTELLOY®

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polyimide, polyamine, polyanhydride, polyazine, poly (carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, aldehyde crosslinked resin, epoxy resin, phenolic resin, latex, or a copolymer or blend thereof. Exemplary polymers include polystyrene and substituted polystyrenes, polyalkylenes, such as polyethylene and polypropylene, poly(urethane)s, polyacrylates and polymethacrylates, polyacrylamides and polymethacrylamides, polyesters, polysiloxanes, polyethers (including polyacetals), poly(orthoesters), poly(carbonates), poly(hydroxyalkanoate)s, polyfluorocarbons, PEEK, Teflon, silicones, epoxy resins, KEVLAR®, NOMEX®, DACRON®, HYTREL®, PEBAX®, SURLYN®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof In one embodiment the substrate is a medical grade polyurethane or CARBOTHANE®, aliphatic polycarbonate-based polyurethanes, available from Lubrizol Corporation, blended with appropriate extrusion agents and plasticizers, possibly one already approved by the FDA or other appropriate regulatory agency for use in vivo. Preferred substrates include elastollan, pearlthane, desmopan, estane, pellethane, irogan, exelast EC, laripur, carbothane, CARBOTHANE®, isoplast, tecoflex, tecophilic, tecoplast, tecothane, biomer (Ethicon), biospan, cardiothane 51 (avothane), cardiomat, chronoflex AL, chronoflex AR, chronoflex C, corplex, corethane, mitrathane, rimplast, toyobo TM5, vialon, enka PUR, comfeel ulcus, viasorb, bioclusive, blisterfilm, opsite, tegaderm, epigard, lyofoam, omiderm, microthane, and surethane The substrate may optionally contain a radiopaque additive, such as barium sulfate, bismuth salts, gold foil, or tantalum to aid in radiographic imaging.

The quality of the surface modification formed in the polymerization process is, at least in part, influenced by the quality of the surface of the substrate prior to polymerization. Substrate surface flaws may be the result of additives or physical characteristics intentionally introduced to the substrate surface or material, or may be unintentionally present as artifacts of the manufacturing process or subsequent handling. For example, prior to polymerization, the surface may be contaminated with particles, waxes and other compositions that may remain on the surface of the substrate as an artifact of the manufacturing process, subsequent handling of the substrate, and/or as part of the intended substrate composition. The substrate surface may also include significant surface roughness, physical defects such as scratches, pinholes, or voids, and chemical defects, such as particle(s) of radiopacifing agents (such as barium sulfate, bismuth oxychloride, bismuth subcarbonate, bismuth trioxide, lanthanum oxide, tantalum pentoxide, and metallic gold, silver, platinum, palladium, tungsten, and tantalum) that are only partially contained within the substrate. For example, substrates containing barium sulfate typically have some barium sulfate particles that are partially contained within the substrate and partially exposed; the exposed portions of such barium sulfate particles may extend from the surface of a substrate to a height of as much as 1 micrometer (as measured from the surface of the substrate using SEM).

In accordance with one embodiment, the substrate surface is preferably pre-treated prior to polymerization. For example, the substrate surface may be cleaned using water, solvents, surfactants, enzymes, or other cleaning solutions or gases to remove particles, waxes or other foreign compositions that may be on the surface of the substrate or near the surface of the substrate. Alternatively, or additionally, the substrate surface may be mechanically, chemically or chemomechanically treated to reduce the incidence and/or the severity of physical and chemical defects.

In one embodiment, the substrate is treated prior to polymerization with a composition such as an acid, base, chelator or reactant that, removes or significantly reduces the amount of any compositions that are included as chemical defects. For example, exposed portions of barium sulfate particles may be removed using a mineral or organic acid and optionally, a chelator. In one such exemplary embodiment, polyurethane comprising particles of barium sulfate may be treated with hydrochloric acid to at least partially remove exposed barium sulfate particles.

Alternatively, or additionally, the substrate may be chemically, mechanically or chemomechanically polished prior to polymerization to reduce surface roughness, reduce the incidence and/or severity of cracks, pinholes and other structural defects in the substrate surface. For example, the substrate may be solvent polished by exposing the substrate to a vapor of a solvent such as chloroform, dioxane or tetrahydrofuran. After polishing, the substrate surface preferably has a global average $R_{rms}$ surface roughness that is less than the global average $R_{rms}$ surface roughness of the unpolished substrate. By way of further example, in one embodiment the polished substrate surface has a global average $R_{rms}$ surface roughness that is no more than 90% of the global average $R_{rms}$ surface roughness of the unpolished substrate surface. By way of further example, in one embodiment the polished substrate surface has a global average $R_{rms}$ surface roughness that is no more than 75% of the global average $R_{rms}$ surface roughness of the unpolished substrate surface. By way of further example, in one embodiment the polished substrate surface has a global average $R_{rms}$ surface roughness that is no more than 50% of the global average $R_{rms}$ surface roughness of the unpolished substrate surface.

The substrate may be in the form of, or form part of, gels, liquids, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), blood storage bags, surgical, medical or dental instruments, blood oxygenators, ventilators, pumps, drug delivery devices, tubing, wiring, electrodes, contraceptive devices, feminine hygiene products, endoscopes, grafts (including small diameter<6 mm), stents (including coronary, ureteral, renal, biliary, colorectal, esophageal, pulmonary, urethral, vascular, peripheral, neurovascular), stent grafts (including abdominal, thoracic, neurovascular and peripheral vascular), pacemakers, implantable cardioverter-defibrillators, cardiac resynchronization therapy devices, cardiovascular device leads, ventricular assist devices and drivelines, heart valves, vena cava filters, endovascular coils, catheters (including central venous, peripheral central, midline, peripheral, tunneled, dialysis access, urinary, neurological, peritoneal, intra-aortic balloon pump, angioplasty balloon, diagnostic, interventional, drug delivery, etc.), catheter connectors and valves (including needleless connectors), intravenous delivery lines and manifolds, shunts (including cardiac, cerebral, lumbar-peritoneal, pulmonary, portosystemic, portacaval, etc.), wound drains (internal or external including ventricular, ventriculoperitoneal, and lumboperitoneal), dialysis membranes, protein separation membranes, infusion ports, cochlear implants, endotracheal tubes, tracheostomy tubes, ventilator breathing tubes and circuits, guide wires, fluid collection bags, drug delivery bags and tubing, implantable sensors (e.g., intravascular, transdermal, intracranial, glucose sensors), diagnostic devices (e.g., microfuidic, microelectromechanical, and optical), ophthalmic devices including contact lenses, intraocular lenses and phacoemulsification devices, orthopedic devices (including hip implants, knee implants, shoulder implants, spinal implants (including cervical plates systems, pedicle screw systems, interbody fusion devices, artificial disks, and other motion preservation devices), screws, plates, rivets, rods, intramedullary nails, bone cements, artificial tendons, and other prosthetics or fracture repair devices), dental implants, periodontal implants, breast implants, penile implants, maxillofacial implants, cosmetic implants, valves, appliances, scaffolding, suturing material, needles, hernia repair meshes, tension-free vaginal tape and vaginal slings, prosthetic neurological devices, tissue regeneration or cell culture devices, dialyzer, cranial implants, syringes, blood collection containers, scrotal implants, calve implants, buttock implants, extraocular implants, horn implants, subdermal implants, transdermal implants, magnetic implants, medical devices containing microfluidics, blood based sensors used outside of the body, nanoparticles used as sensors, IV catheter sheath, or other medical devices used within or in contact with the body or any portion of any of these.

The substrate may be in the form of, or form part of, gels, foams, liquids, films, coatings, particles (nanoparticles, microparticles, or millimeter diameter beads), fibers (including woven and non-woven sponges and fabrics), marine and underwater coatings (including coatings for ships, submarines, marine and hydrokinetic devices, aquariums, underwater infrastructures, sewage pipes, and aqueduct tubes), packaging materials (including packaging for foods, beverages, cosmetics, and consumer products), desalination and water treatment systems (including condensers, spacers, pipelines, and membranes), separation membranes (including membranes for macrofiltration, microfiltration, ultrafiltration, nanofiltration, and reversed osmosis filtration), lab appliances and consumer products including containers (e.g. petri dishes, cell culture dishes, flasks, beakers), valves, needles, tapes, sealants, pipes, and tubes, earrings, body rings, contact lenses, cookware, gears (external/internal, spur, helical, double helical, bevel, hypoid, crown, worm, non-circular, etc.), turbomachinary (turbines and compressors), pumps (direct lift, displacement, velocity, buoyancy, and gravity), propellers, blades, knives, windshields, and glassware.

In one embodiment, the substrate is a vascularly inserted catheter such as a peripherally inserted central catheter (PICC), central venous catheter (CVC), or hemodialysis catheter, venous valves, punctual plugs, and intra-ocular devices and implants. In another embodiment, the substrate is a vascularly inserted catheter formed from a medical grade polyurethane or CARBOTHANE® or formed from a material coated with a medical grade polyurethane or CARBOTHANE®. In another embodiment, the substrate is a vascularly inserted catheter formed from a medical grade polyurethane or CARBOTHANE® containing a radiopaque additive, such as barium sulfate or bismuth salts to aid in radiographic imaging, or formed from a material coated with a medical grade polyurethane or CARBOTHANE® containing a radiopaque additive, such as barium sulfate or bismuth salts to aid in radiographic imaging.

In another embodiment, the substrate is a vascularly inserted catheter formed from a medical grade polyurethane such as Tecothane® or formed from a material coated with a medical grade polyurethane such as Tecothane®. In another embodiment, the substrate is a vascularly inserted catheter formed from a medical grade polyurethane such as Tecothane® containing a radiopaque additive, such as barium sulfate or bismuth salts to aid in radiographic imaging, or formed from a material coated with a medical grade polyurethane such as Tecothane® containing a radiopaque additive, such as barium sulfate or bismuth salts, to aid in radiographic imaging. In another embodiment, the substrate is a vascularly inserted catheter formed from a medical grade polyurethane such as Pellethane® or formed from a material coated with a medical grade polyurethane such as Pellethane®. In another embodiment, the substrate is a vascularly inserted catheter formed from a medical grade polyurethane such as Pellethane® containing a radiopaque additive, such as barium sulfate or bismuth salts, to aid in radiographic imaging, or formed from a material coated with a medical grade polyurethane such as Pellethane® containing a radiopaque additive, such as barium sulfate or bismuth salts, to aid in radiographic imaging.

In one embodiment, the substrate comprises functional groups that may be used to react with complimentary chemically reactive groups in the polymeric primer and covalently attach the polymeric primer to the substrate. For example, the substrate may possess amines, which can be introduced through aminolysis of the substrate; azide or terminal alkyne functionality which enable the use of click chemistry methods; or olefins, α,β-unsaturated carbonyls, or thiols which enable the use of thiol reactions. Particular embodiments include polymeric primers having the following functional groups incorporated into them to promote coating: hydrophobic, epoxy, siloxane, phosphonic acids, carboxylic acids, DOPA, titanates, amines, isocyanates, and boronic acids. These groups can be incorporated into the primer either through copolymerization of the appropriate functional groups, or via polymer analog conversions of the appropriate polymer. In some cases the modification may be enhanced through the use of catalysts, for example, the coating of polyurethane substrates with a primer incorporated with isocyanates is enhanced with the use of catalysts, including tertiary amines, such as dimethylcyclohexylamine, and organometallic compounds, such as dibutyltin dilaurate or bismuth octanoate.

Polymeric Primer

In accordance with one aspect of the present invention, a polymeric primer is applied to the substrate. As discussed in greater detail elsewhere herein, the substrate may comprise a single material, e.g., a metal, ceramic, glass, polymer, biological tissue, woven and non-woven fiber, or semi-metal such as silicon. Alternatively, the substrate may be a composite of two or more layered materials; for example, the substrate may comprise (i) an inner layer (or bulk) comprising a metal, ceramic, glass, polymer, biological tissue, woven and non-woven fiber, or semi-metal, and combinations thereof, and (ii) an outer layer comprising a polymer.

Regardless of whether the substrate is a single material or composite, the polymeric primer is applied to at least a portion of the outer surface of the substrate. Viewed from the perspective of the polymeric primer, the polymeric primer has two surfaces, an inner surface and an outer surface with the inner surface being proximate to the substrate. As described in greater detail herein, a non-fouling polymer layer is grafted from or to the outer surface of the polymeric primer.

In general, the polymeric primer will have a global average dry thickness of at least about 50 nm. In some embodiments, the polymeric primer will be substantially thicker; for example, the polymeric primer may have a global average dry thickness of as much as 500 micrometers. In general, however, the polymeric primer will be thinner. For example, the polymeric primer may have a global average dry thickness of about 1-50 micrometers. By way of further example, the polymeric primer may have a global average dry thickness of about 10-30 micrometers.

The polymeric primer may be attached covalently or non-covalently to the substrate surface. For example, the polymeric primer may be attached to the substrate by one or more non-covalent interactions (e.g., hydrogen bonds, ionic bonds, static forces, van der Waals interactions, combinations thereof, or the like), or a combination thereof. Alternatively, the polymeric primer may be covalently attached to the substrate surface. Particular embodiments include primers with the following functional groups incorporated into them to promote coating to the substrate: hydrophobic, epoxy, siloxane, phosphonic acids, carboxylic acids, DOPA, titanates, amines, isocyanates, and boronic acids. These groups can be incorporated into the primer either through copolymerization of the appropriate functional groups, or via polymer analog conversions of the appropriate polymer. In some cases the modification may be enhanced through the use of catalysts, for example, the coating of polyurethane substrates with a primer incorporated with isocyanates is enhanced with the use of catalysts, including tertiary amines, such as dimethylcyclohexylamine, and organometallic compounds, such as dibutyltin dilaurate or bismuth octanoate.

In one presently preferred embodiment, the polymeric primer is covalently attached to the substrate. In those embodiments where the polymeric primer is covalently attached to the substrate, the polymeric primer can be immobilized directly on the substrate surface or through a linker or tether. The linker or tether can be part of the polymeric primer or can be grafted to or from the surface of the substrate prior to application of the polymeric primer. Multifunctional linkers include 3-aminopropyltriethoxysilane, 1,6-hexanediisocyanate, and glutaraldehyde.

In a preferred embodiment, the polymeric primer is applied using a process that does not substantially chemically or mechanically alter the properties of the substrate. For example, the solvent, temperature, and reaction times used during the application process may be selected to minimize the impact on the mechanical properties of the substrate.

In one exemplary embodiment, a polymeric primer is applied to a substrate by exposing the substrate to a solution containing a presynthesized polymer. For example, in one embodiment, a polymer is dissolved in a solvent in which the substrate is substantially insoluble and the substrate is dipped therein to deposit a layer of about 50 nm to about 500 micrometers of the polymer. In further embodiments, the deposited layer is about 100 nm to 50 micrometers. In further embodiments, the deposited layer is about 100 nm to 25 micrometers. In further embodiments, the deposited layer is about 100 nm to 10 micrometers. The substrate may be dipped once or multiple times. The thickness of the polymeric primer can be tailored by varying the concentration of undercoat in solution and/or by increasing the number of dip steps and/or the changing the speed of the dip step. The coated substrates may then be dried to remove solvent and heated, for example, 16 hours at 60° C., to cure the undercoating so that it is covalently bound to the substrate. A washing step may follow the application of the polymeric primer. Optionally, the deposited polymer is crosslinked as it is being applied or after it has been applied to the substrate.

In some instances, the substrate will have a complex shape or geometry with inner and outer surfaces to be coated. For example, multi-lumen catheters have an exterior surface and two or more longitudinal lumens that may be coated. Polymeric primers may be applied by simultaneously dipping the external portion in a polymer solution or dispersion to coat the external portion and flowing a polymer solution or dispersion through the intralumenal portion to coat the intralumenal portion. Coating application parameters utilized to effect coating control include the solvent system, percent solids and viscosity, and cure temperature and time. Suitable solvents for the polymer primer layer include, but are not limited to, alcohols, such as methanol or ethanol. Application and cure temperature can vary, for example between ambient and 50° C. so as not to affect physical properties of the underlying substrate, for example, a polyurethane substrate. Solids content can vary between 0.5-10%, with solution viscosity no higher than 30 cP for ease of handling and application. In some embodiments, the global average dry thickness of the primer or polymer layer is <1% of the diameter of a catheter lumen in which it is applied. In further embodiments, the global average dry thickness of the primer or polymer layer is <0.5% of the diameter of a catheter lumen in which it is applied. In further embodiments, the global average dry thickness of the primer or polymer layer is <0.25% of the diameter of a catheter lumen in which it is applied. In further embodiments, the global average dry thickness of the primer or polymer layer is <0.1% of the diameter of a catheter lumen in which it is applied. The global average dry thickness of the primer or polymer layer is <0.05% of the diameter of a catheter lumen in which it is applied. In further embodiments, In further embodiments, the global average dry thickness of the primer or polymer layer is <0.01% of the diameter of a catheter lumen in which it is applied. In further embodiments, the global average dry thickness of the primer or polymer layer is <0.001% of the diameter of a catheter lumen in which it is applied.

In one embodiment, the polymeric primer comprises functional groups that react with complimentary chemically reactive groups in the substrate to covalently attach the polymeric primer to the substrate. For example, the polymeric primer may contain groups that react with amines possessed by the substrate, azide or terminal alkyne functionality which enable the use of click chemistry methods; or olefins, α,β-unsaturated carbonyls, or thiols which enable the use of thiol reactions.

Other chemistries for attaching the polymeric primer to the substrate can include anionic or cationic reactions, nucleophile-electrophile reactions, addition reactions, such as Michael addition, ring opening methods, such as epoxide or aziridine, and metathesis reactions. Organometallic reactions include chelation type bonding between a mono- or multi-dentate organic ligands and inorganic atoms with empty d-orbitals available for bonding. In some embodiments the chemistries used to immobilize a coating or coating set can be catalyzed or un-catalyzed. Particular embodiments include primers with the following functional groups incorporated into them to promote coating: hydrophobic (such as butyl, 2-ethylhexyl, decyl, lauryl, and phenyl), epoxy, siloxane, phosphonic acids, carboxylic acids, DOPA, titanates, amines, isocyanates, and boronic acids. These groups can be incorporated into the primer either through copolymerization of the appropriate functional groups, or via polymer analog conversions of the appropriate polymer. In some cases the modification may be enhanced through the use of catalysts, for example, the coating of polyurethane substrates with a primer incorporated with isocyanates is enhanced with the use of catalysts, including tertiary amines, such as dimethylcyclohexylamine, and organometallic compounds, such as dibutyltin dilaurate or bismuth octanoate.

Polymeric primers may be formed by any synthetic means known in the art including, but not limited to, free radical polymerization (e.g., thermal, UV, and/or redox), ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), such as solvent casting, dip-coating, spray-coating, plasma polymerization, roller coating, electrostatic coating, or brush coating.

As discussed in detail herein, the polymeric primer provides reactive functional groups for bonding grafted polymer, and/or for adhesion to the substrate. The concentration of the functional groups of the primer can be estimated by the composition of primer polymers. In one embodiment, for example, the polymeric primer is a copolymer and at least 10% of the monomeric residues of which are residues of functional groups that can react with the grafted polymers, such as amine groups, epoxy groups, carboxylic groups, and isocyanate groups.

In various embodiments, the polymeric primer and/or grafted polymer may be detected on the substrate using EDS mapping, XPS, or TOF-SIMS. Furthermore, the sample may be freeze fractured in liquid nitrogen to expose the polymeric primer and/or the grafted polymer and substrate interface. Fractured surface may then be coated with a thin layer of Au/Pt and observed under a scanning electron microscope with Energy Dispersive X-ray Analyser (EDAX) for element analysis. Suitable instruments include a FEI/Philips XL30 FEG ESEM. In order to assess the polymeric primer and/or grafted polymer at least 25, and preferably at least 50, representative locations spaced approximately evenly across the portion of the article carrying the modification should be analyzed. For example, if a polymeric primer and/or grafted polymer layer is applied to the indwelling portion of a catheter, the representative locations are approximately evenly spaced across the indwelling portion of the catheter. It is preferred to measure the thickness at representative points across the longest dimension of the portion of the article that is covered with the polymer layer. The polymeric primer and/or grafted polymer may be quantified and/or detected on the substrate or grafted polymer methods, including FTIR-ATR, electron spectroscopy for chemical analysis (ESCA, also called X-ray photoelectron spectroscopy, XPS), secondary ion mass spectrometry (SIMS), and surface-enhanced Raman spectroscopy (SERS).

Reactive functional groups (for interaction with complimentary reactive functional groups in the grafted polymer) may be present on the polymeric primer as a result of the polymerization reaction that formed the polymeric primer (i.e., the functional group(s) were present on the monomer used in polymerization). Alternatively, reactive functional groups may be created in the polymeric primer post-polymerization. Suitable methods for creating reactive functional groups in polymeric primers include, for example, physical adsorption, chemical reaction, plasma treatment, and/or surface grafting methods. Physical adsorption methods involve any small reactive agents which are pre-adsorbed or migrate to the surface by methods including, but not limited to, solvent imbibing, blending, and vapor deposition. Chemical reaction methods to create reactive functional groups include, but are not limited to, amination, hydrolysis, and silanization. Plasma treatment methods include, but are not limited to, inert gas, reactive gas, monomers, and plasma polymerization treatment.

Additionally, or alternatively, other (reactive) functional groups can be introduced to the polymeric primer by way of a polymer analog reaction. In accordance with conventional polymer analog modifications, a reaction(s) takes place along the polymer chain to convert particular chemical functional groups into different functional groups, preferably without altering the degree of polymerization of the starting (primer) polymer or otherwise affecting its performance. By way of example only and not in any sense limiting, conventional polymer analog reactions may be used to halogenate or oxidize saturated polymers; hydrogenate, halogenate or epoxify unsaturated polymers; convert esters, amides, and nitrile pendant groups to their corresponding carboxyl groups; and cause phenyl pendent groups to undergo characteristic reactions of aromatic rings, such as alkylation, sulfonation, or halogenation; among other transformations. In general, preferred polymer analog reactions and corresponding transformations are those which minimize competing degradation of the polymer or which otherwise do not substantially affect performance of the non-fouling polymer or article.

In one embodiment, the reactive functional group present on the polymeric primer (for interaction with complimentary reactive functional groups in the grafted polymer) is selected from the group consisting of alkyne, amine (primary, secondary or tertiary), anhydride, azide, carboxyl, epoxy (e.g., glycidyl), halogen, hydroxyl, isocyanate, peroxide, silanol, thiol, and photo-initiator groups, and combinations thereof.

Before the polymeric primer is applied to the substrate, the surface of the substrate may be treated to improve the adherence of the polymeric primer. For example, the substrate may be subjected to an oxidation pretreatment to increase the adhesion properties to the polymeric primer. By way of further example, the substrate may be silanized using small molecule or polymeric reagents such as am inoproyltriethoxysilane, glycidylpropyltriethoxysilane, vinylpropyltriethoxysilane, and 3-aminopropylsilsesquioxane to increase the adhesion properties to the polymeric primer. By way of further example, the substrate surface may be subjected to alternating organic and aqueous treatments.

Additionally, or alternatively, the polymeric primer may decrease the roughness of substrates and cover the defects on the substrates such as scratches, pinholes, or voids. These defects also include additives, heterophases and impurities accumulated on the surfaces such as radiopacifing agents, fillers, and plasticizers. In one embodiment, the primed substrate preferably has a global average $R_{rms}$ surface roughness that is less than the global average $R_{rms}$ surface roughness of the unpolished substrate z measured by AFM.

In one preferred embodiment, the polymeric primer conceals substrate surface defects or reduces surface roughness. In general, however, the polymeric primer preferably has a global average dry thickness that equals or exceeds the global average $R_{rms}$ surface roughness of the uncoated substrate. For example, in one embodiment, the polymeric primer has a global average dry thickness that is at least 110% of the global average $R_{rms}$ surface roughness of the uncoated substrate. By way of further example, in one embodiment, the polymeric primer has a global average dry thickness that is at least 200% of the global average $R_{rms}$ surface roughness of the uncoated substrate. By way of further example, in one embodiment, the polymeric primer has a global average dry thickness that is at least 300% of the global average $R_{rms}$ surface roughness of the uncoated substrate. By way of further example, in one embodiment, the polymeric primer has a global average dry thickness that is at least 400% of the global average $R_{rms}$ surface roughness of the uncoated substrate.

In addition, the polymeric primer preferably reduces the global average $R_{rms}$ surface roughness of the substrate surface. Stated differently, the coated substrate surface preferably has a global average $R_{rms}$ surface roughness that is less than the global average $R_{rms}$ surface roughness of the substrate prior to the application of the polymeric primer (i.e., the uncoated substrate). For example, in one embodiment the polymer primer coated substrate surface has a global average $R_{rms}$ surface roughness that is no more than 90% of the global average $R_{rms}$ surface roughness of the substrate prior to the application of the precoat. By way of further example, in one embodiment the polymer primer coated substrate surface has a global average $R_{rms}$ surface roughness that is no more than 75% of the global average $R_{rms}$ surface roughness of the uncoated substrate. By way of further example, in one embodiment the polymer primer coated substrate surface has a global average $R_{rms}$ surface roughness that is no more than 50% of the global average $R_{rms}$ surface roughness of the uncoated substrate.

In one embodiment, the polymer primer coated substrate surface has a global average dry thickness that equals or exceeds the global average $R_{rms}$ surface roughness of the uncoated substrate and a global average $R_{rms}$ surface roughness that is less than the global average $R_{rms}$ surface roughness of the substrate prior to the application of the polymeric primer (i.e., the unprimed substrate). For example, in one embodiment the polymeric primer has a global average dry thickness that is at least 110% of the global average $R_{rms}$ surface roughness of the unprimed substrate and the polymeric primed substrate surface has a global average $R_{rms}$ surface roughness that is no more than 90% of the global average $R_{rms}$ surface roughness of the unprimed substrate. By way of further example, in one embodiment the polymeric primer has a global average dry thickness that is at least 110% of the global average $R_{rms}$ surface roughness of the unprimed substrate and the polymeric primed substrate surface has a global average $R_{rms}$ surface roughness that is no more than 75% of the global average $R_{rms}$ surface roughness of the unprimed substrate. For example, in one embodiment the polymeric primer has a global average dry thickness that is at least 110% of the global average $R_{rms}$ surface roughness of the unprimed substrate and the polymeric primed substrate surface has a global average $R_{rms}$ surface roughness that is no more than 50% of the global average $R_{rms}$ surface roughness of the unprimed substrate.

Regardless of the density or size of any substrate surface defects or the substrate surface roughness, the surface of the polymeric primed substrate preferably has a global average $R_{rms}$ surface roughness that is no more than 100 nm. In certain embodiments, the surface is even smoother. For example, the surface may have a global average $R_{rms}$ surface roughness of less than 50 nm. In some embodiments, the surface may have a global average $R_{rms}$ surface roughness of less than 20 nm.

Additionally, or alternatively, the surface of the polymeric primed substrate preferably has a visually observable surface defect density (i.e., visually observable number over a field size of 20×20 micrometers) of defects having a size (i.e., a longest dimension) greater than about 0.5 micrometers that is less than 0.1 defects/$\mu m^2$. For example, the surface of the polymeric primed substrate may have a surface defect density of defects having a size greater than about 0.5 micrometers that is less than 0.05 defects/$\mu m^2$. By way of further example, the surface of the polymeric primed substrate may have a surface defect density of defects having a size greater than about 0.5 micrometers that is less than 0.01 defects/$\mu m^2$. By way of further example, the surface of the polymeric primed substrate may have a surface defect density of defects having a size greater than about 0.5 micrometers that is less than 0.002 defects/$\mu m^2$. By way of further example, the surface of the polymeric primed substrate may have a surface defect density of defects having a size greater than about 0.5 micrometers that is less than 0.001 defects/$\mu m^2$ As discussed in further detail below, one function of the polymeric primer is to provide reactive functional groups to immobilize the grafted polymer. In preferred embodiments, one or more functional groups on the polymeric primer and one or more complimentary reactive functional groups in the grafted polymer may be used to immobilize the grafted polymer on the polymeric primer. A range of reactive functional groups are described below for both the polymeric primer and grafted polymer, though any reactive combination may be used. In preferred embodiments, the reactive combination includes, but is not limited to, epoxy-amine, isocyanate-carboxyl, glycidyl-anhydride, amine-anhydride, silanol-silanol, isocyanate-amine, carboxyl-amine, and hydroxyl-carboxyl groups.

The polymeric primer may comprise a homopolymer or a copolymer, such as random or block copolymers, formed by chain-growth or step-growth polymerization. Suitable monomers include, but are not limited to, acrylates, including substituted acrylates, such as hydroxyalkyl acrylates, acrylates with primary, secondary, or tertiary amino groups, alkyl methacrylates, and reactive or crosslinkable acrylate, such as acrylates containing silyl groups, double bonds, or other reactive functional groups; acrylamides, including substituted acrylamides as described above for acrylates; vinyl compounds; multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams; and combinations thereof. Exemplary monomers are listed below:

(1) Charged methacrylates or methacrylates with primary, secondary or tertiary amine groups, such as, 3-sulfopropyl methacrylate potassium salt, (2-dimethylamino) ethyl methacrylate) methyl chloride quaternary salt, [2-(methacryloyloxy)ethyl]trimethyl-ammonium chloride, methacryloyl chloride, [3-(methacryloylamino) propyl]-trimethylammonium chloride), 2-aminoethyl methacrylate hydrochloride, 2-(diethylamino)ethyl methacrylate, 2-(dimethylamino)ethyl methacrylate, 2-(tert-butylamino)ethyl methacrylate, and 2-(tert-butylamino-ethyl methacrylate.

(2) Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3, 3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10, 10-heptadecafluorodecyl methacrylate.

(3) Reactive or crosslinkable methacrylates, such as 2-(trimethylsilyloxy)-ethylmethacrylate, 3-(trichlorosilyl)propyl methacrylate, 3-(trimethoxysilyl)-propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate, 3-(dimethylchlorosilyl)propyl methacrylate, isocyanates, such as 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

(4) Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

Condensation type monomers can also be used.

Acrylamide and/or methacrylamide of the monomers listed above can also be used, as well as other monomers with unsaturated bonds.

Multinfunctional monomers, such di, tri, or tetraacrylates or substituted acrylates can be used to form highly branched structures which can provide a higher concentration of functional groups for attachment of the grafted polymer.

In one embodiment, the polymeric primer is a copolymer of glycidyl methacrylate (GMA), 2-hydroxypropyl methacrylate (HPMA), lauryl methacrylate (LMA), and trimethoxysilyl methacrylate (TMOSMA). In another embodiment, the polymeric primer is a copolymer of 2-aminoethyl methacrylate (AEMA), 2-hydroxypropyl methacrylate (HPMA), lauryl methacrylate (LMA), and trimethoxysilyl methacrylate (TMOSMA).

Grafted Polymer

The grafted polymer is attached, covalently or non-covalently, to the outer surface of the polymeric primer. The grafted polymer can be immobilized covalently to the polymeric primer by (a) covalent bond formation between reactive functional groups in the polymeric primer and complimentary reactive functional groups in a presynthesized polymer using a graft-to approach, or (b) in situ polymerization of a monomer from the reactive functional groups in the polymeric primer using a graft-from approach. Alternatively, a presynthesized polymer may be non-covalently attached to the reactive functional groups in the polymeric primer.

In one embodiment, a graft-from approach is employed, and a polymer is grown in situ by a chain-growth polymerization process or a step-growth polymerization process. For example, the polymerization process may employ photo-initiated, thermal-initiated, redox-initiated, controlled free radical, or anionic and cationic reactions.

Alternatively, the grafted polymer can be applied by dipping the polymeric primed substrate into a solution of the graft polymer. Suitable solvents for the grafting solution include, but are not limited to, water and alcoholic solvents such as methanol and ethanol; preferably, the polymeric primer has limited solubility in the grafting solution. The thickness of the layer can be controlled by the number of dips and/or the rate of immersion. After drying, the grafted polymer can be cured by heating the substrate, for example for 40 hours at 60° C.

Reactive functional groups (for interaction with complimentary reactive functional groups in the grafted polymer) may be present on the polymeric primer as a result of the polymerization reaction that formed the polymeric primer (i.e., the functional group(s) were present on the monomer used in polymerization). Alternatively, reactive functional groups may be created in the polymeric primer post-polymerization. Suitable methods for creating reactive functional groups in polymeric primers include, for example, physical adsorption, chemical reaction, plasma treatment, and/or surface grafting methods. Physical adsorption methods involve any small reactive agents which are pre-adsorbed or migrate to the surface by methods including, but not limited to, solvent imbibing, blending, and vapor deposition. Chemical reaction methods to create reactive functional groups include, but are not limited to, amination, hydrolysis, and silanization. Plasma treatment methods include, but are not limited to, inert gas, reactive gas, monomers, and plasma polymerization treatment.

Additionally, or alternatively, other (reactive) functional groups can be introduced to the polymeric primer by way of a polymer analog reaction. In accordance with conventional polymer analog modifications, a reaction(s) takes place along the polymer chain to convert particular chemical functional groups into different functional groups, preferably without altering the degree of polymerization of the starting (primer) polymer or otherwise affecting its performance. By way of example only and not in any sense limiting, conventional polymer analog reactions may be used to halogenate or oxidize saturated polymers; hydrogenate, halogenate or epoxify unsaturated polymers; convert esters, amides, and nitrile pendant groups to their corresponding carboxyl groups; and cause phenyl pendent groups to undergo characteristic reactions of aromatic rings, such as alkylation, sulfonation, or halogenation; among other transformations. In general, preferred polymer analog reactions and corresponding transformations are those which minimize competing degradation of the polymer or which otherwise do not substantially affect performance of the non-fouling polymer or article.

In one embodiment, the reactive functional group present on the polymeric primer (for interaction with complimentary reactive functional groups in the grafted polymer) is selected from the group consisting of alkyne, amine (primary, secondary or tertiary), anhydride, azide, carboxyl, epoxy (e.g., glycidyl), halogen, hydroxyl, isocyanate, peroxide, silanol, thiol, and photo-initiator groups, and combinations thereof.

Where a graft-to approach is employed, the functional groups on the polymeric primer and the functional groups on the graft polymeric form covalent bonds. Similar to the reactive functional groups on the polymeric primer, functional groups present on graft-to polymeric materials may be present as a result of the polymerization reaction (i.e., the functional group(s) were present on the monomer used in polymerization), or may be created or converted using the methods described above (e.g., by way of a polymer analog reaction or other chemical reaction, plasma treatment, or physical adsorption). In one embodiment, the reactive functional group present on the graft-to polymeric material is selected from the group consisting of acid chloride, activated ester (e.g., activated carboxylic esters), aldehyde, alkyl and aryl halide (to couple, e.g., via Buchwald substitutions), alkyne, anhydride, boronic acid (to couple, e.g., via boronic esters), carboxylic acid and ester, diene (to couple, e.g., via a Diels-Alder reaction), DOPA, epoxy (e.g., glycidyl), halogen, hydroxyl, isocyanate, lactones, phosphonic acid and ester, primary, secondary or tertiary amine, silanol, sulfonic acid and ester, sultone, and thiol groups, unsaturated groups (e.g. vinyl, acrylate, methacrylate, styrenyl), heat-reactive polyhydrocarbons, UV-reactive polyhydrocarbons, and combinations thereof.

Where a graft-from approach is employed, radical initiators are reacted with the functional groups on the polymeric primer and the graft-from polymerization, and immobilization of the graft-from polymeric material, is initiated by exposing the polymeric primer to a suspension of the monomer or monomers to be polymerized. Thus, immobilization and at least initial polymerization occur simultaneously. In various embodiments, immobilization and polymerization may employ photo-initiated, thermal-initiated, redox-initiated, controlled free radical, or anionic and cationic reactions.

In general, any radical initiator for the various functional groups on the polymeric primer may be employed.

In one embodiment, the graft-from radical initiator is an ultraviolet (UV) initiator.

In another embodiment, a heat activated (thermal) radical initiator is used, in place of the UV initiator in the graft-from approach.

In another embodiment, a redox initiator system is used to initiate polymerization from the surface of the polymeric primer in the graft-from approach.

Suitable UV, thermal, and redox initiators, and their use in graft-from approaches, are described in further detail below.

Still other radical initiation approaches may involve the use of amine initiation of epoxide or ethyloxazoline polymerizations, boronic acids, condensation with phenols, ATRP polymerization (such as Cu(I)/bi-pyridine complexes), and combinations thereof.

Where a graft-through approach is employed, a polymeric primer is grafted to a substrate, optionally followed by derivatization of the functional groups thereon, and further followed by a graft-from approach. Thus, immobilization and polymerization may generally occur in a step-wise fashion. Graft-through approaches, therefore, may employ the same functional groups and radical initiators as that of graft-to and graft-from approaches.

The graft polymeric material may be immobilized directly on the polymeric primer according to the graft-to and graft-from approaches discussed above, or through a linker or tether. In general, the linker or tether serves as a bifunctional moiety (e.g., in the form of a coupling molecule) that facilitates crosslinkage of the graft polymeric material and the polymeric primer. The linker or tethering reaction may generally involve the use of one or more coupling molecules or compounds for the various reactive functional groups on the polymeric primer and the graft polymeric material (e.g., one or more reactive anhydride, aldehyde, alkyne, carboxylic acid, diene, epoxy (e.g., glycidyl), halogen, hydroxyl, isocyanate, ketone, lactone, primary, secondary and/or tertiary amine, silanol, sultone, thiol, and unsaturated groups (e.g., vinyl, acrylate, methacrylate, styrenyl), and combinations thereof).

In one embodiment, the grafted polymer is immobilized to the polymeric primer using a tether or linker. The stability of the grafted polymer may be dependent on the method of immobilization to the polymeric primer. Variations in tether chemistry can provide an opportunity to develop highly efficient, biocompatible and bioresponsive immobilized non-fouling polymer layers. The bonding between a tether molecule and the grafted polymer can be covalent, non-covalent, ionic, dispersive, coordinate, chelation type bonding or combinations thereof. To ensure adequate immobilization, a non-labile or un-reactive tether can be synthesized. Such a tether should provide a linkage that is stable in vivo between the substrate surface and the immobilized molecule or material.

Tethers can be formed by synthetic means known in the art including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET). Tethers can be formed either by grafting from the substrate or by grafting to the substrate and subsequently grafting to the tether the non-fouling material and/or biomolecule.

In one embodiment, the linkers and tethers are responsive to the surrounding environment. For example, the linkers and tethers may release the grafted polymer under specific conditions, e.g., oxidative conditions, low pH, or when the device arrives at the desired site. Conversely, when the tethering composition is not in the presence of releasing conditions, the linker or tether re-immobilizes the grafted polymer on the polymeric primer, which may be present in the surrounding solution or retained within a device in which the primers are found.

Tethers and linkers may be molecules or polymers containing one or more functional groups including, but not limited to, divinyl compounds, diacrylates, dimethacrylates, diisocynates, diglycidyl ethers, and dimaleic anhydrides. Alternatively, hetero-bifunctional tethers may be used.

Various combinations and permutations of graft-to and graft-from approaches may be employed on the primed substrate and/or (and/or any other surface modification(s)). For example, both the polymeric primer and the grafted polymer may be applied using a graft-to approach (i.e., graft-to-graft-to). By way of another alternative example, one of the polymeric primer and the grafted polymer may be applied using a graft-to approach, while the other of the polymeric primer and the grafted polymer may be applied using a graft-from approach. Thus, by way of example, the polymeric primer may be applied using a graft-to approach and the grafted polymer may be applied using a graft-from approach (i.e., graft-to-graft-from), or, by way of another example, the polymeric primer may be applied using a graft-from approach and the grafted polymer may be applied using a graft-to approach (i.e., graft-from-graft-to). It will be understood that this overall theme may be extended to applications in which three, four, or more modifications are made, e.g., the modifications selected from (graft-to-graft-to-graft-to); (graft-to-graft-to-graft-from); (graft-to-graft-from-graft-to); (graft-to-graft-from-graft-from); (graft-from-graft-to-graft-to); (graft-from-graft-to-graft-from); (graft-from-graft-from-graft-to); (graft-from-graft-from-graft-from); selected from (graft-to-graft-to-graft-to-graft-to); (graft-to-graft-to-graft-to-graft-from); (graft-to-graft-to-graft-from-graft-to); (graft-to-graft-to-graft-from-graft-from); (graft-to-graft-from-graft-to-graft-to); (graft-to-graft-from-graft-to-graft-from); (graft-to-graft-from-graft-from-graft-to); (graft-to-graft-from-graft-from-graft-from); (graft-from-graft-to-graft-to-graft-to); (graft-from-graft-to-graft-to-graft-from); (graft-from-graft-to-graft-from-graft-to); (graft-from-graft-to-graft-from-graft-from); (graft-from-graft-from-graft-to-graft-to); (graft-from-graft-from-graft-to-graft-from); (graft-from-graft-from-graft-from-graft-to); (graft-from-graft-from-graft-from-graft-from); and so on. In one particular embodiment, the polymeric primer is applied using a graft-to approach and the grafted polymer is applied using a graft-to approach (i.e., graft-to-graft-to).

Where the reactive functional groups on the polymeric primer, the graft polymeric material, and/or a coupling molecule do not naturally covalently or non-covalently bind, for example, conventional activation/coupling reactions may be employed. Exemplary activating/coupling agents that may be utilized in this regard include sulfonyl chloride, carbodiimides (such as N,N'-dicyclohexylcarbodiimide (DCC), N'N-diisopropylcarbodiimide (DIC), 1-ethyl-3-(3-dimethylaminopropyl)carbodiimide (EDC), and 3-diisopropyl-carbodiimide (DIPC)), Mukaiyama reagents (e.g., 2-halo-1-alkyl-pyridinium halides) propane phosphonic acid cyclic anhydride (PPACA) and phenyl dichlorophosphates. Other exemplary coupling techniques include the use of Suzuki coupling, boronic acid tethers, hydroboration, and hydrosilation, among others.

In one exemplary embodiment, the functional group(s) on the polymeric primer is/are a primary or secondary amine group(s) and the complimentary functional group(s) on a graft-to polymeric material is/are selected from activated ester (e.g., activated carboxylic esters), aldehyde, alkyl and aryl halide (to couple, e.g., via Buchwald substitutions), anhydride, boronic acid groups (to couple, e.g., via boronic esters), carboxylic acid and ester, DOPA, epoxy (e.g., glycidyl), isocyanate, phosphonic acid and ester, sulfonic acid and ester, and unsaturated groups (e.g. vinyl, acrylate, methacrylate, styrenyl), and combinations thereof. In another exemplary embodiment, the functional group(s) on the polymeric primer is/are a primary or secondary amine group(s) and a graft-from polymerization is initiated on the primary or secondary amine group(s) by a radical initiator for such group(s), or by amine initiation of epoxide or ethyloxazoline polymerizations. In another exemplary embodiment, the functional group(s) on the polymeric primer is/are a primary or secondary amine group(s) and one or more of these groups are connected to a complementary group on the grafted polymer through a tethering group or linker.

In one exemplary embodiment, the functional group(s) on the polymeric primer is/are a tertiary amine group(s) and the complimentary functional group(s) on a graft-to polymeric material is/are selected from halogen, lactone and sultone groups, and combinations thereof. In another exemplary embodiment, the functional group(s) on the polymeric primer is/are a tertiary amine group(s) and a graft-from polymerization is initiated on the tertiary amine group(s) by a radical initiator for such group(s), or by amine initiation of epoxide or ethyloxazoline polymerizations. In another exemplary embodiment, the functional group on the polymeric primer is a tertiary amine group(s) and one or more of these groups are connected to a complementary group on the grafted polymer through a tethering group or linker.

In one exemplary embodiment, the functional group(s) on the polymeric primer is/are a hydroxyl group(s) and the complimentary functional group(s) on a graft-to polymeric material is/are selected from acid chloride, activated ester (e.g., activated carboxylic esters), anhydride, boronic acid group (to couple, e.g., via boronic esters), carboxylic acid, epoxy (e.g., glycidyl), isocyanate, phosphonic acid and ester, silanol, sulfonic acid and ester, and unsaturated groups (e.g. vinyl, acrylate, methacrylate, styrenyl), and combinations thereof. In another exemplary embodiment, the functional group(s) on the polymeric primer is/are hydroxyl group(s) and a graft-from polymerization is initiated on the hydroxyl group(s) by a redox initiator (e.g., Ce(IV) or other metal oxidant), or by another radical initiator for such group(s). In another exemplary embodiment, the functional group(s) on the polymeric primer is/are a hydroxyl group(s) and one or more of these groups are connected to a complementary group on the grafted polymer through a tethering group or linker.

In one exemplary embodiment, the functional group(s) on the polymeric primer is/are a thiol group(s) and the complimentary functional group(s) on a graft-to polymeric material is/are selected from anhydride, carboxylic acid, epoxy (e.g., glycidyl), isocyanate, silanol, and unsaturated groups (e.g. vinyl, acrylate, methacrylate, styrenyl), and combinations thereof. In another exemplary embodiment, the functional group(s) on the polymeric primer is/are a thiol group(s) and a graft-from polymerization is initiated on the thiol group(s) by a redox initiator (e.g., Ce(IV) or other metal oxidant), or by another radical initiator for such group(s). In another exemplary embodiment, the functional group(s) on the polymeric primer is/are a thiol group(s) and one or more of these groups are connected to a complementary group on the grafted polymer through a tethering group or linker.

In one exemplary embodiment, the functional group(s) on the polymeric primer is/are an epoxy (e.g., glycidyl) group(s) and the complimentary functional group(s) on a graft-to polymeric material is/are selected from anhydride, carboxylic acid, and primary or secondary amine groups, and combinations thereof. In another exemplary embodiment, the functional group(s) on the polymeric primer is/are an epoxy (e.g., glycidyl) group(s) and a graft-from polymerization is initiated on the epoxy (e.g., glycidyl) group(s) by a radical initiator for such group(s). In another exemplary embodiment, the functional group on the polymeric primer is/are an epoxy (e.g., glycidyl) group(s) and one or more of these groups are connected to a complementary group on the grafted polymer through a tethering group or linker.

In one exemplary embodiment, the functional group(s) on the polymeric primer is/are a halogen group(s) and the complimentary functional group(s) on a graft-to polymeric material is/are selected from carboxylic acid and tertiary amine groups, and combinations thereof. In another exemplary embodiment, the functional group(s) on the polymeric primer is/are a halogen group(s) and a graft-from polymerization is initiated on the halogen group(s) by a radical initiator for such group(s), or by ATRP polymerization (such as Cu(I)/bi-pyridine complexes). In another exemplary embodiment, the functional group(s) on the polymeric primer is/are halogen group(s) and one or more of these groups are connected to a complementary group on the grafted polymer through a tethering group or linker.

In one exemplary embodiment, the functional group(s) on the polymeric primer is/are a carboxyl group(s) and the complimentary functional group(s) on a graft-to polymeric material is/are selected from epoxy (e.g., glycidyl), hydroxyl, thiol, primary, secondary or tertiary amines, and unsaturated groups (e.g. vinyl, acrylate, methacrylate, styrenyl), and combinations thereof. In another exemplary embodiment, the functional group(s) on the polymeric primer is/are a carboxyl group(s) and a graft-from polymerization is initiated on the carboxyl group(s) by a radical initiator for such group(s). In another exemplary embodiment, the functional group(s) on the polymeric primer is/are a carboxyl group(s) and one or more of these groups are connected to a complementary group on the grafted polymer through a tethering group or linker.

In one exemplary embodiment, the functional group(s) on the polymeric primer is/are a carboxylic, phosphonic, or sulfonic acid ester, an activated ester, or an acid chloride group(s) and the complimentary functional group(s) on a graft-to polymeric material is/are selected from primary, secondary or tertiary amine, epoxy (e.g., glycidyl), hydroxyl, or thiol groups, and combinations thereof. In another exemplary embodiment, the functional group(s) on the polymeric primer is a carboxylic, phosphonic, or sulfonic acid ester, an activated ester, or an acid chloride group(s) and a graft-from polymerization is initiated on the carboxylic, phosphonic, or sulfonic acid ester, activated ester, or acid chloride group(s) by a radical initiator for such group(s). In another exemplary embodiment, the functional group(s) on the polymeric primer is/are a carboxylic, phosphonic, or sulfonic acid ester, an activated ester, or an acid chloride group(s) and one or more of these groups are connected to a complementary group on the grafted polymer through a tethering group or linker.

In one exemplary embodiment, the functional group(s) on the polymeric primer is/are an alkoxysilane or silanol group(s) and the complimentary functional group(s) on a graft-to polymeric material is/are selected from primary, secondary or tertiary amine, hydroxyl, and silanol groups, and combinations thereof. In another exemplary embodiment, the functional group(s) on the polymeric primer is/are an alkoxysilane or silanol group(s) and a graft-from polymerization is initiated on the alkoxysilane or silanol group(s) by a radical initiator for such group(s). In another exemplary embodiment, the functional group(s) on the polymeric primer is/are an alkoxysilane or silanol group(s) and one or more of these groups are connected to a complementary group on the grafted polymer through a tethering group or linker.

In one exemplary embodiment, the functional group(s) on the polymeric primer is/are an isocyanate group(s) and the complimentary functional group(s) on a graft-to polymeric material is/are selected from primary, secondary or tertiary amine, hydroxyl, and silanol groups, and combinations thereof. In another exemplary embodiment, the functional group(s) on the polymeric primer is/are an isocyanate group(s) and a graft-from polymerization is initiated on the isocyanate group(s) by a radical initiator for such group(s). In another exemplary embodiment, the functional group(s) on the polymeric primer is/are an isocyanate group(s) and one or more of these groups are connected to a complementary group on the grafted polymer through a tethering group or linker.

In one exemplary embodiment, the functional group(s) on the polymeric primer is/are unsaturated group(s) (e.g. vinyl, acrylate, methacrylate, styrenyl) and the complimentary functional group(s) on a graft-to polymeric material is/are selected from primary, secondary or tertiary amine, hydroxyl, and thiol groups, and combinations thereof, boronic acid or acid chloride groups, or diene groups. In another exemplary embodiment, the functional group(s) on the polymeric primer is/are unsaturated group(s) (e.g. vinyl, acrylate, methacrylate, styrenyl) and a graft-from polymerization is initiated on the unsaturated group(s) (e.g. vinyl, acrylate, methacrylate, styrenyl) by a radical initiator for such group(s). In another exemplary embodiment, the functional group(s) on the polymeric primer is/are unsaturated group(s) (e.g. vinyl, acrylate, methacrylate, styrenyl) and one or more of these groups are connected to a complementary group on the grafted polymer through a tethering group or linker.

In one exemplary embodiment, the functional group(s) on the polymeric primer is/are azide group(s) and the complimentary functional group(s) on a graft-to polymeric material is/are alkyne groups, and combinations thereof. In another exemplary embodiment, the functional group(s) on the polymeric primer is/are azide group(s) and a graft-from polymerization is initiated on the azide group(s) by a radical initiator for such group(s). In another exemplary embodiment, the functional group(s) on the polymeric primer is/are azide group(s) and one or more of these groups are connected to a complementary group on the grafted polymer through a tethering group or linker.

In one exemplary embodiment, the functional group(s) on the polymeric primer is/are aldehyde group(s) and the complimentary functional group(s) on a graft-to polymeric material is/are selected from primary, secondary or tertiary amine, hydroxyl, and thiol groups, and combinations thereof. In another exemplary embodiment, the functional group(s) on the polymeric primer is/are aldehyde group(s) and a graft-from polymerization is initiated on the aldehyde group(s) by a radical initiator for such group(s), or by condensation with phenols. In another exemplary embodiment, the functional group(s) on the polymeric primer is/are aldehyde group(s) and one or more of these groups are connected to a complementary group on the grafted polymer through a tethering group or linker.

In one exemplary embodiment, the functional group(s) on the polymeric primer is/are alkyne group(s) and the complimentary functional group(s) on a graft-to polymeric material is/are selected from alkyne groups, and combinations thereof. In another exemplary embodiment, the functional group(s) on the polymeric primer is/are alkyne group(s) and a graft-from polymerization is initiated on the alkyne group(s) by a radical initiator for such group(s). In another exemplary embodiment, the functional group(s) on the polymeric primer is/are alkyne group(s) and one or more of these groups are connected to a complementary group on the grafted polymer through a tethering group or linker.

In one exemplary embodiment, the functional group(s) on the polymeric primer is/are peroxide group(s) and the complimentary functional group(s) on a graft-to polymeric material is/are selected from heat-reactive polyhydrocarbon groups, and combinations thereof. In another exemplary embodiment, the functional group(s) on the polymeric primer is/are peroxide group(s) and a graft-from polymerization is initiated on the peroxide group(s) by a radical initiator for such group(s). In another exemplary embodiment, the functional group(s) on the polymeric primer is/are peroxide group(s) and one or more of these groups are connected to a complementary group on the grafted polymer through a tethering group or linker.

In one exemplary embodiment, the functional group(s) on the polymeric primer is/are photo-initiator group(s) and the complimentary functional group(s) on a graft-to polymeric material is/are selected from UV-reactive polyhydrocarbon groups, and combinations thereof. In another exemplary embodiment, the functional group(s) on the polymeric primer is/are photo-initiator group(s) and a graft-from polymerization is initiated on the photo-initiator group(s) by a radical initiator for such group(s). In another exemplary embodiment, the functional group(s) on the polymeric primer is/are photo-initiator group(s) and one or more of these groups are connected to a complementary group on the grafted polymer through a tethering group or linker.

Preferred embodiments are substrates that are primed with hydroxyl containing polymeric primers. Particularly preferred embodiments consist of primers with pendent or tethered hydroxyalkyl groups; and polyhydroxyalkyl groups, including 1,2-bishydroxyalkyl group, 1,2,3-trihydroxyalkyl, 1,2,3,4-tetrahydroxyalkyl, 1,2,3,4,5-pentahydroxyalkyl, and the 1,2,3,4,5,6-hexahydroxyalkyl; hydroxyl terminated oligoethyleneoxide groups, and alkoxy terminated oligoethyleneoxide groups, caboxymethylamino groups, and polysaccharides.

In one preferred embodiment, the primer is a copolymer of lauryl methacrylate (LMA, 0-50 mol %), 2-hydroxypropyl methacrylate (HPMA, 0-50 mol %) and 3-(trimethoxysilyl)propyl methacrylate (0-25 mol %), and optionally other co-monomers. In one embodiment, the primer may be applied by dipping in a solution from 1-20 wt % in methanol or ethanol and optionally cured at 25° C.-60° C. for 1-48 hours.

A particular feature of the present invention is the graft-from polymerization of primed substrates. In particular, the Ce(IV) promoted graft-from polymerization of olefinic monomers, especially carboxylammonium monomers, and sulfoammonium monomers. Preferred conditions include Ce(IV) promoted grafting using cerric ammonium nitrate, or cerric ammonium sulfate in aqueous solutions. It is preferred also that the Ce(IV) graft polymerization solutions be slightly acidic at pH from 0-5. This can be achieved by the addition of acids, including hydrochloric acid, sulfuric acid, and nitric acid. Without being bound to theory, it is thought that slightly acidic conditions increase the efficiency of radical generation from the hydroxyl containing surface.

The efficiency of the Ce(IV) grafting can be adjusted by altering the time, temperature, and concentration monomers and of grafting reagents, and additives (e.g., inorganic salts). Times from 1 h to 24 hours are preferred; more preferred is 4-8 hour grafting time. In particular, temperatures from 25° C.-100° C. are preferred. More preferential, are temperatures from 40° C.-70° C.

In another preferred embodiment primed substrates may be post-modified. In particularly, primed substrates are post modified to install initiator groups chemically. A preferred embodiment is the post modification of primed surfaces to install radical initiating sites including alkyl halides. A preferred example is modifications that introduce the atom transfer initiating group bromoacetylbromide. This can be done, for example, by treatment with bromoisobutyrylbromide in the presence of base. The resulting embodiment, an ATRP initiator primed substrate, in the presence of copper(I) bromide and amine ligands, can graft olefinic monomers in a controlled fashion. Preferred monomers are carboxylammonium monomers and carboxylammonium monomers.

The efficiency of the ATRP grafting can be adjusted by altering the time, temperature, and concentration of monomers and of grafting reagents, and additives (e.g., inorganic salts). Times from 1 h to 24 hours are preferred; more preferred is 4-8 hour grafting time. In particular, temperatures from 0° C.-60° C. are preferred. More preferential, are temperatures from 0° C.-25° C.

In one preferred embodiment, the primer is a copolymer of 2-aminoethyl methacrylate (AEMA, 20-80 mol %), lauryl methacrylate (LMA, 0-50 mol %), 2-hydroxypropyl methacrylate (HPMA, 0-50 mol %) and 3-(trimethoxysilyl)propyl methacrylate (TMOSMA, 0-25 mol %), and optionally other co-monomers. The grafted polymer is a copolymer of with carboxybetaine methacrylate (CBMA, 25-80 mol %), glycidyl methacrylate (GMA, 10-50 mol %), and 2-hydroxypropyl methacrylate (HPMA, 0-50 mol %). In one embodiment, the primer is applied to substrate by dipping in a solution from 0.5-20 wt % in ethanol and optionally cured at room temperature to 100° C. for 0.2-24 hours. Preferably, the grafted polymer is then applied by dipping in a solution from 0.5-20 wt % in water, and curing at room temperature to 100° C. for 0.2-48 hours.

In another preferred embodiment, the primer is a copolymer of 2-aminoethyl acrylamide (AEAA, 20-80 mol %), lauryl acrylamide (LAA, 0-50 mol %), 2-hydroxypropyl acrylamide (HPAA, 0-50 mol %) and 3-(trimethoxysilyl)propyl acrylamide (TMOSAA, 0-25 mol %). The grafted polymer is a copolymer of with carboxybetaine acrylamide (CBAA, 25-80 mol %), glycidyl acrylamide (GAA, 10-50 mol %), and 2-hydroxypropyl acrylamide (HPAA, 0-50 mol %). In one embodiment, the primer is applied to substrate by dipping in a solution from 0.5-20 wt % in ethanol and optionally cured at room temperature to 100° C. for 0.2-24 hours. Preferably, the grafted polymer is then applied by dipping in a solution from 0.5-20 wt % in water, and curing at room temperature to 100° C. for 0.2-48 hours.

In another preferred embodiment, the primer is a copolymer of AEMA (20-80 mol %) and LMA (80-20 mol %), The grafted polymer is a copolymer of with sulfobetaine methacrylate (SBMA, 25-90 mol %) and GMA (75-10 mol %). In one embodiment, the primer is applied to substrate by dipping in a solution from 0.5-20 wt % in ethanol and optionally cured at room temperature to 100° C. for 0.2-24 hours. Preferably, the grafted polymer is then applied by dipping in a solution from 0.5-20 wt % in water, and curing at room temperature to 100° C. for 0.2-48 hours.

In another preferred embodiment, the primer is a copolymer of styrene (10-90%) and maleic anhydride (SMA) (90-10 mol %). The grafted polymer is a copolymer of with SBMA (25-90 mol %) and AEMA (75-10 mol %). In one embodiment, the primer is applied to substrate by dipping in a solution from 0.5-20 wt % in toluene and optionally cured at room temperature to 100° C. for 0.2-24 hours. Preferably, the grafted polymer is then applied by dipping in a solution from 0.5-20 wt % in water, and curing at room temperature to 100° C. for 0.2-48 hours.

In another preferred embodiment, the primer is a copolymer of LMA (10-90%) and isocyanate methacrylate (IMA, 90-10 mol %). The grafted polymer is a copolymer of with SBMA (25-90 mol %) and AEMA (75-10 mol %). In one embodiment, the primer is applied to substrate by dipping in a solution from 0.5-20 wt % in ethanol and optionally cured at room temperature to 100° C. for 0.2-24 hours. Preferably, the grafted polymer is then applied by dipping in a solution from 0.5-20 wt % in water, and curing at room temperature to 100° C. for 0.2-48 hours.

In another embodiment, the primer and grafted polymers are coupled with a linker or a crosslinking agent. In one preferred embodiment, the primer is a copolymer of LMA (10-90%) and HPMA (90-10%), and optionally other co-monomers. The grafted polymer is a copolymer of SBMA (25-90 mol %) and HPMA (75-10%), and optionally other co-monomers. The crosslinking agent is glutaraldehyde. In one embodiment, the primer is applied to substrate by dipping in a solution from 0.5-20 wt % in ethanol and optionally cured at room temperature to 60° C. for 0.2-5 hours. Preferably, the grafted polymer is then applied by dipping in a solution from 0.5-20 wt % in water, together with a glutaraldehyde concentration of 0.1-50 wt %, and curing at room temperature to 100° C. for 0.2-48 hours.

In one preferred embodiment, the primer is a copolymer of LMA (0-50 mol %), HPMA (0-50 mol %) and TMOSMA (0-25 mol %), and optionally other co-monomers. The grafted polymer is a copolymer of with SBMA (25-90 mol %) and HPMA (75-10%), and optionally other co-monomers. The crosslinking agent is tetraethyl silicate. In one embodiment, the primer is applied to substrate by dipping in a solution from 0.5-20 wt % in ethanol and optionally cured at room temperature to 60° C. for 0.2-5 hours. Preferably, the surface is then dipped with a tetraethyl silicate of 0.1-10 wt % in ethanol, and optionally cured at room temperature to 60° C. for 0.2-5 hours. Preferably, the grafted polymer is then applied by dipping in a solution from 0.5-20 wt % in water, and curing at room temperature to 100° C. for 0.2-48 hours.

In one particular embodiment, the polymeric primer comprises a functional group selected from glycidyl, isocyanate, primary amine, benzophoneone, and bromoisobutyryl groups, and combinations thereof. In one particular embodiment, the grafted polymer comprises a functional group selected from primary amine, carboxylic, and SBMA homopolymer groups, and combinations thereof. In combination, in one embodiment the polymeric primer comprises a glycidyl group and the grafted polymer comprises a primary amine group. In another embodiment, the polymeric primer comprises an isocyanate group and the grafted polymer comprises a primary amine group. In another embodiment, the polymeric primer comprises a primary amine group and the grafted polymer comprises a carboxylic group. In another embodiment, the polymeric primer comprises a benzophoneone group and the grafted polymer comprises an SBMA homopolymer group. In another embodiment, the polymeric primer comprises a bromoisobutyryl group and the grafted polymer comprises an SBMA homopolymer group.

Independent of whether graft-from or graft-to methods are used, grafted polymers can be formed by synthetic means known in the art including, but not limited to, free radical polymerization (e.g., thermal, UV, and/or redox), ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET).

The grafted polymer may comprise any of a range of polymer types or combinations thereof. The polymer backbone may be neutral (e.g., polyalkylene or polyether) or contain permanently charged moieties (e.g., cyclic or acyclic quaternized nitrogen atoms), or even zwitterionic backbones (e.g., phosphorylcholine backbones). In one embodiment, therefore, the non-fouling polymeric material comprises a polymer or copolymer selected from the group consisting of polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, hydrocarbon, ether-ester, ether-amide or ionized polyethylene and combinations thereof.

The polymer may also contain a wide range of pendant (side-chain) groups, hydrophilic and hydrophobic, neutral, anionic, cationic, or mixed charged. For example, the pendant groups may include neutral hydrophilic groups such as hydroxy, oligo(ethylene glycol) and/or poly(ethylene glycol) moieties, or it may include charged groups such as anionic moieties, cationic moieties, and zwitterionic moieties.

In one embodiment, a polymer is synthesized, for example, in solution, and the presynthesized polymer is grafted to a substrate to which a polymeric primer has been applied. Alternatively, the polymer may be grown, in situ, from the polymeric primer. In each instance, however, the polymer is attached to the polymeric primer by means of a functional group present in the polymeric primer covalently or non-covalently (e.g., by hydrogen bonding, ionic bonding, static forces, van der Waals interactions, combinations thereof, or the like), or a combination thereof. In a preferred embodiment, the polymer is grafted to or grafted from the polymeric primer by covalent bonding with the functional group(s) of the polymeric primer.

Preferably, the non-fouling polymeric material that is grafted from the substrate comprises a chain-growth polymer (that is, a polymer or polymer block formed by addition polymerization), or a combination thereof. The chain-growth polymer may be, for example, an addition polymer derived from monomer(s) incorporating double or triple bonds, e.g., an olefin. By way of further example, the chain-growth polymer may comprise an addition polymer derived from a cyclic monomer by means of a ring-opening polymerization reaction. Thus, the polymer may be a chain-growth homopolymer or copolymer. In a preferred embodiment, the polymer is a chain growth addition homopolymer or a chain growth addition copolymer comprising the residue of two or more monomers.

In accordance with one aspect of the present invention, it is generally preferred that the non-fouling polymeric material be prepared without inordinate use of a polyfunctional crosslinking agent. For example, it is generally preferred that the non-fouling polymeric material contain less than 50 mole/0 of the residue of a polyvalent crosslinker. In one such embodiment, the non-fouling polymeric material contains less than 25 mole % of the residue of a polyvalent crosslinker. In one such embodiment, non-fouling polymeric material contain less than 10 mole % of a polyvalent crosslinker. In one such embodiment, the non-fouling polymeric material contains less than 5 mole % of the residue of a polyvalent crosslinker. In one such embodiment, non-fouling polymeric material contain less than 3 mole % of a polyvalent crosslinker. In one such embodiment, the non-fouling polymeric material contains less than 0.1 mole % of the residue of a polyvalent crosslinker. In one such embodiment, the non-fouling polymeric material contains no residue of a polyvalent crosslinker.

Through grafting, step-growth or chain-growth techniques, the non-fouling polymeric material may comprise any of a range of polymer types or combinations thereof. The polymer backbone may be neutral (e.g., polyalkylene or polyether) or contain permanently charged moieties (e.g., cyclic or acyclic quaternized nitrogen atoms), or even zwitterionic backbones (e.g., phosphorylcholine backbones). In one embodiment, therefore, the non-fouling polymeric material comprises a polymer or copolymer selected from the group consisting of polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, hydrocarbon, ether-ester, ether-amide or ionized polyethylene and combinations thereof.

The polymer may also contain a wide range of pendant (side-chain) groups, hydrophilic and hydrophobic, neutral, anionic, cationic, or mixed charged. For example, the pendant groups may include neutral hydrophilic groups such as hydroxy, oligo(ethylene glycol) and/or poly(ethylene glycol) moieties, or it may include charged groups such as anionic moieties, cationic moieties, and zwitterionic moieties.

Zwitterionic Groups

Zwitterions are molecules that carry formal positive and negative charges on non-adjacent atoms within the same molecule and molecules that may be ionized by addition or removal of an electrophile or a nucleophile, or by removal of a protecting group. Both natural and synthetic polymers, containing zwitterion functionality, have been shown to resist protein adhesion. In one embodiment, the zwitterionic monomer contains a phosphorylcholine moiety, a carboxyammonium moiety, a sulfoammonium moiety, derivatives thereof, or combinations thereof. In one embodiment, the zwitterionic monomer contains a carboxyammonium moiety, a sulfoammonium moiety, derivatives thereof, or combinations thereof. In one embodiment, the zwitterionic monomer contains a sulfobetaine moiety or a carboxybetaine moiety. The zwitterionic polymer may be formed by initiating polymerization with radicals present in the polymeric substrate, in the presence of one or more monomers, such as sulfobetaine methacrylate or carboxybetaine methacrylate monomers.

Polysulfoammonium polymers such as polysulfobetaines, polycarboxyammonium polymers such as polycarboxybetaines and other natural and synthetic zwitterion chemistries can be used to design non-fouling materials for the biomedical applications described herein. Some examples of natural zwitterions chemistries that could be used for non-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create non-fouling materials, include, but are not limited to, amino-carboxylic acids (carboxybetaines), amino-sulfonic acids (sulfo betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, or at the terminal groups.

Materials containing, or composed of, these natural or synthetic zwitterions, can be grafted from surfaces, particularly the surfaces of medical devices, in order to improve biocompatibility, reduce thrombogenesis (such as on the surface of stents or venous valves), and reduce fouling by proteins or bacteria present in solution. This is particularly applicable for surfaces where non-specific binding of proteins in solution could negatively impact the desired or necessary mechanics of a device.

In one embodiment, the non-fouling polymer contains zwitterionic pendant groups covalently attached, directly or indirectly to the polymer back bone. The zwitterionic pendant groups may have an overall net charge, for instance, by having a divalent center of anionic charge and monovalent center of cationic charge or vice versa, or by having two centers of cationic charge and one center of anionic charge or vice versa. Preferably, however, the zwitterion has no overall net charge and most preferably has a center of monovalent cationic charge and a center of monovalent anionic charge. Additionally, the center(s) of cationic charge are preferably permanent; that is, it is preferably a quaternary nitrogen, quaternary phosphonium or tertiary sulfonium group. Additionally, the center(s) of anionic charge are also permanent; that is, they are completely ionized at physiological pH and are preferably carboxylate, phosphate, phosphonic, phosphonate, sulfate, sulfinic, or sulfonate.

In another embodiment, the polymer contains zwitterionic pendant groups covalently attached, directly or indirectly, to the polymer back bone, and the zwitterion corresponds to Formula ZI-3:

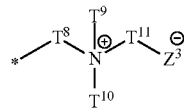

Formula ZI-3 wherein $T^8$ is a bond, hydrocarbylene, substituted hydrocarbylene, heterocyclo, or in combination with $T^9$ and $T^{10}$ and the nitrogen atom to which they are attached form a nitrogen-containing heteroaromatic ring, $T^9$ and $T^{10}$ are independently hydrogen, hydrocarbyl, substituted hydrocarbyl or heterocyclo, or, $T^9$ and $T^{10}$, in combination with $T^8$ and the nitrogen atom to which they are attached form a nitrogen-containing heteroaromatic ring, $T^{11}$ is hydrocarbylene, substituted hydrocarbylene, ether, or oxylated alkylene, $Z^3$ is carboxylate, phosphate, phosphonic, phosphonate, sulfate, sulfinic, or sulfonate, and

* designates the point of covalent attachment, direct or indirect, of the zwitterion of Formula ZI-3 to the polymer backbone.

In certain preferred embodiments in which the polymer contains zwitterionic pendant group corresponding to Formula ZI-3, $T^8$, $T^9$, $T^{10}$, and $T^{11}$ are selected from a more narrow range of substituents, $Z^3$ is carboxylate or sulfate, and the zwitterion corresponds to Formula ZI-4:

Formula ZI-4

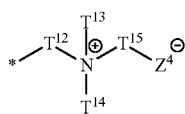

wherein * designates the point of covalent attachment, direct or indirect, of the zwitterion of Formula ZI-4 to the polymer backbone; $T^{12}$ is a bond or —$(CH_2)_m$— with m being 1 to 3; $T^{13}$ and $T^{14}$ are independently hydrogen, alkyl, or substituted alkyl; $T^{15}$ is optionally substituted alkylene, phenylene, ether, or oxylated alkylene; and $Z^4$ is carboxylate or sulfate. For example, in this embodiment, $T^{13}$ and $T^{14}$ may independently be hydrogen or lower alkyl, e.g., methyl, ethyl, or propyl. By way of further example, in this embodiment, $T^{13}$ and $T^{14}$ may independently be hydrogen or lower alkyl, e.g., methyl, ethyl, or propyl. By way of further example, in this embodiment, $T^{15}$ may be —$(CH_2)_n$— with n being 1-8. By way of further example, in this embodiment, $T^{15}$ may be —$(CH_2)_2$— or —$(CH_2)_3$— and $T^{13}$ and $T^{14}$ may be methyl. By way of further example, in this embodiment, $T^{15}$ may be —$(CH_2)_2$— or —$(CH_2)_3$—, $T^{13}$ and $T^{14}$ may be hydrogen or alkyl. By way of further example, in this embodiment, $T^{12}$ may be —$(CH_2)_2$—, $T^{13}$ and $T^{14}$ may be methyl, $T^{15}$ may be —$(CH_2)_2$— and $Z^4$ may be carboxylate. By way of further example, in this embodiment, $T^{12}$ may be —$(CH_2)_2$—, $T^{13}$ and $T^{14}$ may be methyl, $T^{15}$ may be —$(CH_2)_3$— and $Z^4$ may be sulfate.

In certain preferred embodiments in which the polymer contains zwitterionic pendant group corresponding to Formula ZI-3, $T^8$, $T^9$ and $T^{10}$ and the nitrogen atom to which they are attached form a nitrogen-containing heteroaromatic ring. For example, $T^8$, $T^9$ and $T^{10}$ and the nitrogen atom to which they are attached may form an optionally substituted heterocycle, containing a quaternary nitrogen atom. One such embodiment corresponds to Formula ZI-5:

Formula ZI-5

wherein * designates the point of covalent attachment, direct or indirect, of the zwitterion of Formula ZI-5 to the polymer backbone; is part of a heterocyclic structure, $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate. Exemplary zwitterions corresponding to Formula ZI-5 include zwitterions corresponding to Formulae ZI-6A and ZI-6B:

Formula ZI-6A

Formula ZI-6B

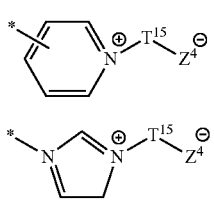

wherein * designates the point of covalent attachment, direct or indirect, of the zwitterion of Formulae ZI-6A and ZI-6B to the polymer backbone; $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate.

In one embodiment, the polymer contains zwitterionic pendant groups covalently attached, directly or indirectly, to the polymer back bone, and the zwitterion corresponds to Formula ZI-7

Formula ZI-7

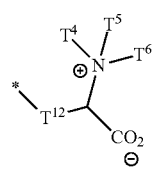

wherein $T^4$, $T^5$ and $T^6$ are independently hydrogen, hydrocarbyl, substituted hydrocarbyl or heterocyclo; $T^{12}$ is a bond, hydrocarbylene, substituted hydrocarbylene, or heterocyclo, and * designates the point of covalent attachment, direct or indirect, of the zwitterion of Formula ZI-7 to the polymer backbone.

In one embodiment, the polymer contains zwitterionic pendant groups covalently attached, directly or indirectly, to the polymer back bone, and the zwitterion corresponds to Formula ZI-1:

Formula ZI-1

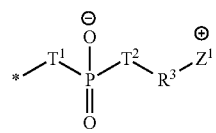

wherein $T^1$ and $T^2$ are independently oxygen, sulfur, NH or a bond, $T^3$ is hydrocarbylene, substituted hydrocarbylene, ether, or oxylated alkylene, $Z^1$ is a moiety comprising a quaternary nitrogen, phosphonium or sulfonium cationic group, and

* designates the point of covalent attachment, direct or indirect, of the zwitterion of Formula ZI-1 to the polymer backbone.

In certain preferred embodiments in which the polymer contains zwitterionic pendant group corresponding to Formula ZI-1, $T^1$ and $T^2$ are oxygen, $Z^1$ is quaternary nitrogen, and the zwitterion corresponds to Formula ZI-2:

Formula ZI-2

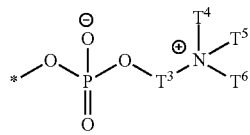

wherein * designates the point of covalent attachment of the zwitterion of Formula ZI-2 to the polymer backbone, $T^3$ is hydrocarbylene, substituted hydrocarbylene, or oxylated alkylene, and $T^4$, $T^5$ and $T^6$ are independently hydrogen, hydrocarbyl, substituted hydrocarbyl or heterocyclo. For example, in this embodiment, $T^3$ may be —$(CH_2)_n$— with n being 1-8. By way of further example, in this embodiment, $T^4$, $T^5$ and $T^6$ may independently be lower alkyl, e.g., methyl, ethyl or propyl. By way of further example, in this embodiment, $T^3$ may be —$(CH_2)_n$— with n being 1-3, and $T^4$, $T^5$ and $T^6$ may independently be lower alkyl, e.g., methyl, ethyl or propyl. By way of further example, in this embodiment, $T^3$ may be —$(CH_2)_n$— with n being 1-3, and one or more of $T^4$, $T^5$ and $T^6$ may be substituted hydrocarbyl such as oligomeric phosphorylcholine (e.g., Formula 9).

Neutral Hydrophilic Pendant Groups

In one embodiment, the polymer contains neutral hydrophilic pendant groups covalently attached, directly or indirectly, to the polymer backbone. Exemplary neutral hydrophilic groups include hydroxy, thiol, oxylated alkyls (e.g., oligoethylene glycol, polyethylene glycol and/or polypropylene glycol), ether, thioether, and the like. In one such specific embodiment, the polymer contains pendant groups comprising alkoxylated moieties corresponding to Formula POA-1:

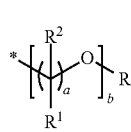

Formula POA-1 wherein a is 1-3, b is 1-8, each $R^1$ and $R^2$ is independently selected from the group consisting of hydrogen, halogen, and optionally substituted lower alkyl, $R^3$ is hydrocarbyl, substituted hydrocarbyl or heterocyclo, and * designates the point of attachment of the moieties corresponding to Formula POA-1 to the remainder of the pendant group and the backbone. By way of example, in one such embodiment, each $R^1$ and $R^2$ are hydrogen, n is 2 or 3. By way of further example, in one such embodiment, each $R^1$ and $R^2$ is hydrogen, n is 2 or 3, and b is 3-5. By way of further example, in one such embodiment, each $R^1$ and $R^2$ is hydrogen, n is 2 or 3, b is 3-5, and $R^3$ is alkyl. In one embodiment, the repeat units are derived from macromonomers containing 2-20 alkylene oxide units.

Repeat Units

In general, homopolymers or copolymers comprising zwitterionic pendant groups, neutral hydrophilic pendant groups, cationic pendant groups and/or anionic pendant groups may be prepared by polymerization of any of a wide range of monomers. In one preferred embodiment, the non-fouling polymeric material is a homopolymer or copolymer comprising repeat units derived from an olefinic monomer. Thus, for example, in one embodiment the non-fouling polymeric material comprises repeat units derived from an olefinic monomer and corresponding to Formula 1:

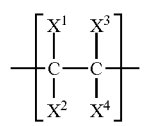

Formula 1 wherein $X^1$ and $X^2$ are independently hydrogen, hydrocarbyl, substituted hydrocarbyl, heterocyclo, or substituted carbonyl, provided, however, $X^1$ and $X^2$ are not each selected from the group consisting of aryl, heteroaryl, and heterosubstituted carbonyl, $X^3$ is hydrogen, alkyl or substituted alkyl, $X^4$ is -$OX^{40}$, —$NX^{41}X^{42}$, —$SX^{40}$, aryl, heteroaryl or acyl, $X^{40}$ is hydrogen, hydrocarbyl, substituted hydrocarbyl, heterocyclo or acyl, and $X^{41}$ and $X^{42}$ are independently hydrogen, hydrocarbyl, substituted hydrocarbyl or heterocyclo.

In certain embodiments in which the non-fouling polymeric material comprises repeat units corresponding to Formula 1, it is preferred that $X^4$ of at least a fraction of the repeat units comprise alkoxylated moieties, zwitterionic moieties, anionic moieties, or cationic moieties. In such embodiments, for example, $X^1$ and $X^2$ may be hydrogen, and the polymer comprises repeat units corresponding to Formula 2:

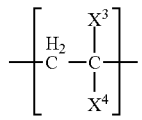

Formula 2 wherein $X^3$ is hydrogen, alkyl or substituted alkyl, and $X^4$ is a pendant group comprising an oxylated alkylene moiety, a zwitterionic moiety, an anionic moiety, or a cationic moiety. For example, $X^3$ may be hydrogen or lower alkyl. By way of further example, $X^4$ may be a pendant group comprising an oxylated alkylene moiety corresponding to Formula POA-1. By way of further example, the repeat unit of Formula 2 may be zwitterionic repeat unit comprising a zwitterionic moiety corresponding to Formula ZI-1, ZI-2, ZI-3, ZI-4, ZI-5, ZI-6A, ZI-6B, or ZI-7. By way of further example, the repeat unit of Formula 2 may be a cationic repeat unit. By way of further example, the repeat unit of Formula 2 may be an anionic repeat unit. By way of further example, $X^3$ may be hydrogen or methyl and $X^4$ may be a pendant group comprising an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7.

In one presently preferred embodiment, the non-fouling polymeric material comprises repeat units corresponding to Formula 2 wherein $X^4$ is acyl and the repeat units correspond to Formula 3:

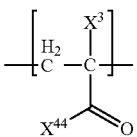

Formula 3 wherein $X^{44}$ comprises an oxylated alkylene moiety, a zwitterionic moiety, an anionic moiety, or a cationic moiety. For example, $X^{44}$ may be —$OX^{45}$, —$NX^{45}X^{46}$ or —$SX^{45'}$, wherein $X^{45}$ is a substituted hydrocarbyl or heterocyclo moiety comprising an oxylated alkylene moiety, a zwitterionic moiety, an anionic moiety, or a cationic moiety, and $X^{46}$ is hydrogen, hydrocarbyl, substituted hydrocarbyl or heterocyclo. For example, $X^3$ may be hydrogen or lower alkyl. By way of further example, $X^{44}$ may be $-OX^{45}$, or $-NHX^{45}$. By way of further example, $X^{44}$ may be $-OX^{45}$, or $-NHX^{45}$ wherein $X^{45}$ comprises an oxylated alkylene moiety corresponding to Formula POA-1. By way of further example, $X^{44}$ may be $-OX^{45}$, or $-NHX^{45}$ wherein $X^{45}$ comprises a zwitterionic moiety corresponding to Formula ZI-1, ZI-2, ZI-3, ZI-4, ZI-5, ZI-6A, ZI-6B, or ZI-7. By way of further example, the repeat unit of Formula 3 may be a cationic repeat unit. By way of further example, the repeat unit of Formula 3 may be an anionic repeat unit. By way of further example, $X^3$ may be hydrogen or methyl and $X^{44}$ may comprise an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7. In one particularly preferred embodiment, the polymer contains repeat units corresponding to Formula 3 and $X^{44}$ is $-O(CH_2)_2N^+(CH_3)_2(CH_2)_nSO_3-$, $-O(CH_2)_2N^+(CH_3)_2(CH_2)_nCO_2$, $-NH(CH_2)_3N^+(CH_3)_2(CH_2)_nCO_2$, or $-NH(CH_2)_3N^+(CH_3)_2(CH_2)_nSO_3$, wherein n is 1-8. In one embodiment, the polymer contains repeat units corresponding to Formula 3 and $X^{44}$ is $-NH(CH_2)_mN(CH_2)_nCH_3(CH_2)_pSO_3$, $-NH(CH_2)_mN(CH_2)_nCH_3(CH_2)_pCO_2$, $-NH(CH_2)_mN^+[(CH_2)_nCH_3]_2(CH_2)_pSO_3$, $-NH(CH_2)N^+[(CH_2)_nCH_3]_2(CH_2)_pCO_2$, $-NH(CH_2)_mNcyclo-(CH_2)_pCO_2$, or $-NH(CH_2)_mNcyclo-(CH_2)_pSO_3$, (Ncyclo is a heterocyclic structure or a heterocyclic derivative containing at least one nitrogen element), wherein m is 1-8; n is 0-5; and p is 1-8. In one embodiment, the polymer contains repeat units corresponding to Formula 3 and $X^{44}$ is $-O(CH_2)_mN(CH_2)_nCH_3(CH_2)_pSO_3$, $-O(CH_2)_mN(CH_2)_nCH_3(CH_2)_pCO_2$, $-O(CH_2)_mN^+[(CH_2)_nCH_3]_2(CH_2)_pSO_3$, $-O(CH_2)N^+[(CH_2)_nCH_3]_2 (CH_2)_pCO_2$, $-O(CH_2)_mNcyclo-(CH_2)_pCO_2$, or $-O(CH_2)_mNcyclo-(CH_2)_pSO_3$ wherein m is 1-8; n is 0-5; and p is 1-8. In one embodiment, the polymer contains repeat units corresponding to Formula 3 and $X^{44}$ is $-O(CH_2)_2N^+(CH_3)_2(CH_2)_3SO_3$, $-O(CH_2)_2N^+(CH_3)_2(CH_2)_2CO_2$, $-NH(CH_2)_2N^+(CH_3)_2(CH_2)_3SO_3$, $-NH(CH_2)_2N^+(CH_3)_2(CH_2)_2CO_2$, $-NH(CH_2)_3N^+(CH_3)_2(CH_2)_3SO_3$, $-NH(CH_2)_3N^+(CH_3)_2(CH_2)_2CO_2$, $-O(CH_2)_2N^+(CH_2CH_3)_2(CH_2)_3SO_3$, $-O(CH_2)_2N^+(CH_2CH_3)_2(CH_2)_2CO_2$, $-O(CH_2)_2N^+(CH_2CH_2CH_2CH_3)_2(CH_2)_3SO_3$, $-O(CH_2)_2N^+(CH_2CH_2CH_2CH_3)_2(CH_2)_2CO_2$ or $-NH(CH_2)_3Ncyclo-(CH_2)_3SO_3$ In one preferred embodiment, the non-fouling polymeric material is a zwitterionic polymer or copolymer. For example, the non-fouling polymeric material may comprise carboxybetaine repeat units and/or sulfobetaine repeat units. Alternatively, the non-fouling polymeric material may be a polyampholyte, containing anionic and cationic repeat units. Optionally, the non-fouling polymer may contain poly(ethylene oxide) repeat units and/or other neutral olefinic repeat units. Thus, for example, in one preferred embodiment, the non-fouling polymeric material is a zwitterionic polymer or copolymer comprising the repeat units of Formula 4:

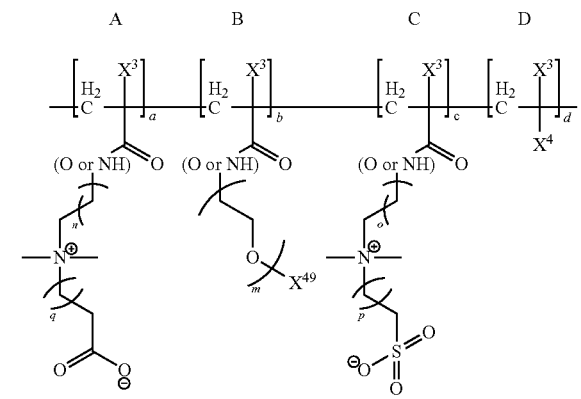

Formula 4 a is 0-1; b is 0-1; c is 0-1; d is 0-1; m is 1-20; n and o are independently 0-11; p and q are independently 0-11; $X^3$ is hydrogen, alkyl or substituted alkyl, $X^4$ is $-OX^{40}$, $-NX^{41}X^{42}$, $-SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, provided the sum of a, b, c and d is greater than 0 and $X^4$ of repeat unit D differs from the corresponding pendant group of repeat units A, B and C. In one such embodiment, $X^3$ is hydroxy-substituted alkyl such as hydroxypropyl.

In one embodiment, it is preferred that the non-fouling polymeric material is a zwitterionic polymer comprising repeat units corresponding to the A and/or the C repeat units. For example, in one embodiment the sum of a and c is at least 0.1. By way of further example, in one embodiment the sum of a and c is at least 0.2. By way of further example, in one embodiment the sum of a and c is at least 0.3. By way of further example, in one embodiment the sum of a and c is at least 0.4. By way of further example, in one embodiment the sum of a and c is at least 0.5. By way of further example, in one embodiment the sum of a and c is at least 0.6. By way of further example, in one embodiment the sum of a and c is at least 0.7. By way of further example, in one embodiment the sum of a and c is at least 0.8. By way of further example, in one embodiment the sum of a and c is at least 0.9. By way of further example, in one embodiment the sum of a and c is at least 0.1 and b is at least 0.1. By way of further example, in one embodiment the sum of a and c is at least 0.2 and b is at least 0.1. By way of further example, in one embodiment the sum of a and c is at least 0.3 and b is at least 0.1. By way of further example, in one embodiment the sum of a and c is at least 0.4 and b is at least 0.1. By way of further example, in one embodiment the sum of a and c is at least 0.5 and b is at least 0.1. By way of further example, in one embodiment the sum of a and c is at least 0.6 and b is at least 0.1. By way of further example, in one embodiment the sum of a and c is at least 0.7 and b is at least 0.1. By way of further example, in one embodiment the sum of a and c is at least 0.8 and b is at least 0.1. By way of further example, in one embodiment the sum of a and c is at least 0.9 and b is at least 0.1. By way of further example, in one embodiment the sum of a and c is at least 0.1 and d is at least 0.1. By way of further example, in one embodiment the sum of a and c is at least 0.2 and d is at least 0.1. By way of further example, in one embodiment the sum of a and c is at least 0.3 and d is at least 0.1. By way of further example, in one embodiment the sum of a and c is at least 0.4 and d is at least 0.1. By way of further example, in one embodiment the sum of a and c is at least 0.5 and d is at least 0.1. By way of further example, in one embodiment the sum of a and c is at least 0.6 and d is at least 0.1. By way of further example, in one embodiment the sum of a and c is at least 0.7 and d is at least 0.1. By way of further example, in one embodiment the sum of a and c is at least 0.8 and d is at least 0.1. By way of further example, in one embodiment the sum of a and c is at least 0.9 and d is at least 0.1. By way of further example, in one embodiment the sum of a and c is at least 0.1, b is at least 0.1 and d is at least 0.1. By way of further example, in one embodiment the sum of a and c is at least 0.2, b is at least 0.1 and d is at least 0.1. By way of further example, in one embodiment the sum of a and c is at least 0.3, b is at least 0.1 and d is at least 0.1. By way of further example, in one embodiment the sum of a and c is at least 0.4, b is at least 0.1 and d is at least 0.1. By way of further example, in one embodiment the sum of a and c is at least 0.5, b is at least 0.1 and d is at least 0.1. By way of further example, in one embodiment the sum of a and c is at least 0.6, b is at least 0.1, and d is at least 0.1. By way of further example, in one embodiment the sum of a and c is at least 0.7, b is at least 0.1 and d is at least 0.1. By way of further example, in one embodiment the sum of a and c is at least 0.8, b is at least 0.1 and d is at least 0.1. By way of further example, in one embodiment the sum of a and c is at least 0.9, b is at least 0.1 and d is at least 0.1. In each of these exemplary embodiments, a may be 0, c may be 0, or a and c may each be greater than 0.

In one preferred embodiment, the non-fouling polymeric material is a zwitterionic polymer or copolymer comprising the repeat units of Formula 4, m is 1-8; $X^3$ is hydrogen, alkyl or substituted alkyl, $X^4$ is $-OX^{40}$, $-NX^{41}X^{42}$, $-SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, with the proviso that $X^4$ of the D repeat differs from the corresponding pendant groups of the A, B or C repeat units and a, b, c, and d, in combination, are selected from one of the sets of combinations appearing in Table I:

TABLE I

| Combination | a | b | c | d |
|---|---|---|---|---|
| 1 | 0.1-1.0 | 0.1-0.5 | 0.1-1.0 | 0.1-1.0 |
| 2a | >0 | >0.1 | 0 | 0 |
| 2b | >0 | 0 | 0 | >0.1 |
| 2c | >0 | >0.1 | 0 | >0.1 |
| 3a | >0.1 | >0.1 | 0 | 0 |
| 3b | >0.1 | 0 | 0 | >0.1 |
| 3c | >0.1 | >0.1 | 0 | >0.1 |
| 4a | >0.2 | >0.1 | 0 | 0 |
| 4b | >0.2 | 0 | 0 | >0.1 |
| 4c | >0.2 | >0.1 | 0 | >0.1 |
| 5a | >0.3 | >0.1 | 0 | 0 |
| 5b | >0.3 | 0 | 0 | >0.1 |
| 5c | >0.3 | >0.1 | 0 | >0.1 |
| 6a | >0.4 | >0.1 | 0 | 0 |
| 6b | >0.4 | 0 | 0 | >0.1 |
| 6c | >0.4 | >0.1 | 0 | >0.1 |
| 7a | >0.5 | >0.1 | 0 | 0 |
| 7b | >0.5 | >0 | 0 | >0.1 |
| 7c | >0.5 | >0.1 | 0 | >0.1 |
| 8a | >0.6 | >0.1 | 0 | 0 |
| 8b | >0.6 | 0 | 0 | >0.1 |
| 8c | >0.6 | >0.1 | 0 | >0.1 |
| 9a | >0.7 | >0.1 | 0 | 0 |
| 9b | >0.7 | >0.1 | 0 | >0.1 |
| 9c | >0.7 | 0 | 0 | >0.1 |
| 10a | >0.8 | >0.1 | 0 | 0 |
| 10b | >0.8 | 0 | 0 | >0.1 |
| 10c | >0.8 | >0.1 | 0 | >0.1 |
| 11a | >0.9 | >0.1 | 0 | 0 |
| 11b | >0.9 | 0 | 0 | >0.1 |
| 11c | >0.9 | >0.1 | 0 | >0.1 |
| 12a | 0 | >0.1 | >0 | 0 |
| 12b | 0 | 0 | >0 | >0.1 |
| 12c | 0 | >0.1 | >0 | >0.1 |
| 13a | 0 | >0.1 | >0.1 | 0 |
| 13b | 0 | 0 | >0.1 | >0.1 |
| 13c | 0 | >0.1 | >0.1 | >0.1 |
| 14a | 0 | >0.1 | >0.2 | 0 |
| 14b | 0 | 0 | >0.2 | >0.1 |
| 14c | 0 | >0.1 | >0.2 | >0.1 |
| 15a | 0 | >0.1 | >0.3 | 0 |
| 15b | 0 | 0 | >0.3 | >0.1 |
| 15c | 0 | >0.1 | >0.3 | >0.1 |
| 16a | 0 | >0.1 | >0.4 | 0 |
| 16b | 0 | 0 | >0.4 | >0.1 |
| 16c | 0 | >0.1 | >0.4 | >0.1 |
| 17a | 0 | >0.1 | >0.5 | 0 |
| 17b | 0 | >0 | >0.5 | >0.1 |
| 17c | 0 | >0.1 | >0.5 | >0.1 |
| 18a | 0 | >0.1 | >0.6 | 0 |
| 18b | 0 | 0 | >0.6 | >0.1 |
| 18c | 0 | >0.1 | >0.6 | >0.1 |
| 19a | 0 | >0.1 | >0.7 | 0 |
| 19b | 0 | >0.1 | >0.7 | >0.1 |
| 19c | 0 | 0 | >0.7 | >0.1 |
| 20a | 0 | >0.1 | >0.8 | 0 |
| 20b | 0 | 0 | >0.8 | >0.1 |
| 20c | 0 | >0.1 | >0.8 | >0.1 |
| 21a | 0 | >0.1 | >0.9 | 0 |
| 21b | 0 | 0 | >0.9 | >0.1 |
| 21c | 0 | >0.1 | >0.9 | >0.1 |
| 22a | >0 | >0.1 | >0.7 | 0 |
| 22b | >0 | 0 | >0.7 | >0.1 |
| 22c | >0 | >0.1 | >0.7 | >0.1 |
| 23a | >0.1 | >0.1 | >0.6 | 0 |
| 23b | >0.1 | 0 | >0.6 | >0.1 |
| 23c | >0.1 | >0.1 | >0.6 | >0.1 |
| 24a | >0.2 | >0.1 | >0.5 | 0 |
| 24b | >0.2 | 0 | >0.5 | >0.1 |
| 24c | >0.2 | >0.1 | >0.5 | >0.1 |
| 25a | >0.3 | >0.1 | >0.4 | 0 |
| 25b | >0.3 | 0 | >0.4 | >0.1 |
| 25c | >0.3 | >0.1 | >0.4 | >0.1 |
| 26a | >0.4 | >0.1 | >0.3 | 0 |
| 26b | >0.4 | 0 | >0.3 | >0.1 |
| 26c | >0.4 | >0.1 | >0.3 | >0.1 |
| 27a | >0.5 | >0.1 | >0.2 | 0 |
| 27b | >0.5 | >0 | >0.2 | >0.1 |
| 27c | >0.5 | >0.1 | >0.2 | >0.1 |
| 28a | >0.6 | >0.1 | >0.1 | 0 |
| 28b | >0.6 | 0 | >0.1 | >0.1 |
| 28c | >0.6 | >0.1 | >0.1 | >0.1 |
| 29a | >0.7 | >0.1 | >0 | 0 |
| 29b | >0.7 | >0.1 | >0 | >0.1 |
| 29c | >0.7 | 0 | >0 | >0.1 |

In one embodiment, the non-fouling polymeric material is a polyampholyte zwitterionic polymer or copolymer comprising repeat units corresponding to repeat unit D of Formula 4. That is, d is greater than 0 and a fraction of the repeat units corresponding to repeat unit D are anionic repeat units ($X^4$ for such units is an anionic pendant group) and a fraction of the repeat units corresponding of Formula 4 are cationic repeat units ($X^4$ for such units is a cationic pendant group). For example, in one such embodiment, d is at least 0.1 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.2 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.3 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.4 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.5 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.6 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.7 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.8 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.9 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in each of said examples in this paragraph, the remaining repeat units may correspond to repeat unit A. By way of further example, in each of said examples in this paragraph, the remaining repeat units may correspond to repeat unit B. By way of further example, in each of said examples in this paragraph, the remaining repeat units may correspond to repeat unit C.

More preferably, the non-fouling polymeric material is a zwitterionic polymer or copolymer comprising repeat units corresponding to repeat unit A and/or repeat unit C of Formula 4.

In certain embodiments, the non-fouling polymeric material is a homopolymer or copolymer comprising repeat units corresponding to Formula 5, Formula 6, Formula 7, Formula 8, or Formula 9:

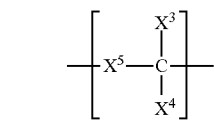
Formula 5

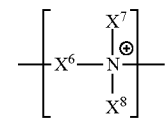
Formula 6

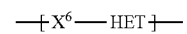
Formula 7

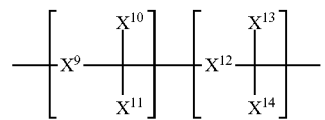
Formula 8

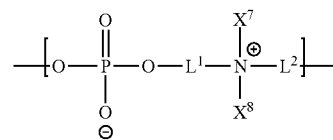
Formula 9

HET is part of a heterocyclic structure,
$X^3$ is hydrogen, alkyl or substituted alkyl,
$X^4$ is $-OX^{40}$, $-NX^{41}X^{42}$, $-SX^{40}$, aryl, heteroaryl or acyl,
$X^5$ is ester, anhydride, imide, amide, ether, thioether, thioester, hydrocarbylene, substituted hydrocarbylene, heterocyclo, urethane, or urea;
$X^6$ is hydrocarbylene, substituted hydrocarbylene, heterocyclo, amide, anhydride, ester, imide, thioester, thioether, urethane, or urea;
$X^7$ is hydrogen, alkyl or substituted alkyl;
$X^8$ is an anionic moiety;
$X^9$ is hydrocarbylene, substituted hydrocarbylene, heterocyclo, amide, anhydride, ester, imide, thioester, thioether, urethane, or urea;
$X^{10}$ is hydrogen, alkyl or substituted alkyl;
$X^{11}$ is a cationic moiety;
$X^{12}$ is hydrocarbylene, substituted hydrocarbylene, heterocyclo, amide, anhydride, ester, imide, thioester, thioether, urethane, or urea;
$X^{13}$ is hydrogen, alkyl or substituted alkyl;
$X^{14}$ is an anionic moiety;
$L^1$ and $L^2$ are independently hydrocarbylene, substituted hydrocarbylene, heterocyclo, amide, anhydride, ester, imide, thioester, thioether, urethane, or urea; and
$X^{40}$ is hydrogen, hydrocarbyl, substituted hydrocarbyl, heterocyclo or acyl, and
$X^{41}$ and $X^{42}$ are independently hydrogen, hydrocarbyl, substituted hydrocarbyl or heterocyclo.

In one embodiment, the non-fouling polymeric material comprises repeat units corresponding to Formula 7 wherein the heterocycle, HET corresponds to Formulae 10, 11 or 12:

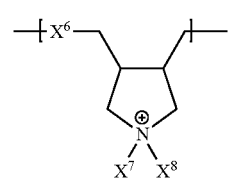
Formula 10

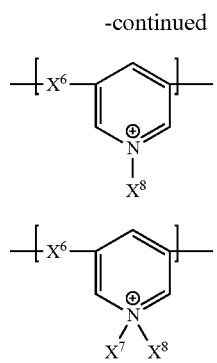

Formula 11

Formula 12 wherein $X^6$ is hydrocarbylene, substituted hydrocarbylene, heterocyclo, amide, anhydride, ester, imide, thioester, thioether, urethane, or urea; $X^7$ is hydrogen, alkyl or substituted alkyl; and $X^8$ is an anionic moiety.

Suitable comonomers include, but are not limited to, acrylates, acrylamides, vinyl compounds, multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams, and combination thereof. In the interests of brevity, exemplary methacrylate monomers are listed below (but it should be understood that analogous acrylate, acrylamide and methacrylamide monomers may be similarly listed and are similarly included):

Charged methacrylates or methacrylates with primary, secondary or tertiary amine groups, such as, 3-sulfopropyl methacrylate potassium salt, (2-dimethylamino) ethyl methacrylate) methyl chloride quaternary salt, [2-(methacryloyloxy)ethyl]trimethyl-ammonium chloride, methacryloyl chloride, [3-(methacryloylamino)propyl]-trimethylammonium chloride), 2-aminoethyl methacrylate hydrochloride, 2-(diethylamino)ethyl methacrylate, 2-(dimethylamino)ethyl methacrylate, 2-(tert-butylamino)ethyl methacrylate, and 2-(tert-butylamino-ethyl methacrylate.

Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10,10-heptadecafluorodecyl methacrylate.

Reactive or crosslinkable methacrylates, such as 2-(trimethylsilyloxy)ethyl methacrylate, 3-(trichlorosilyl)propyl methacrylate, 3-(trimethoxysilyl)propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate 3-(dimethylchlorosilyl)propyl methacrylate 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

Multifunctional monomers, such as di, tri, or tetraacrylates and di, tri, or tetraacrylamides can be used to form highly branched structures which can provide a higher concentration of non-fouling groups on the surface. As previously noted, the non-fouling polymeric material may contain a non-zwitterionic non-fouling material, alone or in combination with a zwitterionic material. These non-fouling groups may have varying degrees of non-fouling performance in a range of environments. Suitable non-zwitterionic materials include, but are not limited to, polyethers, such as polyethylene glycol, poly(ethylene oxide-co-propylene oxide) (PEO-PPO) block copolymers, polysaccharides such as dextran, hydrophilic polymers such as polyvinylpyrrolidone (PVP) and hydroxyethyl-methacrylate (HEMA), acrylonitrile-acrylamide copolymers, heparin, heparin fragments, derivatized heparin fragments, hyaluronic acid, mixed charge materials, and materials containing hydrogen bond accepting groups, such as those described in U.S. Pat. No. 7,276,286. Suitable polymer structures included, but are not limited to, polymers or copolymers containing monomers of Formula I wherein ZI is replaced by a non-zwitterionic, non-fouling headgroup.

In one embodiment, the non-fouling material is a polymer containing repeat units derived from sulfobetaine-containing and/or carboxybetaine-containing monomers. Examples of monomers include sulfobetaine methacrylate (SBMA), sulfobetaine acrylamide, sulfobetaine methacrylamide, carboxybetaine methacrylate (CBMA), carboxybetaine acrylamide and carboxybetaine methacrylamide. Examples of such polymers include, but are not limited to, poly(carboxy betaine methacrylate) (polyCBMA), poly(carboxybetaine acrylamide), poly(carboxybetaine methacrylamide) poly(sulfobetaine methacrylate) (polySBMA), poly(sulfobetaine acrylamide), and poly(sulfobetaine methacrylamide). In another embodiment, the non-fouling material polymer is a polymer containing the residue of CBMA or SBMA and one or more additional monomers. The additional monomers can be zwitterionic or non-zwitterionic monomers.

In one preferred embodiment, the grafted polymer comprises a grafted polymer corresponding to Formula 1, comprises zwitterionic pendant groups and the surface modification has a thickness which is at least equal to the surface roughness of the substrate surface. In one such preferred embodiment, the grafted polymer corresponds to Formula 3 and comprises sulfo ammonium or carboxy ammonium pendant groups. In one such preferred embodiment, the grafted polymer comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the combined average dry thickness of the polymeric primer and the grafted polymer is at least 110% of the global average $R_{rms}$ surface roughness of the substrate surface. In one such preferred embodiment, the grafted polymer is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the combined average dry thickness of the polymeric primer and the grafted polymer is at least 200% of the global average $R_{rms}$ surface roughness of the substrate surface. In one such preferred embodiment, the grafted polymer is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the combined average dry thickness of the polymeric primer and the grafted polymer is at least 200% of the global average $R_{rms}$ surface roughness of the substrate surface. In one such preferred embodiment, the grafted polymer is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the combined average dry thickness of the polymeric primer and the grafted polymer is at least 200% of the global average $R_{rms}$ surface roughness of the substrate surface. In one such preferred embodiment, the grafted polymer is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the combined average dry thickness of the polymeric primer and the grafted polymer is at least 200% of the global average $R_{rms}$ surface roughness of the substrate surface. In one such preferred embodiment, the grafted polymer is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the combined average dry thickness of the polymeric primer and the grafted polymer at least 200% of the global average $R_{rms}$ surface roughness of the substrate surface. In one such preferred embodiment, grafted polymer is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the combined average dry thickness of the polymeric primer and the grafted polymer is at least 200% of the global average $R_{rms}$ surface roughness of the substrate surface.

In another preferred embodiment, the grafted polymer comprises a grafted polymer corresponding to Formula 1, comprises zwitterionic pendant groups and the grafted polymer has an average dry thickness of at least 50 nm. In one such preferred embodiment, the grafted polymer corresponds to Formula 3 and comprises sulfobetaine or carboxybetaine pendant groups. In one such preferred embodiment, the grafted polymer comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, the grafted polymer is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and has an average dry thickness of at least about 50 nm, as measured by SEM under vacuum. In one such preferred embodiment, the grafted polymer is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an average dry thickness of at least about 50 nm, as measured by SEM under vacuum. In one such preferred embodiment, the grafted polymer is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an average dry thickness of at least about 50 nm, as measured by SEM under vacuum. In one such preferred embodiment, the grafted polymer is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an average dry thickness of at least about 50 nm, as measured by SEM under vacuum. In one such preferred embodiment, the grafted polymer is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an average dry thickness of at least about 50 nm, as measured by SEM under vacuum. In one such preferred embodiment, the grafted polymer is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an average dry thickness of at least about 50 nm, as measured by SEM under vacuum. By way of further example, in each of the foregoing embodiments, the average dry thickness may be even greater, e.g., at least about 200 nm, at least about 300 nm, at least about 400 nm, or at least about 500 nm.

In another preferred embodiment, the grafted polymer comprises a grafted polymer corresponding to Formula 1 and comprises zwitterionic pendant groups and the surface modification, i.e., the grafted polymer, has a relatively uniform thickness. In one such preferred embodiment, the grafted polymer corresponds to Formula 3 and comprises sulfobetaine or carboxybetaine pendant groups. In one such preferred embodiment, the grafted polymer comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, the grafted polymer is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the average variation of the average dry thickness of the non-fouling grafted polymer does not exceed 100% of the average dry thickness of the non-fouling grafted polymer. In one such preferred embodiment, the grafted polymer is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the average variation of the average dry thickness of the non-fouling grafted polymer does not exceed 100% of the average dry thickness of the non-fouling grafted polymer. In one such preferred embodiment, the grafted polymer is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the average variation of the average dry thickness of the non-fouling grafted polymer does not exceed 100% of the average dry thickness of the non-fouling grafted polymer. In one such preferred embodiment, the grafted polymer is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the average variation of the average dry thickness of the non-fouling grafted polymer does not exceed 100% of the average dry thickness of the non-fouling grafted polymer. In one such preferred embodiment, the grafted polymer is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the average variation of the average dry thickness of the non-fouling grafted polymer does not exceed 100% of the average dry thickness of the non-fouling grafted polymer. In one such preferred embodiment, the grafted polymer is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the average dry thickness of the non-fouling grafted polymer does not exceed 100% of the average dry thickness of the non-fouling grafted polymer. By way of further example, in each of the foregoing embodiments, the standard deviation of thickness may be even less, e.g., less than 50% of the average dry thickness of the non-fouling grafted polymer, less than 20% of the average dry thickness of the non-fouling grafted polymer, or less than 10% of the average dry thickness of the non-fouling grafted polymer.

In another preferred embodiment, the grafted polymer corresponds to Formula 1, comprises zwitterionic pendant groups and the surface modified article exhibits a static contact angle of less than 40 degrees. In one such preferred embodiment, the grafted polymer corresponds to Formula 3 and comprises sulfobetaine or carboxybetaine pendant groups. In one such preferred embodiment, the grafted polymer comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, the grafted polymer is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the surface modified article exhibits a static contact angle of less than 25 degrees. In one such preferred embodiment, the grafted polymer is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the surface modified article exhibits a static contact angle of less than 25 degrees. In one such preferred embodiment, the grafted polymer is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the surface modified article exhibits a static contact angle of less than 25 degrees. In one such preferred embodiment, the grafted polymer is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the surface modified article exhibits a static contact angle of less than 25 degrees. In one such preferred embodiment, the grafted polymer is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the surface modified article exhibits a static contact angle of less than 25 degrees. In one such preferred embodiment, the grafted polymer is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the surface modified article exhibits a static contact angle of less than 25 degrees. By way of further example, in each of the foregoing embodiments, the surface modified article exhibits a static contact angle may be even less, e.g., less than 24, less than 23, less than 22, less than 21, less than 20, less than 19, less than 18, less than 17, less than 16, or less than 15.

In another preferred embodiment, the grafted polymer corresponds to Formula 1, comprises zwitterionic pendant groups and the grafted polymer, i.e., the surface modification, has a volumetric swelling capacity, as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. In one such preferred embodiment, the grafted polymer corresponds to Formula 3 and comprises sulfobetaine or carboxybetaine pendant groups. In one such preferred embodiment, the grafted polymer comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the grafted polymer has a volumetric swelling capacity as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. In one such preferred embodiment, the grafted polymer is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer has a volumetric swelling capacity as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. In one such preferred embodiment, the grafted polymer is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer has a volumetric swelling capacity as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. In one such preferred embodiment, the grafted polymer is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer has a volumetric swelling capacity as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. In one such preferred embodiment, the grafted polymer is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer has a volumetric swelling capacity as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. In one such preferred embodiment, the grafted polymer is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer has a volumetric swelling capacity as measured by the magnitude of the difference between the global average dry thickness of the grafted polymer as determined by standard scanning electron microscopy (SEM) and the global average humidified thickness of the grafted polymer as determined by environmental scanning electron microscopy (ESEM), that is less than 200% of the global average dry thickness. By way of further example, in each of the foregoing embodiments, the grafted polymer has a volumetric swelling capacity that may be less than 200%, e.g., less than 100%, less than 50%, less than 25%, less than 10%, less than 5%, less than 1%, or even 0, as measured by the magnitude of the difference between the global average dry thickness of the grafted polymer as determined by standard scanning electron microscopy (SEM) and the global average humidified thickness of the grafted polymer as determined by environmental scanning electron microscopy (ESEM).

In another preferred embodiment, the grafted polymer corresponds to Formula 1, comprises zwitterionic pendant groups and the surface-modified article exhibits a relatively low affinity for proteins. For example, it is generally preferred that the non-fouling surface exhibit a fibrinogen adsorption of less than 30 ng/cm$^2$ in a fibrinogen adsorption assay. In one such preferred embodiment, the grafted polymer corresponds to Formula 3 and comprises sulfobetaine or carboxybetaine pendant groups. In one such preferred embodiment, the grafted polymer comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the non-fouling surface exhibits a fibrinogen adsorption of less than 10 ng/cm$^2$. In one such preferred embodiment, the grafted polymer is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the non-fouling surface exhibits a fibrinogen adsorption of less than 10 ng/cm$^2$. In one such preferred embodiment, the grafted polymer is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the non-fouling surface exhibits a fibrinogen adsorption of less than 10 ng/cm$^2$. In one such preferred embodiment, the grafted polymer is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the non-fouling surface exhibits a fibrinogen adsorption of less than 10 ng/cm$^2$. In one such preferred embodiment, the grafted polymer is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the non-fouling surface exhibits a fibrinogen adsorption of less than 10 ng/cm$^2$. In one such preferred embodiment, the grafted polymer is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the non-fouling surface exhibits a fibrinogen adsorption of less than 10 ng/cm$^2$. By way of further example, in each of the foregoing embodiments, the non-fouling surface exhibits a fibrinogen adsorption that may be less than 10 ng/cm$^2$, e.g., less than 5 ng/cm$^2$, less than 1 ng/cm$^2$, or less than less than 0.3 ng/cm$^2$.

During both the chemistry and the catheter coating optimizations, primed substrates can be characterized for chemical, biological, and mechanical properties to ensure proper alignment with key product requirements. Suitable assays include:

Attenuated Total Reflection IR (ATR-IR) can be utilized to verify the chemical composition of the primer.

Scanning electron microscopy (SEM) can be utilized on the sample cross-section to determine thickness. Samples are typically flash frozen in liquid nitrogen and then freeze fractured to prevent any distortion of the coating during sectioning.

Mechanical stability of coatings can be demonstrated by examining both activity and potential cracking (via microscopy) after stretching and bending stresses of the catheter.

An enzyme-linked immunosorbent assay (ELISA) can be used to quantify fibrinogen binding.

Supernatants from samples stored in PBS can be inoculated with bacteria to confirm the lack of any leaching antimicrobial agents that could confound biological testing results A 24-hr biofilm system can be used to assess bacterial growth on coated and reference catheter segments using both *S. epidermidis* and *S. aureus*

A 2-hr external flow loop with fresh bovine blood can be used to quantify attachment of radio-labeled platelets as a measure of thrombosis formation Using the assays described above, coating formulations can be optimized to maximize anti-thrombotic, antimicrobial, and anti-adherent properties of catheter substrate materials. For example, for topcoats, the ratio of CBMA to AEMA monomers can be varied from 1:1 to 20:1 to provide maximum protein resistance while still ensuring stable immobilization to the undercoat. NMR analysis (both proton and carbon) can be used to determine the ratio of monomer units incorporated into the polymer. The effect of top coat average molecular weight can be evaluated using dialysis and precipitation of top coat formulations. Effects of molecular weight distribution can be examined using varying free radical initiation schemes including uncontrolled initiation (which typically provide a polydispersity>1.5) and highly controlled initiation through atom transferred radical polymerization (which typically provide a polydispersity<1.1). Gel permeation chromatography (GPC) with refractive index (RI) can be used to measure the molecular weight distribution of all coatings Fluorescent and Colorimetric Labels In one embodiment, the surface is stained or labeled with one or more colorimetric labels, fluorescence labels, or combinations thereof. These labels are used to visualize the surface using the naked eye, spectroscopy, microscopy, or combinations thereof. Suitable microscopy techniques include, but are not limited to, optical microscopy, fluorescent microscopy, and combinations thereof.

The surface can be stained through a chemical reaction or by physical adsorption such as charge-charge interactions, hydrophobic interactions, or hydrophilic interactions. Labeling compounds include, but are not limited to, compounds or derivatives of rhodamine, fluorescein, coumarin, orange B, crystal violets, toluidine blue, methyl violet, nuclear fast red, methylene blue, malachite green, magenta, acriflavine, and other azo compounds.

In another embodiment the grafted polymer, such as a zwitterionic polymer, is labeled by incorporating one or more reactive labeling monomers into the polymer backbone during polymerization. These labeling monomers include, but not limited to, FITC-methacrylate, FITC-acrylate, rhodamine-methacrylate, rhodamine-acrylate, their derivatives or any other fluorescent acrylate, methacrylate, acrylamide, vinyl compound, diol or diamine. Incorporation of these groups can allow for convenient measurement of conformality and/or grafted polymer thickness. This may be particularly useful as a quality control metric for conformality verification during manufacturing of the grafted polymer on an underlying device.

In another embodiment, the grafted polymer is stained with one or more compounds, which can be easily visualized under an electronic microscope (SEM or TEM). These compounds include, but are not limited to osmium tetroxide and ruthenium tetroxide.

Bioactive Agents

Therapeutics, diagnostic, and/or prophylactic agents can be immobilized on or otherwise incorporated into an article of the present invention. When optionally included, such bioactive agents may be leachable or non-leachable. For example, the bioactive agent may be dissolved or otherwise contained within the substrate, or covalently or non-covalently associated with the grafted polymer, and leached or otherwise disassociated with the article in a controlled or uncontrolled manner (e.g., by leaching). These agents can interact passively or actively with the surrounding in vivo environment. The agents can also be used to alter the surrounding in vivo chemistry or environment. Two or more agents can be immobilized to a substrate surface, wherein the activity of the two agents is greater than either of the agents alone. A substance, material or agent that is not considered active, can become active if an active agent is immobilized on the substance, material or agent. Active agents include, but are not limited to inorganic compounds, organometallic compounds, organic compounds or any synthetic or natural, chemical or biological compounds of known or unknown therapeutic effect.

In general, a bioactive agent can be immobilized covalently or non-covalently directly on the substrate, on the undercoating layer, on the non-fouling material, or combinations thereof. In one embodiment, the bioactive agent is immobilized covalently by reacting one or more functional groups on the active agent with one or more functional groups on the substrate, undercoating layer, and/or non-fouling material. Covalent bonds can be formed by a variety of reaction mechanisms including, but not limited to, substitution, addition, and condensation reactions.

Typically, the bioactive agent will typically be immobilized on the non-fouling material after the non-fouling material has been grown from the surface. In an alternative embodiment, the bioactive agent can be co-immobilized with the non-fouling material in a side by side structure. In the graft-from methods, a tether can be grown from the surface and the active agent immobilized on the tether. Alternatively, the active agent can be immobilized directly on the surface without the use of a tether.

Cell adhesion agents can be immobilized to the compositions described herein. The efficacy of a cell adhesion agent in binding cells in complex environments may be enhanced by reducing non-specific protein adsorption on the surface from which they are presented, given that cell attachment may be a competitive process with other protein adsorption. Further, there may an advantage to resisting attachment of any cells other than those specifically targeted by the cell adhesion agent to prevent competitive blocking of the surface.

Examples of desirable cell attachment agents include, but are not limited to, integrin binders. Exemplary integrin binders include, but are not limited to, RGD peptides, along with a number of variants that include RGD motifs, YIGSR peptides, fibronectin, laminin or other proteins or peptides. Longer variants of these peptide may have more specific target cell binding. Further, the ability to present locally dense concentrations of cell attachment agents may increase the effectiveness of cell attachment by creating multimeric interactions. Other cell adhesion agents include, but are not limited, to REDV peptides. Tailored integrin binders can be used for a variety of applications including osteointegration.

Cell adhesion agents that bind specific immune cells may also benefit from attachment to zwitterions. Adhesion of immune cells to the biomaterial surface activates these cells and prefaces their phenotypic response, such as the transition of monocytes to macrophages that can result, in some cases, in the fusion into undesirable foreign body giant cells. The inherent resistivity to random protein fouling that zwitterions possess provides a unique platform to couple biomolecules that act as specific ligands for immune cells including neutrophils, monocytes, helper T-cells, killer T-cells, suppressor T-cells, B-cells and dendritic cells. Selection of appropriate ligands may prime these cells for beneficial instead of detrimental functions. These ligands include peptides or proteins that specifically bind immune cell receptors such as integrins, selectins, complement, or Fc gamma. When bound to these cell-associated proteins, such ligands may stimulate intracellular signaling pathways that lead to responses including cytoskeletal rearrangements, production and secretion of molecules including chemokines, cytokines and other chemoattractants, and induction of apoptosis. Desirable behaviors that could be tailored by presentation of biomolecules via zwitterionic tethers may include prevention/reduction in the secretion of proinflammatory cytokines, enhancement of phagocytosis, and modulation of the release of soluble factors that influence tissue-device integration.

Osteointegration may also be promoted or induced by factors which would benefit from the non-fouling properties and stable presentation of non-fouling materials, such as zwitterions. Osteointegration promoting agents include, but are not limited to, bone-morphogenic proteins, such as BMP2 and shortened analogues thereof. Non-fouling surfaces, such as zwitterionic surfaces, may enhance the activity of agents designed to promote desired cell regrowth over a surface. Reducing attachment of neutrophils and macrophages may inhibit the foreign body response and enable desired cell attachment and growth process to be favored.

Presentation of antithrombotic agents may also be more effective when tethered to non-fouling materials, such as zwitterionic materials, relative to other tethers. The process of thrombosis involves both surface and bulk pathways. Zwitterions have shown an ability to reduce platelet attachment and activation, reducing one pathway. Combining an active antithrombotic that assists in the reduction of platelet activation or directly targets additional pathways for thrombosis with a zwitterionic tether could enhance the antithrombotic effect compared to either a non-platelet adherent surface or the antithrombotic agent alone. Suitable antithrombotic agents include, but are not limited to, thrombomodulin, heparin, heparin fragments, derivatized heparin fragments, hyaluronic acid, reversible albumin binders, tissue plasminogen activator binders, transglutimase, reversible NO binders, polylysine, sulphonated polymers, thrombin inhibitors including hirudin, urokinase, and streptokinase.

Device-centered infection remains a large problem. Non-fouling materials, such as zwitterions materials, can by themselves diminish microbial adhesion and retard biofilm development. Prevention of microbial adhesion and biofilm can be further enhanced on non-fouling surfaces, such as zwitterionic surfaces, by presentation of antimicrobials including, but not limited to, membrane-targeting antimicrobial agents, antimicrobial peptides and small molecule antimicrobial agents. Generally, antimicrobial peptides are cationic molecules with spatially separated hydrophobic and charged regions. Exemplary antimicrobial peptides include linear peptides that form an α-helical structure in membranes or peptides that form β-sheet structures, optionally stabilized with disulfide bridges in membranes. Representative antimicrobial peptides include, but are not limited to, cathelicidins, defensins, dermcidin, and more specifically magainin 2, protegrin, protegrin-1, melittin, II-37, dermaseptin 01, cecropin, caerin, ovispirin, cecropin A melittin hybrid, and alamethicin, or hybrids or analogues of other AmPs. Naturally occurring antimicrobial peptides include peptides from vertebrates and non-vertebrates, including plants, humans, fungi, microbes, and insects.

Antimicrobial peptides can be made from naturally occurring amino acids, non-naturally occurring amino acids (e.g., synthetic or semisynthetic amino acids and peptidomimetics), or combinations thereof. Antimicrobial peptides which retain their activity when immobilized on a surface are generally referred to as membrane-targeting antimicrobial agents. Antimicrobial peptides can be immobilized on the non-fouling grafted polymer, the substrate, the undercoating or combinations thereof by reacting a functional group on the peptide with a functional group on the non-fouling grafted polymer, the substrate, and/or the primer coat. For example, the peptide can be designed to have a cysteine residue which can be used to immobilize the peptide on a surface by reacting the thiol group of the cysteine residue with a thiol-reactive group on the surface.

Tethering of these agents via non-fouling materials, such as zwitterions, should provide stable, long-term activity. Additionally, immobilization of enzymes that degrade bacterial attachment and biofilm proteins, such as glycosylases, lyases, and serine-proteases, or those that degrade microbial communication signal molecules, such as N-acyl-homoserine lactone acylases, could provide improved efficacy in prevention of initial microbial adhesion events and subsequent biofilm formation.

A broad range of antimicrobial or antiseptic agents may be incorporated in the substrate or the non-fouling polymer to enhance antimicrobial activity at the surface or be released to provide antimicrobial activity in the environment surrounding the article. Suitable agents include silver metals, silver salts such as silver sulfadiazine, silver oxide, silver carbonate, silver acetate, silver alginate, silver azide, silver citrate, silver lactate, silver nitrate, silver sulfate, silver chloride, silver thiocyanate, silver-sodium-hydrogen-zirconium phosphate, silver sulfadiazine, silver cyclohexanediacetic acid and disilver 2,5-dichloro-3,6-dihydroxy-2,5-cyclohexadiene-1,4-dione, among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidoneiodine, parachlorometaxylene, gramicidin, polymixin, norfloxacin, tobramycin, sulfamylon, polyhexamethylene biguanide, alexidine, iodine, rifampicin, miconazole, bacitracin, and minocycline, ciprofloxacin, clindamycin, erythromycin, gentamycin, tetracycline and vancomycin.

Biguanide compounds which may be used according to the invention include poly (hexamethylene biguanide) hydrochloride and chlorhexidine compounds. Chlorhexidine is the term denoting the chemical compound 1,6 bis(N5-p-chlorophenyl-N1-biguanido)hexane). Chlorhexidine compounds include chlorhexidine free base ("CHX") as well as chlorhexidine salts, such as chlorhexidine diphosphanilate, chlorhexidine digluconate ("CHG"), chlorhexidine diacetate ("CHA"), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine mono-diglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxy-napthoate, and chlorhexidine embonate.

Bismuth salts which may be used according to the invention include bismuth nitrate, bismuth citrate, bismuth salicylate, bismuth borate, bismuth mandelate, bismuth palmitate, bismuth benzoate, and bismuth sulfadiazine.

Cerium salts which may be used according to the invention include cerium nitrate and other cerium salts having a water solubility similar to cerium nitrate.

The term silver-containing compound, as used herein, refers to a compound comprising silver, either in the form of a silver atom or a silver ion unlinked or linked to another molecule via a covalent or noncovalent (e.g., ionic) linkage, including but not limited to covalent compounds such as silver sulfadiazine ("AgSD") and silver salts such as silver oxide ("Ag$_2$O"), silver carbonate ("Ag$_2$CO$_3$"), silver deoxycholate, silver salicylate, silver iodide, silver nitrate ("AgNO$_3$"), silver paraaminobenzoate, silver paraaminosalicylate, silver acetylsalicylate, silver ethylenediaminetetraacetic acid ("Ag EDTA"), silver picrate, silver protein, silver citrate, silver lactate and silver laurate.

Zinc salts which may be used according to the invention include zinc acetate and other zinc salts having a water solubility similar to zinc acetate.

The classes of bioactive agents identified above may be incorporated in the substrate or the non-fouling polymer to enhance antimicrobial activity at the surface or be released to provide antimicrobial activity in the environment surrounding the article.

Additional groups/classes of bioactive agents may be incorporated in the substrate or the non-fouling polymer to enhance antimicrobial activity at the surface or be released to provide antimicrobial activity in the environment surrounding the article and include the following groups/classes:

Antipyretics, analgesics and antiphlogistics (such as indometacin, acetylsalicylic acid, diclofenac sodium, ketoprofen, ibuprofen, mefenamic acid, azulene, phenacetin, isopropyl antipyrine, acetaminophen, benzadac, phenylbutazone, flufenamic acid, acetylsalicylic acid (aspirin), paracetamol, phenazone, sodium salicylate, salicylamide, sazapyrine, and etodolac) Opioid analgesics (such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine) Non-selective COX inhibitors such as salicylic acid derivatives, aspirin, sodium salicylate, choline magnesium trisalicylate, salsalate, diflunisal, sulfasalazine and olsalazine). Para-aminophenol derivatives such as acetaminophen. Indole and indene acetic acids such as indomethacin and sulindac. Heteroaryl acetic acids such as tolmetin, dicofenac and ketorolac. Arylpropionic acids such as ibuprofen, naproxen, flurbiprofen, ketoprofen, fenoprofen and oxaprozin. Anthranilic acids (fenamates) such as mefenamic acid and meloxicam. Enolic acids such as the oxicams (piroxicam, meloxicam). Alkanones such as nabumetone. Selective COX-2 Inhibitors (such as diaryl-substituted furanones such as rofecoxib; diaryl-substituted pyrazoles such as celecoxib; indole acetic acids such as etodolac and sulfonanilides such as nimesulide)

Anti-inflammatory steroids (such as cortisone, hydrocortisone, prednisone, dexamethasone, methylprednisolone, triamcinolone beclomethasone flunisolide, fluticasone proprionate triamcinolone acetonide budesonide loterednol etabonate and mometasone, aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone and their derivatives and)

Antiulcer drugs (such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride)

Coronary vasodilators (such as nifedipine, isosorbide dinitrate, diltiazem hydrochloride, trapidil, dipyridamole, dilazep hydrochloride, verapamil, nicardipine, nicardipine hydrochloride and verapamil hydrochloride)

Peripheral vasodilators (such as ifenprodil tartrate, cinepacide maleate, ciclandelate, cynnaridine and pentoxyphylin)

Antibiotics (such as ampicillin, amoxicillin, cefalexin, cephalexin, cefoxytin and cephalothin, erythromycin-ethyl succinate, vacampicillin hydrochloride, minocycline hydrochloride, chloramphenicol, tetracycline, erythromycin, ceftazidime, cefuroxime sodium, aspoxicillin chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide)

Synthetic antimicrobials (such as nalidixic acid, piromidic acid, pipemidic acid trihydrate, enoxacin, cinoxacin, of loxacin, norfloxacin, ciprofloxacin hydrochloride and sulfamethoxazole-trimethoprim)

Antiviral agents (such as acyclovir, ganciclovir, acyclovir prodrugs, famcyclovir, zidovudine, didanosine, stavudine, lamivudine, zalcitabine, saquinavir, indinavir, ritonavir, n-docosanol, tromantadine and idoxuridine)

Anticonvulsants (such as propantheline bromide, atropine sulfate, oxitropium bromide, timepidium bromide, scopolamine butylbromide, trospium chloride, butropiumbromide, N-methylscopolaminemethylsulfate and methyloctatropine bromide)

Antitussives (such as tipepedine hibenzate, methylephedrine hydrochloride, codeine phosphate, tranilast, dextromethorphan hydrobromide, dimemorfan phosphate, clobutinol hydrochloride, fominoben hydrochloride, clebenproperine phosphate, eprazinone hydrochloride, clofedanol hydrochloride, ephedrine hydrochloride, noscapine, pentoxyverine citrate, oxeladin citrate and isoaminyl citrate)

Expectorants (such as bromhexine hydrochloride, carbocysteine, ethyl cysteine hydrochloride and methylcysteine hydrochloride)

Bronchodilators (such as theophylline, aminophylline, sodium cromoglicate, procaterol hydrochloride, trimetoquinol hydrochloride, diprophilline, salbutamol sulfate, clorprenaline hydrochloride, formoterol fumarate, ocriprenaline sulfate, pilbuterol hydrochloride, hexoprenaline sulfate, bitolterol mesilate, clenbuterol hydrochloride, terbutaline sulfate, malbuterol hydrochloride, fenoterol hydrobromide and methoxyphenamine hydrochloride), (13) cardiotonics (such as dopamine hydrochloride, dobutamine hydrochloride, docarpamine, denopamine, caffeine, digoxin, digitoxin and ubidecarenone)

Diuretics (such as furosemide, acetazolamide, triclormethiazide, methylclothiazide, hydrochlorothiazide, hydroflumethiazide, ethiazide, cyclopenthiazide, spironolactone, triamterene, florothiazide, piretanide, mefruside, etacrynic acid, azosemide and clofenamide)

Muscle relaxants (such as chlorphenesin carbamate, tolperisone hydrochloride, eperisone hydrochloride, tizanidine hydrochloride, mefenicine, chlorzoxazone, phenprobamate, methocarbamol, chlormezazone, pridinol mesilate, afloqualone, baclofen and dantrolene sodium)

Cerebral metabolism ameliorants (such as nicergoline, meclofenoxate hydrochloride and taltirelin), Minor tranquilizers (such as oxazolam, diazepam, clotiazepam, medazepam, temazepam, fludiazepam, meprobamate, nitrazepam and chlordiazepoxide)

Major tranquilizers (such as sulpiride, clocapramine hydrochloride, zotepine, chlorpromazine and haloperidol)

Beta-blockers (such as bisoprolol fumarate, pindolol, propranolol hydrochloride, carteolol hydrochloride, metoprolol tartrate, labetanol hydrochloride, acebutolol hydrochloride, bufetolol hydrochloride, alprenolol hydrochloride, arotinolol hydrochloride, oxprenolol hydrochloride, nadolol, bucumorol hydrochloride, indenolol hydrochloride, timolol maleate, befunolol hydrochloride and bupranolol hydrochloride)

Antiarrthymics (such as procainamide hydrochloride, diso-pyramide, ajmaline, quinidine sulfate, aprindine hydrochloride, propafenone hydrochloride, mexiletine hydrochloride and azmilide hydrochloride)

Athrifuges (such as allopurinol, probenicid, colchicine, sulfinpyrazone, benzbromarone and bucolome)

Anticoagulants/Antiplatelets (such as heparin, chondroiten sulfate ticlopidine hydrochloride, dicumarol, potassium warfarin, and (2R,3R)-3-acetoxy-5-[2-(dimethylamino)ethyl]-2,3-dihydro-8-methyl-2-(4-me-thylphenyl)-1,5-benzothiazepin-4(5H)-onemaleate)

Thrombolytics (such as stretokinase, urokinase and tissue plasminogin activators, methyl (2E,3Z)-3-benzylidene-4-(3,5-dimethoxy-α-methylbenzyliden-e)-N-(4-methylpiperazin-1-yl)-succinamate hydrochloride), Liver disease drugs (such as (.+-.)r-5-hydroxymethyl-t-7-(3,4-dimethoxyphenyl)-4-oxo-4,5,6,7-tetrahydrobenzo[b]furan-c-6-carboxylactone)

Antiepileptics (such as phenytoin, sodium valproate, metalbital and carbamazepine)

Antihistamines (such as chlorpheniramine maleate, clemastine fumarate, mequitazine, alimemazine tartrate, cyproheptadine hydrochloride and bepotastin besilate)

Antiemitics (such as difenidol hydrochloride, metoclopramide, domperidone and betahistine mesilate and trimebutine maleate), Depressors (such as dimethylaminoethyl reserpilinate dihydrochloride, rescinnamine, methyldopa, prazocin hydrochloride, bunazosin hydrochloride, clonidine hydrochloride, budralazine, urapidil and N-[6-[2-[(5-bromo-2-pyrimidinyl)oxy]ethoxy]-5-(4-methylphenyl)-4-pyri-midinyl]-4-(2-hydroxy-1,1-dimethyl-ethyl) benzenesulfonamide sodium)

Hyperlipidemia agents (such as pravastatin sodium and fluvastatin sodium)

Sympathetic nervous stimulants (such as dihydroergotamine mesilate and isoproterenol hydrochloride, etilefrine hydrochloride)

Oral diabetes therapeutic drugs (such as glibenclamide, tolbutamide and glimidine sodium)

Oral carcinostatics (such as malimastat)

Alkaloid narcotics (such as morphine, codeine and cocaine)

Vitamins (such as vitamin B1, vitamin B2, vitamin B6, vitamin B12, vitamin C and folic acid)

Thamuria therapeutic drugs (such as flavoxate hydrochloride, oxybutynin hydrochloride and terolidine hydrochloride)

Angiotensin converting enzyme inhibitors (such as imidapril hydrochloride, enalapril maleate, alacepril and delapril hydrochloride).

Non-steroidal anti-inflammatory agents [including their racemic mixtures or individual enantiomers where applicable] (such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate)

Antineoplastic/antiangiogenic (Such as acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof)

Immunosuppressant agents (such as cyclosporine A, mycophenolic acid, tacrolimus, rapamycin, rapamycin analogues, azathioprine, recombinant or monoclonal antibodies to interleukins, T-cells, B-cells and/or their receptors.

Vasodilators (such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol)

Antiproliferative agents (such as paclitaxel, actinomycin D, rapamycin, tacrolimus, everolimus, dexamethasone and rapamycin analogues)

Local anaesthetics (such as benzocaine, bupivacaine, amethocaine, lignocaine, lidocaine, cocaine, cinchocaine, dibucaine, mepivacaine, prilocalne, etidocaine, veratridine (specific c-fiber blocker) and procaine)

Antifungals (such as amorolfine, isoconazole, clotrimazole, econazole, miconazole, nystatin, terbinafine, bifonazole, amphotericin, griseo fulvin, ketoconazole, fluconazole and flucytosine, salicylic acid, fezatione, ticlatone, tolnaftate, triacetin, zinc, pyrithione and sodium pyrithione)

Agents/chemicals that block microbial attachment to target cells and/or inhibits entry of infectious pathogens (e.g. sulphated and sulponated polymers such as PC-515 (carrageenan), Pro-2000, and Dextrin 2 Sulphate)

Antiretroviral agents (e.g., PMPA gel) that prevent retroviruses from replicating in the cells Agents which change the condition of the tissue to make it hostile to the pathogen (such as substances which alter mucosal pH (e.g., Buffer Gel and Acidform);

Agents that treat or prevent an allergic or immune response and/or cellular proliferation (such as various cytokine inhibitors such as humanized anti-cytokine antibodies, anti-cytokine receptor antibodies, recombinant antagonists, or soluble receptors; various leucotriene modifiers such as zafirlukast, montelukast and zileuton; immunoglobulin E (IgE) inhibitors such as Omalizumab (an anti-IgE monoclonal antibody) and secretory leukocyte protease inhibitor) and SYK Kinase inhibitors)

Agents that prevent restenosis (such as paclitaxel, sirolimus, everolimus, vincristine, biolimus, mycophenolic acid, ABT-578, cervistatin, simvastatin, methylprednisolone, dexamethasone, actinomycin-D, angiopeptin, L-arginine, estradiol, 17-β-estradiol, tranilast, methotrexate, batimistat, halofuginone, BCP-671, QP-2, lantrunculin D, cytochalasin A, nitric oxide, and analogues and derivatives)

Growth factors and inflammatory cytokines involved in angiogenesis, fibroblast migration, fibroblast proliferation, ECM synthesis and tissue remodeling, such as epidermal growth factor (EGF) family, transforming growth factor-α (TGF-α), transforming growth factor-β (TGF-9-1, TGF-9-2, TGF-9-3, platelet-derived growth factor (PDGF), fibroblast growth factor (acidic—aFGF; and basic—bFGF), fibroblast stimulating factor-1, activins, vascular endothelial growth factor (including VEGF-2, VEGF-3, VEGF-A, VEGF-B, VEGF-C, placental growth factor—PIGF), angiopoietins, insulin-like growth factors (IGF), hepatocyte growth factor (HGF), connective tissue growth factor (CTGF), myeloid colony-stimulating factors (CSFs), monocyte chemotactic protein, granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, and IL-6), tumor necrosis factor-α (TNF9), nerve growth factor (NGF), interferon-α, interferon-β, histamine, endothelin-1, angiotensin II, growth hormone (GH), and synthetic peptides, analogues or derivatives of these factors are also suitable for release from specific implants and devices to be described later. Other examples include CTGF (connective tissue growth factor); inflammatory microcrystals (e.g., crystalline minerals such as crystalline silicates); bromocriptine, methylsergide, methotrexate, chitosan, N-carboxybutyl chitosan, carbon tetrachloride, thioacetamide, fibrosin, ethanol, bleomycin, naturally occurring or synthetic peptides containing the Arg-Gly-Asp (RGD) sequence, generally at one or both termini (see e.g., U.S. Pat. No. 5,997,895), and tissue adhesives, such as cyanoacrylate and crosslinked poly (ethylene glycol)-methylated collagen compositions, such as described below. Other examples of fibrosis-inducing agents include bone morphogenic proteins (e.g., BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Of these, BMP-2, BMP-3, BMP-4, BMP-5, BMP-6, and BMP-7 are of particular utility. Bone morphogenic proteins are described, for example, in U.S. Pat. Nos. 4,877,864; 5,013,649; 5,661,007; 5,688,678; 6,177,406; 6,432,919; and 6,534,268 and Wozney, J. M., et al. (1988) Science: 242(4885); 1528 1534.

Other representative fibrosis-inducing agents include components of extracellular matrix (e.g., fibronectin, fibrin, fibrinogen, collagen (e.g., bovine collagen), fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin, bitronectin), proteins found in basement membranes, and fibrosin) and inhibitors of matrix metalloproteinases, such as TIMPs (tissue inhibitors of matrix metalloproteinases) and synthetic TIMPs, e.g., marimistat, batimistat, doxycycline, tetracycline, minocycline, TROCADE, Ro-1130830, CGS 27023A, and BMS-275291.

Anti-thrombotic and/or antiplatelet agents (include heparin, heparin fragments, organic salts of heparin, heparin complexes (e.g., benzalkonium heparinate, tridodecylammonium heparinate, heparin-tridodecylmethylammonium chloride, heparin-benzalkonium chloride, heparin-steralkonium chloride, heparin-poly-N-vinylpyrrolidone, heparin-lecithin, heparin-didodecyldimethylammonium bromide, heparin-pyridinium chloride, and heparin-synthetic glycolipid complex), dextran, sulfonated carbohydrates such as dextran sulphate, coumadin, coumarin, heparinoid, danaparoid, argatroban chitosan sulfate, chondroitin sulfate, danaparoid, lepirudin, hirudin, AMP, adenosine, 2-chloroadenosine, aspirin, phenylbutazone, indomethacin, meclofenamate, hydrochloroquine, dipyridamole, iloprost, streptokinase, and factor Xa inhibitors, such as DX9065a, magnesium, and tissue plasminogen activator. In one aspect, the anti-thrombotic agent is a modified heparin compound, such as a hydrophobically modified heparin or modified hirudin compound (e.g., stearylkonium heparin, benzalkonium heparin, cetylkonium heparin, or trdodecylmethyl ammonium heparin). Further examples of anti-thrombotic agents include plasminogen, lys-plasminogen, alpha-2-antiplasmin, urokinase, ticlopidine, clopidogrel, glycoprotein IIb/IIIa inhibitors such as abcixamab, eptifibatide, and tirogiban. Other agents capable of affecting the rate of clotting include glycosaminoglycans, danaparoid, 4-hydroxycourmarin, warfarin sodium, dicumarol, phenprocoumon, indan-1,3-dione, acenocoumarol, anisindione, and rodenticides including bromadiolone, brodifacoum, diphenadione, chlorophacinone, and pidnone)

Polypeptide drugs (such as but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; and peptide or polypeptide vaccines. Cell response modifiers. (Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers (Such as the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin) Therapeutic enzymes (Such as proteases, phospholipases, lipases, glycosidases, cholesterol esterases, and nucleases) Peptide-nucleic acid (PNA) conjugate, polysaccharide-peptide conjugates such as glyosylated polypeptides; glycoproteins), a poly(ethyleneglycol)-polypeptide conjugate (PEG-ylated polypeptides), or polymer pharmaceuticals.

Antibodies and antibody fragments (Such as, but are not limited to, therapeutic antibodies include trastuzumab, alemtuzumab, gemtuzumab, rituximab, ibritumomab, tositumomab, edrecolomab, cetuximab, bevacizumab, Ranibizumab, satumomab, pertuzumab, and daclizumab)

Therapeutic enzymes (Such as recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase)

Enzyme inhibitors (Such as edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol)

Steroids (Such as glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fluorocortisone, fluorocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, fluorogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof)

Non-steroidal anti-inflammatory agents [including their racemic mixtures or individual enantiomers where applicable] (Such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate).

Formulations of the above bioactive agents may be enhanced by altering the solubility or physical characteristics of the agent if salts or crystals are used, for instance by using nanoparticles or other formulations with reduced size or enhanced surface area per mass.

Non-fouling surfaces, such as zwitterionic surfaces, may also present a particularly attractive surface for immobilization of biomolecules, such as antibodies, for use as biosensors. Immobilized antibodies on non-fouling surface surfaces, such as zwitterionic surfaces, have been demonstrated to retain both antibody activity and antigen specificity in whole blood. "Smart" implanted medical devices that detect undesirable activation of specific immune pathways, such as proinflammatory cytokines, or the presence of a possible infectious agent, perhaps through detection of a secreted microbial toxin, could be designed, for example, by utilizing specific antibodies or biomolecules tailored to monitor these threats. Appropriate therapeutic strategies could then be employed before an unfavorable outcome, such as infection, arises. The stability of the zwitterionic molecule in vivo provides a unique advantage in this type of scenario due to its longevity.

Polymerization

The polymeric surface modifications of the present invention may be formed by synthetic means including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), and UV, thermal, or redox free radical initiated polymerization. In a preferred embodiment, the polymer is formed using an oxidizing agent and a reducing agent, in combination, i.e., a redox pair, as the polymerization initiator in a redox free radical polymerization.

In some embodiments, it is preferable that initiators and ligands often used in ATRP such as bromine-containing initiators and ligands such as bipyridine are not used in the process as they may be non-biocompatible at certain levels. In further embodiments, it is preferred not to have a detectable level of bipyridine in the polymer modified article or in aqueous or organic extractions of the polymer modified article. In further embodiments, it is preferred not to have a detectable level of bromine in the polymer modified article or in aqueous or organic extractions of the polymer modified article. Bipyridine and bromine can be detected with HPLC or UV analysis.

Monomers can be selected such that their reactivity ratios give alternating copolymers, periodic copolymers with a pre-specified ratio of each monomer, random copolymers, block copolymers or homopolymers. Inclusion of more than two reactive groups on each monomer unit allows for the formation of star polymers, dendrimers, regularly branched polymers, randomly branched polymers, and brush polymers. In general, the monomer may be selected from any of the monomers disclosed herein. Thus, for example, the monomers may contain any of the pendant groups corresponding to Formulae ZI-1 to ZI-7. By way of further example, upon polymerization the monomers may provide the polymer with repeat units corresponding to any of Formula 1-12. In a preferred embodiment, the monomers are miscible with the polymerization mixture solvent system.

In one particularly preferred embodiment, the non-fouling polymeric materials are grafted from the primed substrate by chain growth addition polymerization. The polymerization conditions described herein are generally mild compared to other methods of polymerization and thus do not significantly alter the mechanical properties, flexibility, or dimensional properties of the underlying substrate. In one preferred embodiment, for example, polymerization is carried out at a temperature not in excess of 60° C. The polymerization may be carried out over a relatively wide pH range, e.g., about 0-10. In one embodiment, the polymerization reaction is carried out at a pH of about 2-8. For example, when DCP and ferrous gluconate are used as redox pair, the polymerization reaction may be carried out at a pH of about 6-8. By way of further example, when benzoyl peroxide and ferrous gluconate are used as redox pair, the polymerization reaction may be carried out at a pH of about 4-6. By way of further example, when O,O-t-Butyl-O-(2-ethylhexyl) monoperoxycarbonate ("TBEC") and ferrous gluconate are used as redox pair, the polymerization reaction may be carried out at a pH of about 5-7.

Chain transfer agents can be added to the monomer solution to mediate the graft-from radical polymerization reaction kinetics. Chain transfer agents include, but are not limited to, molecules containing halocarbons, thiols, dithiocarbamates, trithiocarbonates, dithioesters, xanthates, primary or secondary alcohols. Examples of chain transfer agents are bromotrichloromethane, 4-methylbenzenethiol, benzyl alcohol, methanol, ethanol, ethyleneglycol, glycerol, and isopropanol. In one embodiment the radical polymerization graftings are mediated using 2,2,6,6-tetramethylpiperidine-1-oxyl (TEMPO). In one embodiment the radical polymerization graftings are mediated using reversible addition fragmentation transfer (RAFT) agents. Examples of RAFT agents include 2-(Dodecylthiocarbonothioylthio)-2-methylpropionic acid, 2-Cyano-2-propyl benzodithioate, 2-Cyano-2-propyl dodecyl trithiocarbonate, 4-Cyano-4-(phenylcarbonothioylthio)pentanoic acid, 4-Cyano-4-[(dodecylsulfanylthiocarbonyl)sulfanyl]pentanoic acid, Bis(dodecylsulfanylthiocarbonyl) disulfide, Bis(thiobenzoyl) disulfide, Cyanomethyl dodecyl trithiocarbonate, Cyanomethyl methyl(phenyl)carbamodithioate, and their analogues and derivatives Oxygen can act as an inhibitor in free radical polymerization as it can react quickly with the free radicals generated by the initiator to form stable radical species, which in turn can react with other radical species to form unreactive species which terminate the polymerization. Therefore, creating an oxygen-free environment by degassing with nitrogen or argon or vacuum is typically used to remove oxygen before and during polymerization. However, for certain embodiments, it would preferable not to require such degassing steps in commercial production. In one preferred embodiment, the polymerization method is other than ATRP, which typically requires stringent control of oxygen levels that may be difficult to achieve during manufacturing.

Alternatively, oxygen in the system can be minimized by filling the reactor with the reaction mixtures thus physically displacing the oxygen in the reactor. In another embodiment, reagents which scavenge oxygen can be added to the reaction mixture. Suitable oxygen-scavenging reagents include, but are not limited to, sodium (meta) periodate, riboflavin, and ascorbic acid. These agents may improve the efficacy of the resulting polymer if the polymerization does not employ an inert atmosphere.

In addition to monomer and a solvent system, the polymerization mixture may optionally contain a free radical inhibitor to encourage surface grafting. Without being bound to any particular theory, it is presently believed that the addition of a free radical inhibitor to the grafting solution decreases solution polymerization, thereby allowing more monomer to be available for grafting at or near the substrate surface/polymerization mixture interface.

i. UV Initiators

In one embodiment, the initiator is an ultraviolet (UV) initiator. The substrate and initiator are typically placed into an aqueous, degassed, solution containing a zwitterionic monomer and exposed to UV light, initiating the radical polymerization. In one exemplary embodiment, the UV light has a peak wavelength of 365 nm, generated by a 100 W UV.

Examples of UV radical initiators include, but are not limited to, 1-Hydroxycyclohexyl phenyl ketone, 2,2-Diethoxyacetophenone, 2-Benzyl-2-(dimethylamino)-4'-morpholinobutyrophenone, 2-Hydroxy-2-methylpropiophenone, 2-Hydroxy-4'-(2-hydroxyethoxy)-2-methylpropiophenone, 2-Methyl-4'-(methylthio)-2-morpholinopropiophenone, 3'-Hydroxyacetophenone, 4'-Ethoxyacetophenone, 4'-Hydroxyacetophenone, 4'-Phenoxyacetophenone, 4'-tert-Butyl-2',6'-dimethylacetophenone, Diphenyl(2,4,6-trimethylbenzoyl)phosphine oxide/2-hydroxy-2-methylpropiophenone, 2,2-Dimethoxy-2-phenylacetophenone, 4,4'-Dimethoxybenzoin, 4,4'-Dimethylbenzil, Benzoin ethyl ether, Benzoin isobutyl ether, Benzoin methyl ether, Benzoin, 2-Methylbenzophenone, 3,4-Dimethylbenzophenone, 3-Hydroxybenzophenone, 3-Methylbenzophenone, 4,4'-Bis(diethylamino)benzophenone, 4,4'-Dihydroxybenzophenone, 4,4'-Bis[2-(1-propenyl)phenoxy]benzophenone, 4-(Diethylamino)benzophenone, 4-Benzoylbiphenyl, 4-Hydroxybenzophenone, 4-Methylbenzophenone, Benzophenone-3,3',4,4'-tetracarboxylic dianhydride, Benzophenone, Methyl benzoylformate, Michler's ketone, Sulfoniums, iodiums, 2-(4-Methoxystyryl)-4,6-bis(trichloromethyl)-1,3,5-triazine, Diphenyliodonium p-toluenesulfonate, N-Hydroxy-5-norbornene-2,3-dicarboximide perfluoro-1-butanesulfonate, N-Hydroxynaphthalimide triflate, 2-tert-Butylanthraquinone, 9,10-Phenanthrenequinone, Anthraquinone-2-sulfonic acid sodium salt monohydrate, Camphorquinone, Diphenyl (2,4,6-trimethylbenzoyl)phosphine oxide, 10-Methylphenothiazine, thioxanthones, and IRGRCURE 2959.

ii. Thermal Initiators

In another embodiment a heat activated (thermal) initiator is used, in place of the UV initiator described above, and the graft-from polymerization is initiated by heating the aqueous monomer solution temperature to a desired temperature and holding the temperature constant until the desired degree of polymerization is achieved.

Suitable thermal initiators include, but are not limited to, tert-Amyl peroxybenzoate, 4,4-Azobis(4-cyanovaleric acid), 2,2'-Azobis[(2-carboxyethyl)-2-methylpropionamidine], 2,2'-Azobis(4-methoxy-2,3,-dimethylvaleronitrile), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis(tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, Cumene hydroperoxide, Cyclohexanone peroxide, Dicumyl peroxide, Lauroyl peroxide, 2,4-Pentanedione peroxide, Peracetic acid, Potassium persulfate.

The temperature to which the solution is heated is dependent on the monomer and/or the initiator. Examples of thermal radical initiators include, but are not limited to, azo-compounds such as azobisisobutyronitrile (AIBN) and 1,1'-Azobis(cyclohexanecarbonitrile) (ABCN). The graft-from radical polymerization reaction is quenched by rapidly cooling the reaction solution in liquid nitrogen.

iii. Redox Initiators

In another embodiment, a redox initiator system is used to initiate polymerization from the surface of the substrate. The redox initiator system typically includes a pair of initiators: an oxidant and a reducing agent. The redox chemistry described herein can be modified to prepare non-fouling polymeric materials, for example, such as zwitterionic polymeric materials. Redox initiation is regarded as an effective one-electron transfer reaction to effectively generate free radicals under mild conditions. Suitable oxidants include, but are not limited to, peroxide, hydroperoxide, persulfates, peroxycarbonates, peroxydisulfates, peroxydiphosphate, permanganate, salts of metals such as Mn(III), Ce(IV), V(V), Co(III), Cr(VI) and Fe(III).

Suitable reducing agents include, but are not limited to, metal salts such as Fe(II), Cr(II), V(II), Ti(III), Cu(II), Ag(I), and oxyacids of sulfur, hydroxyacids, alcohols, thiols, ketones, aldehydes, amine, and amides. For example, in some embodiments, the reducing agent is an iron(II) salt, such as iron(II) L-ascorbate, ferrous sulfate, iron(II) acetate, iron(II) acetylacetonate, iron(II) ethylenediammonium sulfate, iron(II) gluconate, iron(II) lactate, iron(II) oxalate, or iron(II) sulfate.

Polymerization can be initiated by radicals formed directly from the redox reaction and/or by macroradicals formed by the abstraction of a hydrogen atom from the substrate by the transient radicals formed during the redox reaction.

In one embodiment, the substrate is coated with a undercoating coating and the non-fouling material is grafted from the undercoating layer by redox polymerization. The undercoating coating contains oxidants or reducing agents. In a preferred embodiment, the undercoating layer contains one or more reducing agents, such as acids, alcohol, thiols, ketones, aldehydes, amines and amides. An oxidant is used to react with one or more functional groups of the undercoating layer to form radicals which initiate the graft-from polymerization.

In a particular embodiment, the undercoating layer is a copolymer with pendant groups of aliphatic chains containing silanol and/or hydroxyl groups. Such materials can be used to form a undercoating layer on polymeric substrates, such as polyurethane (PU). An oxidant, such as a salt of Ce(IV), reacts with the hydroxyl group under mild conditions to form hydroxyl radicals in the undercoating layer to grow the zwitterionic polymers.

In a preferred embodiment, the hydrophilic-hydrophobic redox pair is a hydrophobic oxidizing agent/hydrophilic reducing agent pair wherein (i) the hydrophobic oxidizing agent is tert-amyl peroxybenzoate, O,O-t-Butyl-O-(2-ethylhexyl) mono-peroxycarbonate, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-Bis(tert-Butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, 4,4-azobis(4-cyanovaleric acid), or 1,1'-Azobis(cyclohexanecarbonitrile), 2,2'-Azobisisobutyronitrile (AIBN) and (ii) the hydrophilic reducing agent is $Fe^{2+}$, $Cr^{2+}$, $V^{2+}$, $Ti^{3+}$, $Co^{2+}$, $Cu^+$, or an amine; transition metal ion complexes, e.g., copper (II) acetylacetonate, $HSO^{3-}$, $SO_3^{2-}$, $S_2O_3^{2-}$, or $S_2O_5^{2-}$. Exemplary combinations include any of the aforementioned peroxides and $Fe^{2+}$. In some preferred embodiments, benzoyl peroxide, dicumyl peroxide, or O,O-t-Butyl-O-(2-ethylhexyl) mono-peroxycarbonate are used in combination with $Fe^{2+}$.

In an alternative embodiment, the hydrophilic-hydrophobic redox pair is a hydrophilic oxidizing agent/hydrophobic reducing agent pair wherein (i) the hydrophilic oxidizing agent is peracetic acid, a persulfate such as potassium persulfate, $Fe^{3+}$, $ClO^{3-}$, $H_2O_2$, $Ce^{4+}$, $V^{5+}$, $Cr^{6+}$, or $Mn^{3+}$, or their combinations; and (ii) the hydrophobic reducing agent is an alcohol, carboxylic acid, amine, or a boronalkyl or their combinations.

Other suitable redox systems include (1) organic-inorganic redox pairs, such as oxidation of an alcohol by $Ce^{4+}$, $V^{5+}$, $Cr^{6+}$, $Mn^{3+}$; (2) monomers which can act as a component of the redox pair, such as thiosulfate plus acrylamide, thiosulfate plus methacrylic acid, and N,N-dimethylaniline plus methyl methacrylate, and (5) boronalkyl-oxygen systems.

iv. Exemplary Initiators

Exemplary initiators include, but are not limited to, diacyl peroxides such as benzoyl peroxide, dichlorobenzoyl peroxide, dilauroyl peroxide, didecanoyl peroxide, diacetyl peroxide succinic acid peroxide, disuccinic peroxide and di(3,5,5-trimethylhexanoyl) peroxide. In a preferred embodiment, the diacyl peroxide is an aromatic diacyl peroxide, such as benzoyl peroxide.

Other exemplary initiators include, but are not limited to, peroxydicarbonates such as diethyl peroxydicarbonate, di-n-butyl peroxydicarbonate, diisobutyl peroxydicarbonate, di-4-tert-butylcyclohexyl peroxydicarbonate, di-sec-butyl peroxydicarbonate, di-2-ethylhexyl peroxydicarbonate, di-n-propyl peroxydicarbonate and diisopropyl peroxydicarbonate; peroxyesters, such as t-butyl perneodecanoate, t-butyl and t-amyl peroxy 2-ethyl hexanoate, and t-butyl peroxybenzoate; monoperoxycarbonates based on t-butyl and t-amyl monoperoxy 2-ethylhexyl carbonates; persulfates, such as potassium persulfate, ammonium persulfate, and sodium persulfate; cumene hydroxide, tert-butyl hydroperoxide, di(tert-amyl) peroxide, tert-butyl peroxide, 2,5-Bis(tert-butylperoxy)-2,5-dimethylhexane, 1,1-Bis(tert-butylperoxy)-3,3,5-trimethylcyclohexane; 1,1-Bis(tert-amylperoxy)cyclohexane, 1,1-Bis(tert-butylperoxy)-3,3,5-trimethylcyclohexane, 1,1-Bis(tert-butylperoxy)cyclohexane, 2,2-Bis(tert-butylperoxy)butane, 2,4-Pentanedione peroxide, 2,5-Bis(tert-butylperoxy)-2,5-dimethylhexane, 2,5-Di(tert-butylperoxy)-2,5-dimethyl-3-hexyne, 2-Butanone peroxide, cumene hydroperoxide, di-tert-amyl peroxide, dicumyl peroxide, lauroyl peroxide, tert-butyl peracetate, tert-butyl peroxide, tert-butyl peroxybenzoate, tert-butylperoxy 2-ethylhexyl carbonate, tert-Butylperoxy isopropyl carbonate, 4-nitro-bezenecarboperoxoic acid t-butyl ester, cyclohexanone peroxide, [(methylperoxy)(diphenyl)methyl]benzene, bis(t-butylcyclohexyl)peroxydicarbonate, and 2,4,6-triphenylphenoxyl dimer.

For substrates requiring coating on both internal and external surfaces, additional considerations are required for initiating polymerization. Thermal initiators can be used; however, the elevated temperature typically required can adversely affect the substrate material. UV based approaches must be designed such that they can penetrate through the material or can be applied intralumenally, for instance from a fiber optic source threaded into the lumen. This may be achieved by selecting a photoactive initiator which is labile at a UV wavelength not absorbed by the substrate polymer. Generally, lower wavelength UV irradiation is less absorbed and penetrates more readily than higher wavelength UV.

In contrast, redox chemistries generally do not require a direct line of sight to a light source to initiate polymerization since polymerization is not initiated photolytically and therefore may be advantageous for coating substrates that have one or more surfaces that are difficult to expose to the UV source, such as catheter lumens. Further, redox polymerization typically can be done at low temperatures, for example less than 60° C., less than 55° C., less than 50° C., less than 45° C., less than 40° C., less than 35° C., or less than 30° C.

The graft-from polymerization can propagate through a cationic or anionic reaction, where the substrate surface acts as the cation or anion initiator or a cationic or anionic initiator is immobilized on the substrate and the monomer contains a reactive olefin. Examples of anionic polymerization are anionic ring opening, as in the case of synthesizing polycaprolactone or polycaprolactam, where the polymerization proceeds through a lactone or lactam moiety in a ring structure containing a pendant zwitterion group. Alternatively, an organic ring containing one or more units of unsaturation and a pendant zwitterionic group are polymerized. In one embodiment a pendant olefin is included in the monomer unit and is used for crosslinking, such as in ring opening metathesis polymerization (ROMP).

Methods of Use

The materials described above may be in the form of a medical device or other article to which the non-fouling material is grafted. Suitable devices include, but are not limited to, surgical, medical or dental instruments, ophthalmic devices, wound treatments (bandages, sutures, cell scaffolds, bone cements, particles), appliances, implants, scaffolding, suturing material, valves, pacemaker, stents, catheters, rods, implants, fracture fixation devices, pumps, tubing, wiring, electrodes, contraceptive devices, feminine hygiene products, endoscopes, wound dressings and other devices, which come into contact with tissue, especially human tissue.

In one embodiment, the non-fouling materials are grafted directly from a fibrous material, incorporated into a fibrous material or grafted indirectly from a fibrous material (e.g. coated on a different surface coating). These include wound dressings, bandages, gauze, tape, pads, sponges, including woven and non-woven sponges and those designed specifically for dental or ophthalmic surgeries (See, e.g., U.S. Pat. Nos. 4,098,728; 4,211,227; 4,636,208; 5,180,375; and 6,711,879), paper or polymeric materials used as surgical drapes, disposable diapers, tapes, bandages, feminine products, sutures, and other fibrous materials.

Fibrous materials are also useful in cell culture and tissue engineering devices. Bacterial and fungal contamination is a major problem in eukaryotic cell culture and this provides a safe and effective way to minimize or eliminate contamination of the cultures, while allowing selective attachment of the desired cells through the incorporation of directed adhesion proteins into the material.

The non-fouling agents are also readily bound to particles, including nanoparticles, microparticles, millimeter beads, or formed into micelles, that have uses in a variety of applications including cell culture, as mentioned above, and drug delivery. Non-fouling, biocompatible, polymeric micelles would prevent protein denaturation preventing activation of the immune response allowing for a more stealthy delivery of the desired therapeutic.

The non-fouling material can also be applied directly to, or incorporated in, polymeric, metallic, or ceramic substrates. Suitable devices include, but are not limited to surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronization therapy devices, ventricular assist devices, heart valves, catheters (including vascular, urinary, neurological, peritoneal, interventional, etc.), shunts, wound drains, dialysis membranes, infusion ports, cochlear implants, endotracheal tubes, guide wires, fluid collection bags, sensors, wound treatments (dressings, bandages, sutures, cell scaffolds, bone cements, particles), ophthalmic devices, orthopedic devices (hip implants, knee implants, spinal implants, screws, plates, rivets, rods, intramedullary nails, bone cements, artificial tendons, and other prosthetics or fracture repair devices), dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices, or other medical devices used within or in contact with the body or any portion of any of these. Preferably, the non-fouling coating herein does not significantly adversely affect the desired physical properties of the device including, but not limited to, flexibility, durability, kink resistance, abrasion resistance, thermal and electrical conductivity, tensile strength, hardness, burst pressure, etc.

In one embodiment, the substrate is a vascularly inserted catheter such as a peripherally inserted central catheter (PICC), central venous catheter (CVC) or hemodialysis catheter, venous valves, punctual plugs, and intra-ocular devices and implants.

In another embodiment, the substrate is a vascularly inserted catheter formed from a medical grade polyurethane or CARBOTHANE® or formed from a material coated with a medical grade polyurethane or polycarbothane.

In one specific embodiment, the catheter comprises an elongated catheter body containing multiple lumens. For example, the catheter may be a double-lumen or a triple-lumen catheter. The lumens may be coaxial or side-by-side. In one exemplary embodiment, the catheter body has two side-by-side lumens, each having a "D" shape and the catheter body has a length that is greater than 5 cm; typically the catheter body of such catheters have a length of at least 11 cm. In one particularly preferred embodiment, the catheter body is a medical-grade polycarbonate-based aliphatic and aromatic polyurethane.

The non-fouling materials can also be added to paints and other coatings and filters to prevent mildew, bacterial contamination, and in other applications where it is desirable to prevent fouling, such as marine applications (ship hull coatings), contact lenses, dental implants, coatings for in vivo sensors, devices for separations, such as membranes for microbial suspension, biomolecule separation, protein fractionation, cell separation, waste water treatment, bioreactors, and food processing.

Other applications include the treatment of fibers, particulates and films for applications in textiles, additives, electric/optical appliances, packaging materials and colorants/inks.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

Preparation of a Coated Substrate by Controlled Radical Polymerization

Example 1

Preparation of an Undercoating

An undercoating, with reactive functional groups for modification was prepared through free radical polymerization. Lauryl methacrylate (LMA, 0-50 mol %), 2-hydroxyproyl methacyrlate (HPMA, 0-75 mol %), hydroxyethyl methacrylate (HEMA, 0-75 mol %), and 3-(trimethoxysilyl)propyl methacrylate (TMSPMA, 0-25 mol %) were mixed in methanol. Azobisisobutyronitrile (AIBN), an initiator, was added and the reaction solution was heated to 60-65° C. for 16-24 hours with stirring under nitrogen. The crude polymer was purified by dialysis against methanol.

Coating a Substrate Surface with an Undercoating

A substrate was dipped into a solution of methanol containing the purified undercoating polymer. The thickness of the undercoating could be tailored by varying the concentration of the polymer in solution or by increasing the number and speed of each dip. After this dipping treatment the coating was cured in an oven (37-80° C.) for 16-24 hours.

Undercoating Modification for Controlled Radical Polymerization

The coated substrate was then primed for controlled radical polymerization by reacting the surface functional groups with a reactive controlled radical polymerization initiator. The coated substrate was loaded into a flask charged with hexane and triethylamine (1.05 eq.) and cooled to 0° C. in an ice bath. α-bromoisobutyryl bromide (1.00 eq.) was then added dropwise, and the mixture was warmed to room temperature and left stirring 16-24 hours. The substrate was washed of excess reactant by several sequential rounds of washing in hexane, methanol, and deionized water.

Controlled Radical Polymerization

The 'primed' substrate was then coated in a biofunctional polymer layer by controlled radical polymerization. The substrate was added to a flask containing a stir bar and copper (I) bromide (CuBr, 1 eq.) and bipyridine (Bpy, 2 eq.). A separate flask was charged with a 10-20 wt % solution of N-(3-sulfopropyl)-N-methacryloyloxyethyl-N,N-dimethylammonium betaine (SBMA) in deionized water. Both flasks were deoxygenated by bubbling through Argon for 20-30 minutes, followed by addition of the SBMA solution to the substrate-charged flask by cannulation. The reaction was allowed to proceed at 20-60° C. with stirring for 1-48 hours. After the allotted time, the reaction flask was opened to the air, and the solution was decanted. The coated substrate was washed extensively in phosphate buffered saline (PBS, 1×) to remove excess reactant.

Example 2

Preparation of a 'Primed' Undercoating

In another iteration, a 'primed' undercoating was prepared that did not require an additional modification step prior to controlled radical polymerization. Lauryl methacrylate (LMA, 0-50 mol %), Vinylbenzyl chloride (VBC, 0-100 mol %), and 3-(trimethoxysilyl)propyl methacrylate (TMSPMA, 0-25 mol %) were mixed in methanol. Azobisisobutyronitrile (AIBN), an initiator, was added and the reaction solution was heated to 60-65° C. for 16-24 hours with stirring under nitrogen. The crude polymer was either purified by dialysis against methanol or by washing the solid precipitate several times in methanol and drying in vacuo.

Coating a Substrate Surface with a 'Primed' Undercoating

A substrate was dipped into a solution of either methanol (VBC copolymers) or a hexane/dichloromethane mixture (VBC homopolymer, 0-50 vol % hexane) containing the purified 'primed' undercoating polymer. The thickness of the undercoating could be tailored by varying the concentration of the polymer in solution or by increasing the number and speed of each dip. After this dipping treatment the coating was cured in an oven (37-80° C.) for 16-24 hours.

Controlled Radical Polymerization

The 'primed' substrate was then coated in a biofunctional polymer layer by controlled radical polymerization. The substrate was added to a flask containing a stir bar and copper (I) chloride (CuCl, 1 eq.) and bipyridine (Bpy, 2 eq.). A separate flask was charged with a 10-20 wt % solution of N-(3-sulfopropyl)-N-methacryloyloxyethyl-N,N-dimethylammonium betaine (SBMA) in deionized water. Both flasks were deoxygenated by bubbling through Argon for 20-30 minutes, followed by addition of the SBMA solution to the substrate-charged flask by cannulation. The reaction was allowed to proceed at 20-60° C. with stirring for 1-48 hours. After the allotted time, the reaction flask was opened to the air, and the solution was decanted. The coated substrate was washed extensively in phosphate buffered saline (PBS, 1×) to remove excess reactant.

Example 3

Preparation of a 'Primed' Undercoating

In another iteration, a 'primed' undercoating was prepared that did not require an additional modification step prior to controlled radical polymerization. Lauryl methacrylate (LMA, 0-50 mol %), 2-(2-bromoisobutyryloxyl)ethyl methacrylate (BIEM, 0-100 mol %), and 3-(trimethoxysilyl) propyl methacrylate (TMSPMA, 0-25 mol %) were mixed in methanol. Azobisisobutyronitrile (AIBN), an initiator, was added and the reaction solution was heated to 60-65° C. for 16-24 hours with stirring under nitrogen. The crude polymer was purified by washing the solid precipitate several times in methanol and drying in vacuo.

Coating a Substrate Surface with a 'Primed' Undercoating

A substrate was dipped into a solution containing the purified 'primed' undercoating polymer. The thickness of the undercoating could be tailored by varying the concentration of the polymer in solution or by increasing the number and speed of each dip. After this dipping treatment the coating was cured in an oven (37-80° C.) for 16-24 hours.

Controlled Radical Polymerization

The 'primed' substrate was then coated in a biofunctional polymer layer by controlled radical polymerization. The substrate was added to a flask containing a stir bar and copper (I) bromide (CuBr, 1 eq.) and bipyridine (bpy, 2 eq.). A separate flask was charged with a 10-20 wt % solution of N-(3-sulfopropyl)-N-methacryloyloxyethyl-N,N-dimethyl-ammonium betaine (SBMA) in deionized water. Both flasks were deoxygenated by bubbling through Argon for 20-30 minutes, followed by addition of the SBMA solution to the substrate-charged flask by cannulation. The reaction was allowed to proceed at 20-60° C. with stirring for 1-48 hours. After the allotted time, the reaction flask was opened to the air, and the solution was decanted. The coated substrate was washed extensively in phosphate buffered saline (PBS, 1×) to remove excess reactant.

Example 4

Imbibing Initiator

A substrate was prepared for graft-from radical polymerization by soaking peroxide directly into the substrate layer. The substrate was dipped in a 1-10% (w/v) solution of an organic peroxide in acetone, ethanol, heptane, or a mixture of those solvents. The substrate was left soaking in peroxide solution for 1-24 hours, after which time it was rinsed thoroughly in the respective solvent and dried at room temperature in the dark.

Preparation of an Undercoating

An undercoating, with reactive functional groups for modification was prepared through graft-from radical polymerization. The peroxide-imbibed substrate was loaded into a flask and filled with 1-20% (w/w) of hydroxyethyl methacrylate (HEMA) or polyethylene glycol methacrylate (OEGMA) in deionized water. The flask was deoxygenated for up to 30 minutes by bubbling through nitrogen, followed by the addition of iron (II) gluconate to a final concentration of 5 mM. The flask was deoxygenated for an additional 10 minutes, then heated to 60° C. for 5 hours with stirring.

Undercoating Modification for Controlled Radical Polymerization

The coated substrate was then primed for controlled radical polymerization by reacting the surface functional groups with a reactive controlled radical polymerization initiator. The coated substrate was loaded into a flask charged with hexane and triethylamine (1.05 eq.) and cooled to 0° C. in an ice bath. α-bromoisobutyryl bromide (1.00 eq.) was then added dropwise, and the mixture was warmed to room temperature and left stirring 16-24 hours. The substrate was washed of excess reactant by several sequential rounds of washing in hexane, methanol, and deionized water.

Controlled Radical Polymerization

The 'primed' substrate was then coated in a biofunctional polymer layer by controlled radical polymerization. The substrate was added to a flask containing a stir bar and copper (I) bromide (CuBr, 1 eq.) and bipyridine (bpy, 2 eq.). A separate flask was charged with a 10-20 wt % solution of N-(3-sulfopropyl)-N-methacryloyloxyethyl-N,N-dimethyl-ammonium betaine (SBMA) in deionized water. Both flasks were deoxygenated by bubbling through Argon for 20-30 minutes, followed by addition of the SBMA solution to the substrate-charged flask by cannulation. The reaction was allowed to proceed at 20-60° C. with stirring for 1-48 hours. After the allotted time, the reaction flask was opened to the air, and the solution was decanted. The coated substrate was washed extensively in phosphate buffered saline (PBS, 1×) to remove excess reactant.

Example 5

Imbibing Substrate in Initiator and Monomer

A substrate was prepared for graft-from radical polymerization by soaking peroxide and monomer directly into the substrate layer. The substrate was dipped in a 1-10% (w/v) solution of an organic peroxide and 1-20% (w/v) of functional monomer (OEGMA, VBC) in acetone, ethanol, heptane, dichloromethane, or a mixture of those solvents. The substrate was left soaking in peroxide/monomer solution for 1-24 hours, after which time it was rinsed thoroughly in the respective solvent and dried at room temperature in the dark.

Preparation of an Undercoating

An undercoating, with reactive functional groups for modification was prepared through graft-from radical polymerization. The peroxide/monomer-imbibed substrate was loaded into a flask containing deionized water, deoxygenated for up to 20 minutes by bubbling through nitrogen, followed by the addition of iron (II) gluconate to a final concentration of 5 mM. The flask was deoxygenated for an additional 10 minutes, then heated to 60° C. for 5 hours with stirring.

Undercoating Modification for Controlled Radical Polymerization

The coated substrate was then primed for controlled radical polymerization by reacting the surface functional groups with a reactive controlled radical polymerization initiator. The coated substrate was loaded into a flask charged with hexane and triethylamine (1.05 eq.) and cooled to 0° C. in an ice bath. α-bromoisobutyryl bromide (1.00 eq.) was then added dropwise, and the mixture was warmed to room temperature and left stirring 16-24 hours. The substrate was washed of excess reactant by several sequential rounds of washing in hexane, methanol, and deionized water.

Controlled Radical Polymerization

The 'primed' substrate was then coated in a biofunctional polymer layer by controlled radical polymerization. The substrate was added to a flask containing a stir bar and copper (I) bromide (CuBr, 1 eq.) and bipyridine (bpy, 2 eq.). A separate flask was charged with a 10-20 wt % solution of N-(3-sulfopropyl)-N-methacryloyloxyethyl-N,N-dimethyl-ammonium betaine (SBMA) in deionized water. Both flasks were deoxygenated by bubbling through Argon for 20-30 minutes, followed by addition of the SBMA solution to the substrate-charged flask by cannulation. The reaction was allowed to proceed at 20-60° C. with stirring for 1-48 hours. After the allotted time, the reaction flask was opened to the air, and the solution was decanted. The coated substrate was washed extensively in phosphate buffered saline (PBS, 1×) to remove excess reactant.

What is claimed is:

1. A process for the preparation of article of manufacture, the process comprising
    (1) depositing a polymeric primer on a substrate, the polymeric primer having a thickness of at least 50 nm comprising and containing at least 5 nanomolar equivalent/cm$^2$ of a functional group, and
    (2) grafting a polymer from the deposited polymeric primer, the deposited polymeric primer being between the grafted polymer and the substrate and having upper and lower surfaces, the lower surface covering at least a portion of the substrate, and the upper surface being bound to the functional group, the polymeric primer and the grafted polymer, in combination, constituting a modified surface having a fibrinogen adsorption of less than about 75 ng/cm$^2$ in a fibrinogen binding assay in which the modified surface is incubated for 60 minutes at 37° C. in 70 µg/ml fibrinogen derived from human plasma containing 1.4 µg/ml I-125 radiolabeled fibrinogen.

2. The process of claim 1 wherein the polymer is grafted by exposing the functional group to a free radical initiator and a monomer or monomer mixture, the upper surface of the polymeric primer being attached to the grafted polymer through the functional group.

3. The process of claim 2, wherein the free radial initiator is selected from UV, thermal, and redox initiators.

4. The process of claim 3 wherein the free radical initiator is a redox initiator comprising an oxidant selected from the following: peroxide, hydroperoxide, persulfates, peroxycarbonates, peroxydisulfates, peroxydiphosphate, permanganate, salts of metals such as Mn(III), Ce(IV), V(V), Co(III), Cr(VI) and Fe(III).

5. The process of claim 1 wherein the functional group is selected from the group consisting of glycidyl, isocyanate, amine, benzophenone, bromoisobutyryl, hydroxy, carboxylate and combinations thereof.

6. The process of claim 1 wherein the deposited polymeric primer has a thickness from 50 nm to 500 µm.

7. The process of claim 1 wherein the grafted polymer and the polymeric primer, in combination have a global average dry thickness of at least 500 nm.

8. The process of claim 1 wherein the grafted polymer and the polymeric primer, in combination, have a global average dry thickness that is at least equal to the global average R$_{rms}$ surface roughness of the substrate surface.

9. The process of claim 1 wherein the modified surface has a static contact angle less than 40 degrees.

10. The process of claim 1 wherein the difference between the static contact angle of the polymeric primer, prior to the attachment of the grafted polymer, and the modified surface is at least 10 degrees.

11. The process of claim 1 wherein the polymeric primer contains at least 5 nanomolar equivalents/cm$^2$ of a functional group that is chemically reactive with a functionality of the grafted polymer or of a moiety from which it is derived.

12. The process of claim 1 wherein covalent bonds are formed between at least one of the following: (a) the grafted polymer and the deposited polymeric primer; or (b) the deposited polymeric primer and the substrate.

13. The process of claim 1 wherein the grafted polymer has a global average dry thickness in the range from about 100 nm to about 1000 nm.

14. The process of claim 1, wherein the grafted polymer is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide or carboxybetaine methacrylamide monomers and the grafted polymer has an average dry thickness of at least about 50 nm as measured by SEM under vacuum.

15. The process of claim 1 further comprising pretreating the substrate with an acid, base or chelating agent to remove particles or waxes from the surface of the substrate on which the polymeric primer is deposited thereon, wherein the pretreating occurs prior to the depositing the polymeric primer.

16. The process of claim 1 further comprising mechanically, chemically, or chemomechanically treating the surface of the substrate on which the polymeric primer is deposited thereon to reduce surface defects prior to the depositing the polymeric primer.

17. The process of claim 1 wherein the depositing the polymeric primer includes exposing the substrate to a solution comprising a pre-synthesized polymer and a solvent.

18. The process of claim 1 wherein the depositing the polymeric primer includes exposing the substrate to a solution comprising a monomer, an initiator and a solvent.

19. The process of claim 1 wherein the polymeric primer includes a copolymer comprising: 0-50 mol % lauryl methacrylate (LMA); 0-50 mol % 2-hydroxypropyl methacrylate (HPMA); and 0-25 mol % trimethoxysilyl methacrylate (TMOSMA).

20. The process of claim 1 wherein the grafted polymer includes a copolymer comprising 25-90 mol % sulfobetaine methacrylate (SBMA) and 75-10 mol % 2-hydroxypropyl methacrylate (HPMA).

21. The process of claim 1 further comprising treating the deposited polymeric primer with an initiator prior to the grafting the polymer from the deposited polymeric primer.

22. The process of claim 21 wherein the treating the deposited polymeric primer comprises imbibing an initiator into the deposed polymeric primer.

23. The process of claim 1 wherein the polymeric primer comprises a reactive group that is chemically reactive with a functionality of the substrate to attach the polymeric primer to the substrate.

24. The process of claim 23 wherein the reactive group is selected from the group consisting of an alkyne, primary amine, secondary amine, tertiary amine, anhydride, azide, carboxyl, epoxy, glycidyl, halogen, hydroxyl, isocyanate, peroxide, silanol, thiol, photo-initiator groups, and combinations thereof.

* * * * *